US012560505B2

(12) United States Patent
Stephens et al.

(10) Patent No.: US 12,560,505 B2
(45) Date of Patent: Feb. 24, 2026

(54) DETECTION OF STRUCTURAL ANOMALIES IN A PIPELINE NETWORK

(71) Applicant: THE UNIVERSITY OF ADELAIDE, Adelaide (AU)

(72) Inventors: Mark Leslie Stephens, Adelaide (AU); Luke Dix, Adelaide (AU); Chi Zhang, Adelaide (AU); Jinzhe Gong, Adelaide (AU); Benjamin Cazzolato, Adelaide (AU); Martin F. Lambert, Adelaide (AU)

(73) Assignee: THE UNIVERSITY OF ADELAIDE, Adelaide (AU)

( * ) Notice: Subject to any disclaimer, the term of this patent is extended or adjusted under 35 U.S.C. 154(b) by 661 days.

(21) Appl. No.: 17/605,678

(22) PCT Filed: Apr. 24, 2020

(86) PCT No.: PCT/AU2020/000035
§ 371 (c)(1),
(2) Date: Oct. 22, 2021

(87) PCT Pub. No.: WO2020/215116
PCT Pub. Date: Oct. 29, 2020

(65) Prior Publication Data
US 2022/0205956 A1 Jun. 30, 2022

(30) Foreign Application Priority Data
Apr. 24, 2019 (AU) ................................ 2019901400
Apr. 24, 2019 (AU) ................................ 2019901401

(51) Int. Cl.
*G01M 3/24* (2006.01)
*E03B 7/00* (2006.01)
(Continued)

(52) U.S. Cl.
CPC ............. *G01M 3/243* (2013.01); *E03B 7/003* (2013.01); *E03B 7/02* (2013.01); *G01N 29/12* (2013.01);
(Continued)

(58) Field of Classification Search
CPC .. G01M 3/243; G01M 5/0025; G01M 5/0033; G01M 3/2807; E03B 7/003;
(Continued)

(56) References Cited

U.S. PATENT DOCUMENTS

| | | | | | |
|---|---|---|---|---|---|
| 6,668,619 | B2 * | 12/2003 | Yang | ..................... | G01M 3/243 |
| | | | | | 73/40.5 R |
| 2002/0042692 | A1 * | 4/2002 | Gross | ..................... | G01R 23/16 |
| | | | | | 702/183 |

(Continued)

FOREIGN PATENT DOCUMENTS

| | | | | | |
|---|---|---|---|---|---|
| GB | 2553833 | A | * | 3/2018 | ............. E03B 7/003 |
| WO | WO 2018/051287 | | | 3/2018 | |

OTHER PUBLICATIONS

B. Khan et al. "Acoustic Characterization of PVC Sewer Pipes for Crack Detection Using Frequency Domain Analysis," 2018 IEEE International Smart Cities Conference (ISC2) (2018, pp. 1-5. (Year: 2018).*

(Continued)

*Primary Examiner* — Eman A Alkafawi
*Assistant Examiner* — Dilara Sultana
(74) *Attorney, Agent, or Firm* — Sheridan Ross P.C.

(57) ABSTRACT

Methods of processing a data signal obtained from a sensor sensing a dynamic signal to detect a structural anomaly event are disclosed. In one embodiment, a method includes obtaining signal components attributable to fluid flow at a location within an operational pipeline network; processing the data signal to extract one or more features; characterising (Continued)

the one or more extracted features; and detecting an indication of a structural anomaly event proximal the location depending on the characterisation; wherein the structural anomaly event includes an occurrence and/or further development of a structural anomaly.

26 Claims, 48 Drawing Sheets

(51) Int. Cl.

| | | |
|---|---|---|
| *E03B 7/02* | (2006.01) | |
| *G01N 29/12* | (2006.01) | |
| *G01N 33/2045* | (2019.01) | |

(52) U.S. Cl.
CPC . *G01N 33/2045* (2019.01); *G01N 2291/0234* (2013.01)

(58) Field of Classification Search
CPC ........... E03B 7/02; E03B 7/071; G01N 29/12; G01N 33/2045; G01N 2291/0234; Y02A 20/01; F17D 5/06; G01H 3/10; G01H 3/04; G01F 19/00; G01F 1/20; G01F 1/02
See application file for complete search history.

(56) References Cited

U.S. PATENT DOCUMENTS

| | | |
|---|---|---|
| 2005/0279169 A1 | 12/2005 | Lander |
| 2006/0174707 A1 | 8/2006 | Zhang |
| 2008/0143344 A1 | 6/2008 | Focia et al. |
| 2013/0179095 A1 | 7/2013 | Stevens et al. |
| 2014/0005958 A1* | 1/2014 | Baliga .................... G01M 3/243 |
| | | 702/51 |
| 2014/0165731 A1 | 6/2014 | Linford |
| 2015/0205000 A1* | 7/2015 | Perkins ..................... G01V 8/10 |
| | | 702/8 |
| 2015/0276545 A1 | 10/2015 | Takahashi et al. |
| 2016/0035370 A1* | 2/2016 | Krini ....................... G10L 21/02 |
| | | 704/209 |
| 2018/0306753 A1* | 10/2018 | Perrier ................... G01N 29/07 |
| 2018/0347763 A1* | 12/2018 | Ford ......................... F17D 5/06 |
| 2018/0351786 A1* | 12/2018 | Pope ....................... H04L 67/34 |
| 2019/0128766 A1* | 5/2019 | Burtea .................... G06F 17/40 |

OTHER PUBLICATIONS

C. Yuan et al. "Research to Real-time Algorithm of Crack Initiation Monitoring Based on Welch's Method", Proceedings of 2014 IEEE Chinese Guidance, Navigation and Control Conference Aug. 8-10, 2014. (Year: 2014).*

Boll "Suppression of Acoustic Noise in Speech Using Spectral Subtraction," IEEE Transactions on Acoustics, Speech, and Signal Processing, Apr. 1979, vol. ASSP-27, No. 2, pp. 113-120.

Ephraim et al. "Speech Enhancement Using a Minimum Mean-Square Error Short-Time Spectral Amplitude Estimator," IEEE Transactions on Acoustics, Speech, and Signal Processing, Dec. 1984, vol. ASSP-32, No. 6, pp. 1109-1121.

International Search Report and Written Opinion for International (PCT) Patent Application No. PCT/AU2020/000035, dated Jul. 7, 2020, 8 pages.

Official Action for Australia Patent Application No. 2020262969, dated Dec. 22, 2022, 3 pages.

Extended Search Report for European Patent Application No. 20795212.8, dated Jan. 9, 2023, 8 pages.

* cited by examiner

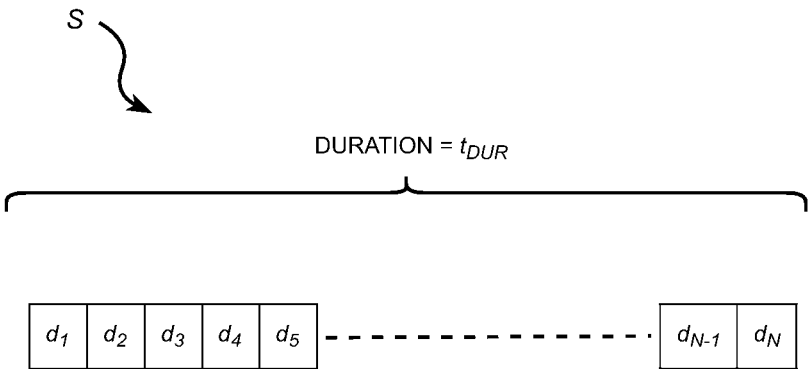
FIGURE 7A
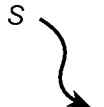
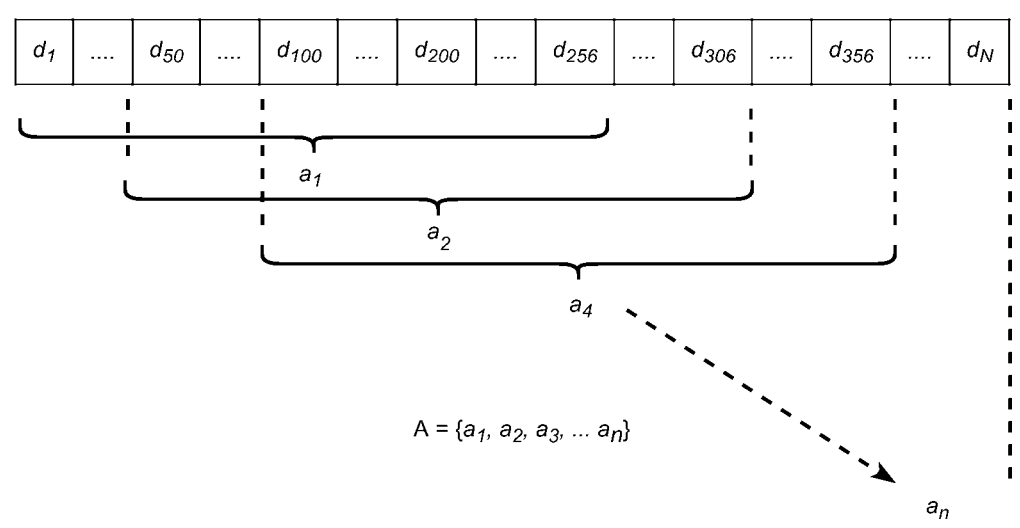
$$A = \{a_1, a_2, a_3, \dots a_n\}$$
FIGURE 7B

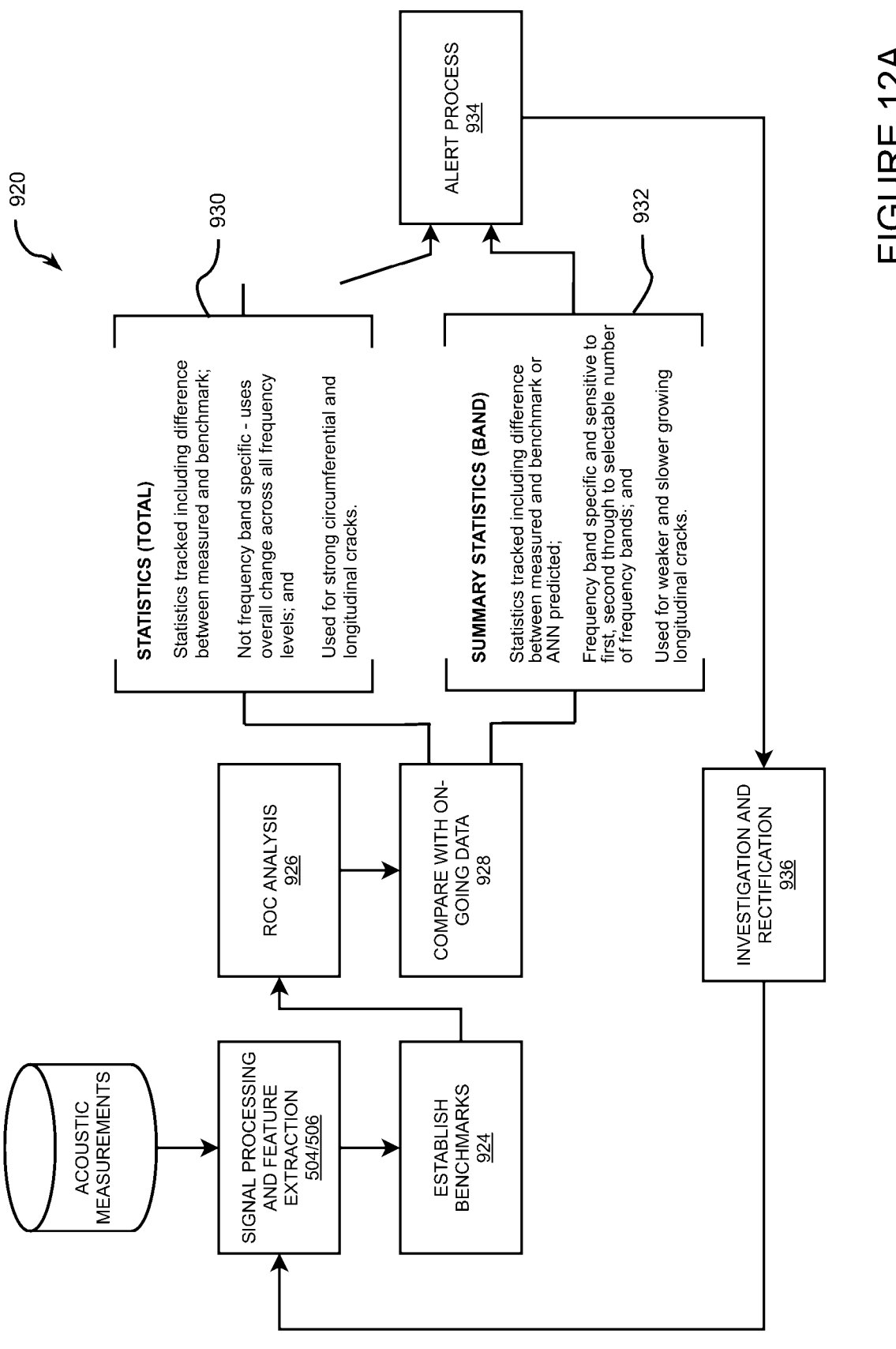

920

930

STATISTICS (TOTAL)

Statistics tracked including difference between measured and benchmark;

Not frequency band specific - uses overall change across all frequency levels; and Used for strong circumferential and longitudinal cracks.

932

SUMMARY STATISTICS (BAND)

Statistics tracked including difference between measured and benchmark or ANN predicted;

Frequency band specific and sensitive to first, second through to selectable number of frequency bands; and Used for weaker and slower growing longitudinal cracks.

ALERT PROCESS
934

ROC ANALYSIS
926

COMPARE WITH ON-GOING DATA
928

INVESTIGATION AND RECTIFICATION
936

ACOUSTIC MEASUREMENTS

SIGNAL PROCESSING AND FEATURE EXTRACTION
504/506

ESTABLISH BENCHMARKS
924

FIGURE 12A (a)

(b) Zoomed-in of box in (a)

Median Frequency
ANN Prediction

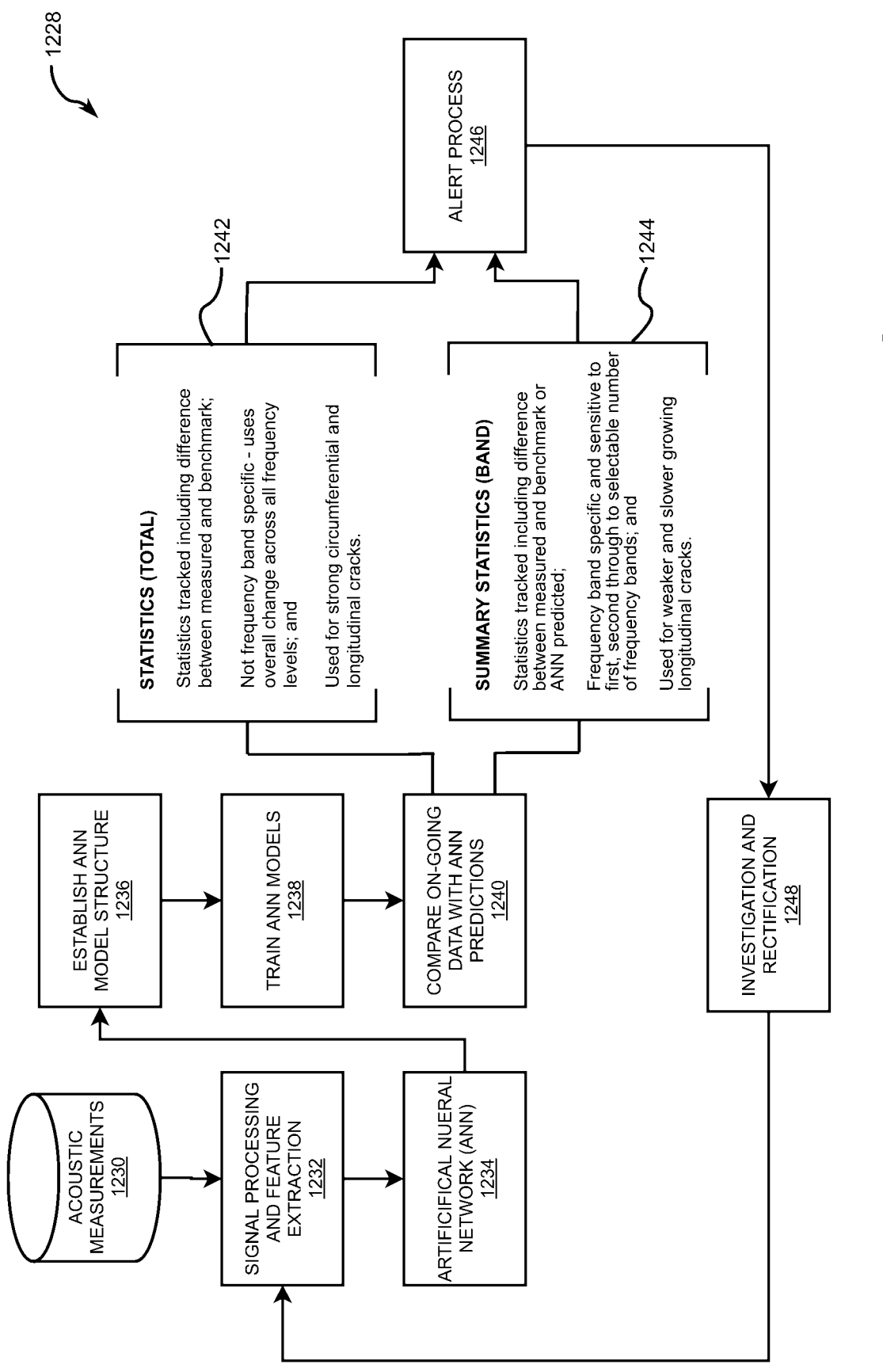

1228

1242

STATISTICS (TOTAL)

Statistics tracked including difference between measured and benchmark;

Not frequency band specific - uses overall change across all frequency levels; and Used for strong circumferential and longitudinal cracks.

1244

SUMMARY STATISTICS (BAND)

Statistics tracked including difference between measured and benchmark or ANN predicted;

Frequency band specific and sensitive to first, second through to selectable number of frequency bands; and Used for weaker and slower growing longitudinal cracks.

ALERT PROCESS 1246

ESTABLISH ANN MODEL STRUCTURE 1236

TRAIN ANN MODELS 1238

COMPARE ON-GOING DATA WITH ANN PREDICTIONS 1240

INVESTIGATION AND RECTIFICATION 1248

ACOUSTIC MEASUREMENTS 1230

SIGNAL PROCESSING AND FEATURE EXTRACTION 1232

ARTIFICIFICAL NUERAL NETWORK (ANN) 1234

FIGURE 25

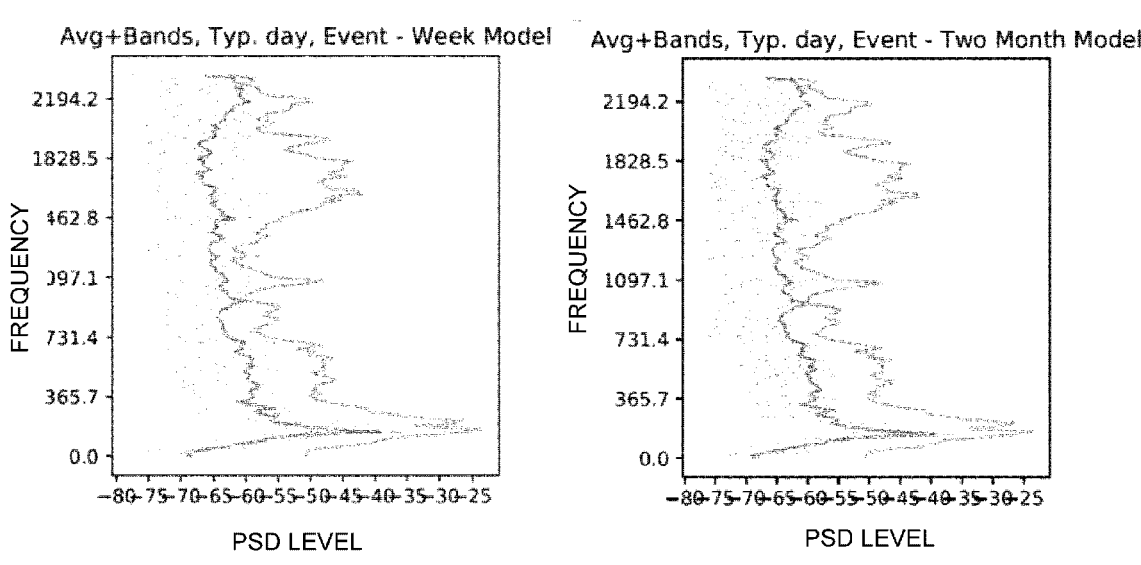
ONE WEEK MODEL                                    TWO-MONTH MODEL
FIGURE 26                    FIGURE 27

NOT A LEAK, IDENTIFIED AS NOT A LEAK

NOT A LEAK, IDENTIFIED AS A LEAK

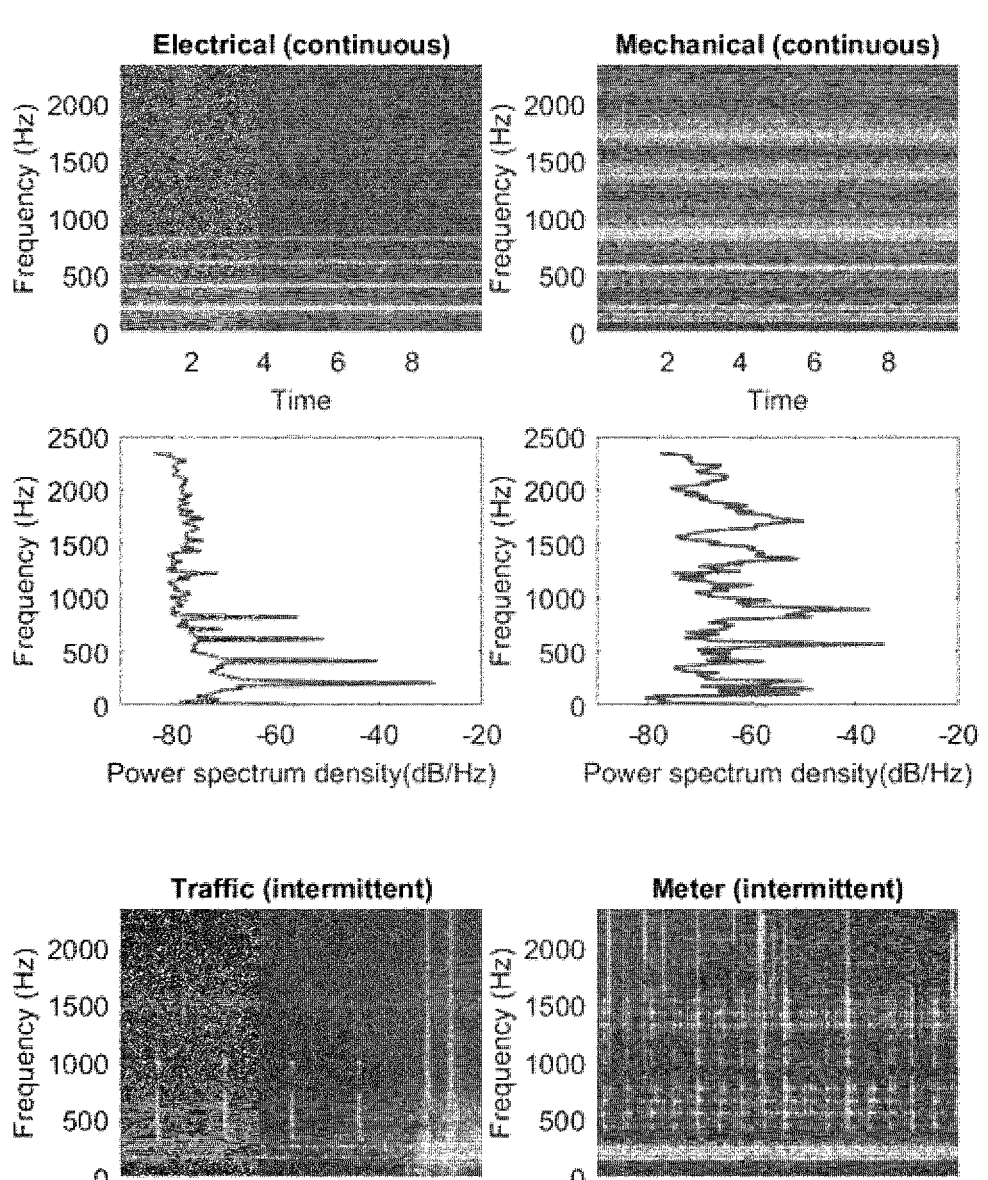
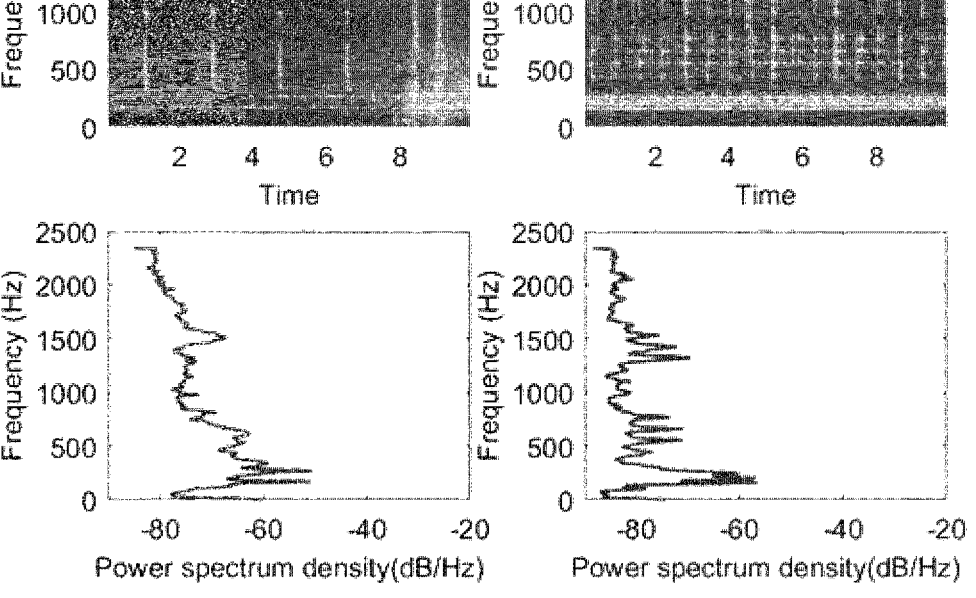
FIGURE 38A (a)

(b)

| FAULT TYPE | CHARACTERISTIC | | | | | |
|---|---|---|---|---|---|---|
| | PERSISTENCY AFTER FAULT | FREQUENCY PEAKS (NUMBER AND MAGNITUDE) | INITIAL SIGNAL MAGNITUDE | CHANGES IN FREQUENCY AND MAGNITUDE (SAME RELATIVE CHANGE THRESHOLD) | RATE OF CHANGE IN FREQUENCY AND MAGNITUDE | GAUSSIAN OR NON-GAUSSIAN |
| CIRCUMFERENTIAL CRACK (OR LEAK ON VALVE NOT ON LOGGER) | 100% | SINGLE AND MEDIUM TO HIGH (BOTH FREQUENCY AND MAGNITUDE) DEPENDING ON DISTANCE TO FAULT | MEDIUM TO HIGH | FEW (OR NONE) | VERY FAST FOR INITIAL EVENT AND THEN NONE | GAUSSIAN |
| LONGITUDINAL CRACK | HIGH (BUT NOT ALWAYS 100%) | INITIALLY SINGLE AND THEN MULTIPLE WITH MEDIUM TO HIGH FREQUENCIES AND MAGNITUDES (SOMETIMES LOW) DEPENDING ON DISTANCE TO FAULT | LOW | SIGNIFICANT OVER TIME | SLOW WHEN STABLE CRACK GROWTH IN DETERIORATED (CORRODED) PIPE WALL AND THEN ACCELERATING WHEN UNSTABLE CRACK GROWTH | GAUSSIAN |
| CUSTOMER SIDE LEAK | HIGH (BUT NOT ALWAYS 100%) | VARIABLE DEPENDING ON RATE OF FLOW THROUGH WATER METER AND/OR TRANSMISSION OF CUSTOMER PLUMBING LEAK NOISE BACK THROUGH WATER METER | VARIABLE | FEW | VARIABLE | NON-GAUSSIAN |

FIGURE 41

DETECTION OF STRUCTURAL ANOMALIES IN A PIPELINE NETWORK

INCORPORATION BY REFERENCE

The present application is a national stage application under 35 U.S.C. 371 and claims the benefit of PCT Application No PCT/AU2020/000035 having an international filing date of 24 Apr. 2020, which designed the United States, which PCT application claimed the benefit of Australian Provisional Patent Application No. 2019901401 filed 24 Apr. 2019, Australian Provisional Patent Application No. 2019901400 filed on 24 Apr. 2019, be contents of each of which are incorporated herein by reference in their entireties.

TECHNICAL FIELD

The present invention relates to systems and methods for detection of a structural anomaly event in an operational pipeline network. In an embodiment, a method may detect fractures, such as a crack, in an operational mains water distribution pipeline network.

BACKGROUND

Water main breaks cause significant problems across the globe. They can lead to traffic interruptions, property damage and result in negative publicity for water utilities. In the central business district areas of cities areas, damage to third party buried telecommunication and power infrastructure caused by uncontrolled main breaks is a significant additional problem.

Currently, the management of water main breaks is largely reactive. Uncontrolled main breaks are fixed after detection and the deployment of reactive operational repair crews. In some cases, a section of water main may be replaced after several uncontrolled breaks have been experienced. Should current reactive practices continue, the number of uncontrolled water main breaks will likely increase as water pipeline infrastructure ages.

Water utilities worldwide are looking for solutions to reduce uncontrolled water main break rates and improve their service to the public. In recent years, continuous pressure monitoring systems (for transient and/or steady-state pressure management) involving a sensor network have been used and corresponding analysis techniques have been developed to detect and locate pipe main breaks after their occurrences. However, such continuous transient monitoring for main break detection is still a reactive practice and most main breaks are first brought to the attention of the water utility via public reporting rather than through the sensor network.

It would be desirable to provide a more proactive approach which prevents, or at least reduces, the occurrence of uncontrolled pipe main breaks by detecting and fixing the developing pipe cracks before uncontrolled failures.

SUMMARY

The present disclosure involves processing a data signal from one or more sensors to obtain an indication of an occurrence and/or further development of a structural anomaly event at one or more locations within an operational pipeline network. Thus, in its most general form, the present invention provides a method of processing a data signal to obtain an indication of the occurrence, attributes and/or further development of a structural anomaly event within an operational pipeline network.

According to one aspect of an embodiment of the present disclosure there is provided a method of processing a data signal obtained from a sensor sensing a dynamic signal including signal components attributable to fluid flow at a location within an operational pipeline network, the method including:

processing the data signal to extract one or more features;
characterising the one or more extracted features; and
detecting an indication of a structural anomaly event proximal the location depending on the characterisation;
wherein the structural anomaly event includes an occurrence and/or further development of a structural anomaly.

In one embodiment, the operational pipeline network is a mains water distribution pipeline network. For example, the operational mains water distribution pipeline network may include a mains water distribution pipeline network including a network of cast iron pipes.

In an embodiment, detecting an indication of a structural anomaly event includes:

detecting an indication of a circumferential crack in a pipe;
detecting an indication of longitudinal crack in a pipe;
detecting an indication of a joint leak in a jointed pipe;
detecting an indication of a leak in a customer connection to a pipe; or
detecting an indication of a small blow-out in a pipe which has not resulted in surface activity;
according to characteristics of the one or more extracted features.

According to yet another aspect of an embodiment of the present disclosure there is provided a system for processing a data signal obtained from a sensor sensing a dynamic signal including signal components attributable to fluid flow at a location within an operational pipeline network, the system including:

a memory;
a set of computer readable instructions stored in the memory;
a processor for executing the set of computer readable instructions to:
process the data signal to extract one or more features;
characterise the one or more extracted features; and
detect an indication of a structural anomaly event proximal the location depending on the characterisation;
wherein the structural anomaly event includes an occurrence and/or further development of a structural anomaly.

According to still another aspect of an embodiment of the present disclosure there is provided an apparatus for processing a data signal obtained from a sensor sensing a dynamic signal including signal components attributable to fluid flow at a location within an operational pipeline network, the apparatus including:

means for processing the data signal to extract one or more features;
means for characterising the one or more extracted features; and
means for detecting an indication of a structural anomaly event proximal the location depending on the characterisation;

wherein the structural anomaly event includes an occurrence and/or further development of a structural anomaly.

Yet another aspect of an embodiment of the disclosure provides a computer-readable storage device storing instructions that, when executed by a processor, cause the processor to perform operations comprising:

obtaining a data signal from a sensor sensing a dynamic signal including signal components attributable to fluid flow at a location within an operational pipeline network:

processing the data signal to extract one or more features;

characterising the one or more extracted features; and detecting an indication of a structural anomaly event proximal the location depending on the characterisation;

wherein the structural anomaly event includes an occurrence and/or further development of a structural anomaly.

GENERAL DESCRIPTION

Embodiments of the present disclosure may provide systems and methods for collecting, transmitting and analysing a data signal so as to extract amplitude and/or frequency related features of a data signal attributable to vibro-acoustic energy associated with the occurrence and/or further development of a structural anomaly within an operational pipeline network, such as noise from a damaged pipe(s). Extracted features may then be characterised to assist with facilitating rapid detection and determination of the location of a cracked or damaged pressurized pipe(s) in a network. In one example, characterising feature, such as magnitude and/or frequency features, of the data signal attributable to the vibro-acoustic energy from a damaged pipe(s) involves analysing changes in these features.

In some embodiments, a system according to the present disclosure includes a spatial deployment of sensing units, such as sensing units comprising sensors and data acquisition units, located along pipes of the pipeline network to detect and measure features of the vibro-acoustic energy of acoustic waves travelling in pipe walls, contained media and/or surrounding media from damaged or cracked pipe sections. The or each sensor of a sensing unit may be deployed on the outside of the pipe, on pipe walls, on pipe fittings and/or inside pipes. Multiple sensors may be used to identify vibro-acoustic energy with different features and emanating from different sources (including damaged or cracked pipes and other environmental sources) and travelling in either the pipe wall, ground, air or media contained within the pipe. Examples of suitable sensors include microphones, accelerometers, hydrophones and pressure transducers.

Vibro-acoustic energy may arise from a number of sources including, but not limited to:

the flow of the fluid through the pipeline network including the interaction of the liquid with various components of the pipeline, eg pipe wall, valves, distribution points, water meters etc;

the interaction of fluid flowing through the pipeline network with any structural anomaly such as a crack/leak event resulting in additional flows of fluid departing the network; or other sources of acoustic energy eg., general environmental noise such as traffic, plant equipment, night clubs, tram operation, bus operation, train operation, functions, excavation work, construction site activities, concerts, car races and industrial water use.

A data signal including magnitude and/or frequency data attributable to vibro-acoustic energy associated with the occurrence and/or further development of a structural anomaly within an operational pipeline network may be collected by the sensors at different sampling rates and frequencies. In some embodiments, the magnitude and/or frequency data may be sampled over adjustable recording periods and at different time intervals. Sensing units may include data acquisition units which are with one or more sensors to facilitate local data processing at different levels and selectable and/or trainable event recording characteristics including recording setting changes when threshold conditions are met.

The magnitude and/or frequency data may be transmitted by the sensing units incorporating one or more sensors via, for example, radio, cell phone (GSM) and/or physical fibre communication systems at varying rates from, for example, once per day to, for example, every five minutes, or continuously, depending on the type of data collected and whether threshold conditions have been met requiring the transmission of data from the sensors.

In some embodiments, instructions to change a method of data recording may be sent to the sensing units via a communications system.

In some embodiments, "environmental" noise cancellation is conducted locally at a or each sensing unit or after the transmission and conditioning of the data using information from the or each sensing unit. Methods for processing a data signal to remove "environmental" noise are described in Australian Provisional Patent Application titled "METHOD AND SYSTEM FOR DETECTING A STRUCTURAL ANOMALY IN A PIPELINE NETWORK" filed on 24 Apr. 2019 in the name of the present Applicants.

Data may be stored via various electronic means, including cloud and servers, and can be visualized through a range of software platforms but the functioning of the described system does not depend on this.

Stored magnitude and/or frequency data may be analyzed using various mathematical/computational implementations. These mathematical/computational implementations may include change detection algorithms (for example, cumulative sum (CUSUM), Kalman filtering and mean and standard deviation) to identify changes in the magnitude and/or frequency data that relates to detected occurrence and/or further development of a structural anomaly within an operational pipeline network, such as a damaged or cracked pipe sections. Customised algorithmic relationships and parameters may be used to establish the detection performance of the algorithms and balance correct detections of damaged or cracked pipe sections with false detections. This customization may relate to physical factors at specific locations as well as more general mathematical/computational parameters used in each change detection algorithm.

The data may be normalized and the time record for the data divided into a number of window frames (selectable) with different window frame overlaps (selectable). This may involve processing data recorded and transmitted at system defined time intervals (minutes, hours, days or weeks) over a period (selectable) giving rise to datasets.

In an embodiment, the frequency data may be processed to identify changes in the frequency content of a data signal in terms of the amount of vibro-acoustic energy within particular frequency bands.

In some embodiments, a Power Spectrum Density (PSD) for each window frame (for a particular sensor (location along a pipe)) may be calculated and the median frequency for this frame's PSD is calculated to provide a median frequency value (ie. the frequency that divides the power across the frequency bins into halves) for each frame across the datasets.

In some embodiments, a peak value in each frame for each dataset may be identified and frames with normalized peaks greater than a threshold value considered contaminated by strong environmental noise and discarded.

In still other embodiments, a median frequency of the PSDs and a Root Mean Square (RMS) value for each frame within a dataset may be determined. In one example, a L90 (selectable) median frequency and a L90 RMS value is identified across all frames within a dataset. An increase in the L90 median frequency can be indicative of a new or developing structural anomaly, such as a leak or crack. An increase in the L90 RMS at the same time can be indicative of an energy increase due to a new leak or crack. These indicators may be used together.

Processing the magnitude and/or frequency data may involve processing data sets received at system defined intervals to extract sequences of frequency and/or RMS values for processing by change detection algorithms to identify changes in, for example, the frequency content of the acoustic signals, in terms of the amount of vibro-acoustic energy within particular frequency bands and changes in that energy (at a point in time), which are related to the noise from damaged or cracked pipes.

Varying amounts of historical data from hours to days to weeks may be used to establish baselines from which change detection can be performed and non-overlapping and overlapping frame sizes are selectable, together with thresholds, within the algorithms. Artificial neural network (ANN) and/or recurrent neural networks (RNN) algorithms may be used to establish baselines from which change detection can be performed.

Various change detection and learning algorithms may be applied to the magnitude and frequency data, with options for baseline period selection, variable change detection window sizes, threshold setting and customised operational parameters for the algorithms to achieve the maximum number of successful damaged and cracked pipe section detections and minimum number of false alerts.

Machine learning characterisation and detection may be applied for characterisation and/or detection. Embodiments which employ machine learning characterisation and detection may include statistical checks which are applied to a data signal or features extracted from a data signal. In certain embodiments, machine learning techniques using decision tree, support vector machines and/or CNN may be applied.

Patterns and characteristics of environmental noise, including comparisons of data received by all sensing units deployed at a location, may be able to be either actively identified and processed by the local data acquisition unit associated with the sensing unit and/or post processed to be removed (or accounted for) before undertaking analysis using the change detection and/or learning algorithms. Methods for processing a data signal to remove "environmental" noise are described in Australian Provisional Patent Application titled "METHOD AND SYSTEM FOR DETECTING A STRUCTURAL ANOMALY IN A PIPELINE NETWORK" filed on 24 Apr. 2019 in the name of the present Applicants.

The results from the change detection and/or learning analysis using multiple algorithms may be able to be combined to determine an overall likelihood or confidence associated with a change detection.

Characteristics of changes in features of the magnitude and/or frequency may be able to be used to identify the likely type of structural anomaly (eg. pipe damage and/or crack type). For example, the location of a predicted damaged or cracked pipe section may be identified as the location of the sensing unit providing the greatest recorded magnitude with other sensing units that detect the change in magnitude used to further refine the location of the predicted damaged or cracked pipe section based on the relative acoustic magnitudes and propagation pathways between the sensors.

BRIEF DESCRIPTION OF THE DRAWINGS

Embodiments of the present invention will be discussed with reference to the accompanying drawings wherein:

FIG. 7A is an example data structure of a segment of a data signal for processing by an embodiment of the disclosure;

FIG. 7B is an example frame structure for the segment shown in FIG. 7A;

FIG. 12A is a functional block diagram of a method of processing a sensed signal data using rate of change techniques;

FIG. 25 depicts a functional block diagram including interfaces between ROC and ANN processing methods;

FIGS. 26 and 27 shows results obtained with an ANN prediction derived from a week model and a two-month model respectively;

FIG. 38A depicts example PSDs and corresponding visualisations for different non-leak/crack sources;

FIG. 41 shows a table listing example characterisations of features of a data signal for classifying a 'fault type' of a detected leak/crack event.

DESCRIPTION OF EMBODIMENTS

Figure 1:
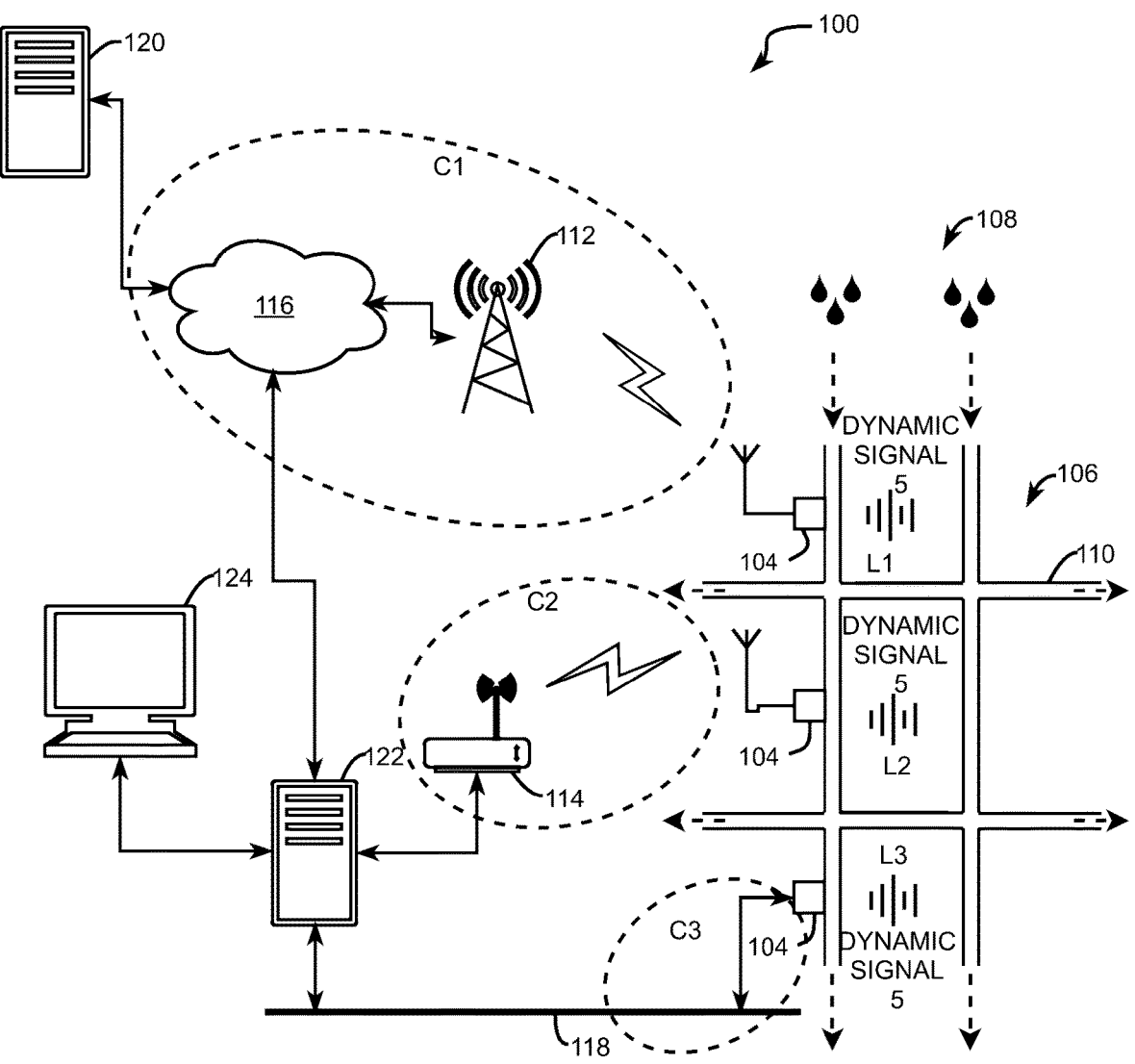
FIG. 1 is a block diagram of a system according to an embodiment of the present disclosure.

Referring initially to FIG. 1, there is shown a system 100 for processing a data signal derived or obtained from one or more sensing units 104 monitoring a dynamic signal 5 at a respective location (shown as L1, L2, L3) within an operational pipeline network 106. As will be described following, the depicted system 100 may comprise different example architectures for communicating and processing a sensed data signal to detect an indication of a structural anomaly event, such as occurrence and/or further development of a structural anomaly, proximal a respective one or more of the locations.

Before continuing further with a description of the system 100, it is to be understood that references to the term "operational pipeline network", where used throughout this specification, are to be understood to denote a pipeline network 106 which is operationally transporting a fluid or a gas using one or more pipes. A "pipe network", in this context, is to be understood as an interconnected arrangement of one or more pipes of the same or different pipe materials for transporting a fluid or a gas. Examples of pipe materials include metal (such as cast iron, ductile iron, mild steel, copper), ceramic, polymers, fibreglass and resin, reinforced concrete, prestressed concrete and cement materials.

In the description that follows, the operational pipeline network 106 will be described as a pipeline network for transporting and distributing water 108 (such as potable water) using a network of cast iron pipes 110. However, is to be appreciated that methods and systems of the present disclosure are not limited to water distribution pipeline networks nor to a network of cast iron pipes 106. Indeed, it is possible that embodiments of the disclosure may be applicable to other types of water pipeline networks, such as pipeline networks for transporting and/or distributing waste water, unprocessed water, salt (sea) water, river water, artesian water, spring water and irrigation water, as non-limiting examples. Furthermore, it is also possible that embodiments may be applicable for use with operational pipeline networks within an industrial environment, such as pipeline networks for transporting and/or distributing oil, gas, air, heating or cooling fluid, hydraulic fluid or lubricating fluid. Examples include, but are not limited to, petroleum refinery, storage and supply, processing factories, wine making and storage, minerals processing, gas supply networks, hot water heating supply networks, or airport fuel systems. It will thus be appreciated that although the following description refers to a water distribution pipeline network, methods and systems according to various embodiments of the present disclosure are not limited to a water distribution pipeline network 106 and thus may find application in processing sensed signal data to detect an indication of a structural anomaly event at or near a monitored location in various types of pipeline networks of different pipe materials.

Returning now to FIG. 1, system 100 is shown as including plural sensing units 104, communications infrastructure 112, 114, 116, 118, processing units 120, 122, and base station 124. Communications infrastructure could include one or more of local area network infrastructure (LAN) 114, wide area network (WAN) infrastructure 116/118, mobile communications data infrastructure 112, satellite communications infrastructure or the like. Suitable communications infrastructure would be well understood to a skilled person.

It is to be noted that whilst system 100 is depicted as providing plural types of data communication channels C1, C2, C3 for data communication between the one or more sensing units 104 at locations L1, L2, and L3 respectively and one or more of the processing units 120, 122, it is not essential that plural types of data communication channels be provided. It will be appreciated that a number of different types of data communication channels may be suitable and that the type(s) and configuration of the or each data communication channel will depend on the communication capabilities of the sensing unit 104 and the communication requirements and implementation considerations arising from that. In the present case, to assist with the discussion that follows, three examples of sensing units 104 are shown at L1, L2, L3 respectively, with each sensing units 104 having different data communication requirements for data communication via a respective channel C1, C2, C3.

In the present case the plural sensing units 104 are spatially located across the pipeline network 108. Each sensing units 104 includes one or more sensors for sensing a dynamic signal 5 including signal components attributable to fluid flow at or near each respective monitored location (L1, L2 and L3). In embodiments, the spatial location of the or each sensing unit 104 may be set, or otherwise determined and/or varied according to different criteria. Suitable criteria include, but are not limited to, critical pipe distribution, pipe materials, pipe main break distribution information, critical customer travel and transport routes and other utility criticalities.

As will be described in more detail following, embodiments including plural sensing units 104 spatially located across the pipeline network 102, such as the embodiment shown as system 100, may provide for improved spatial localisation, investigation and repair of indicated structural anomalies. Such improvements may arise as a result of the data signal from the separately located sensing units 104 including information which may assist with positionally and/or directionally locating a structural anomaly relative to the acoustic sensor of each sensing unit 104.

Although system 100 is depicted as including plural sensing units 104, it will of course be appreciated that it is not essential that the system 100 include plural sensing units 104 since, in some embodiments, it is possible that a single sensing unit 104 is provided to sense a dynamic signal 5 including signal components attributable to fluid flow at a single monitored location of the operational pipeline network 106 for detecting an indication of a structural anomaly event proximal thereto. Nevertheless, it is preferred that plural sensing units 104 be provided to provide improved positional and/or directional locating of a structural anomaly.

In the present case, each sensing unit 104 is configured to sense a dynamic signal 5 including signal components which are attributable to vibro-acoustic energy caused by fluid flow at or near the respective monitored location, at the least, so as to generate a respective data signal. In this respect, in this specification references to a "dynamic signal" are to be understood to denote a time-varying signal including signal components attributable to the vibro-acoustic energy of fluid flowing within a pipe of the water distribution pipeline network 102, at the least. The time-varying signal components may include, for example, amplitude and/or frequency components of the "dynamic signal". A dynamic signal will thus have amplitude related features and frequency related features. A non-limiting example of a "dynamic signal" is an acoustic signal, such as noise, acoustic pressure waves and acoustic vibration waves.

Figure 2:
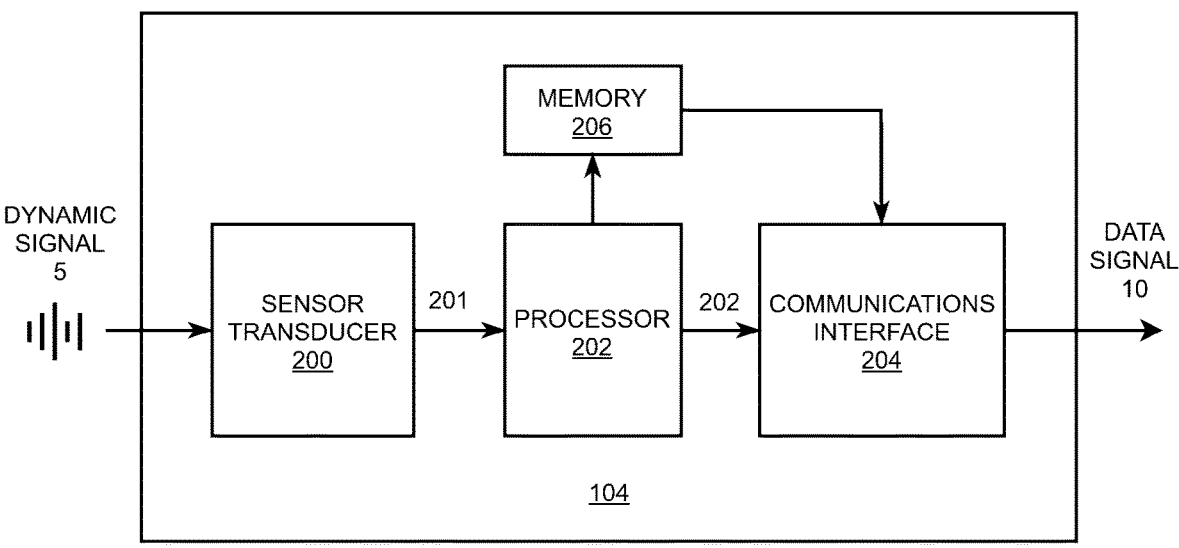
FIG. 2 is a block diagram illustrating one configuration of a sensing unit suitable for use with the system shown in FIG. 1.

The dynamic signal 5, and thus the sensed data signal 10 (ref. FIG. 2) obtained or derived therefrom, may also include signal components attributable to noise and vibration generated from other sources of vibro-acoustic energy, such as "environmental noise". The nature and significance of components of the data signal attributable to other sources of noise and vibration will vary according to the location and positioning of the monitored location and the sources of incoherent noise and vibration. By way of example, for a water pipeline network, other sources of noise and vibration may include road traffic noise and vibration, construction noise and vibration, network maintenance activity noise and vibration, and network operational noise and vibration (such as noise and vibrations from water meters, valve operation and the like).

In relation to the noise and vibrations attributable to vibro-acoustic energy caused by fluid flow at or near the respective monitored location, where fluid flow is disrupted or modified by a structural anomaly which creates a "leak" (such as a crack, joint, hole or any other defect), at least some of the signal components of the sensed dynamic signal 5 attributable to such noise and vibrations may include noise and vibrations arising from the fluid contained within the pipe discharging through the breakage, such as noise arising from an acoustic wave radiating from the leak location. Noise attributable to an acoustic wave radiating from the leak location of this type may be detected by sensors located within the pipe, or in contact with the pipe, or proximal to the pipe. For example, it is possible that noise attributable to an acoustic wave radiating from the leak location be detected by a sensor located within a medium supporting the pipe, such as a soil medium.

Depending on the type of sensor employed by a sensing unit 104 to sense a dynamic signal 5 including coherent noise and vibrations arising from an acoustic wave radiating from the leak location, the sensor may be positioned internally within a pipe (that is, within the contained fluid), on or near fittings in mechanical communication with the pipe, or on or in surrounding physical elements (such as the soil or other medium in which the pipe is located). Examples of suitable sensor types include accelerometers, hydrophones, microphones, pressure transducers, optical sensors, and strain gauges. However, it is to be appreciated that any sensor suitable for sensing a dynamic signal 5 including components attributable to an acoustic wave radiating from the leak location may be used.

Irrespective of the type of sensing unit 104, each sensing unit 104 provides a data signal 10 in the form of an analog or digital domain representation of the respective sensed dynamic signal 5 for processing.

Providing the data signal 10 may involve one or more signal conversion and/or conditioning operations. In a typical case, for example, a sensing unit 104 will be configured to convert a sensed dynamic signal 5 to a digital signal, such that the signal conversion operations will include analog-to-digital (A/D) conversion. Examples of signal conditioning operations that may be performed on the sensed dynamic signal 5 include analog and/or digital domain bandpass filtering (e.g., low-pass filtering). For example, the or each sensing unit 104 may include in-built high-pass filter, such as a high-pass filter having a cut-off frequency of 30 Hz, and an in-built anti-aliasing filter. Particular cut-off frequencies may depend on the pipe material.

Turning now to FIG. 2, there is shown a simplified block diagram of a sensing unit 104 suitable for use with an embodiment shown in FIG. 1. As shown, the sensing unit 104 includes a sensor transducer 200, processor 202, communications interface 204 and memory 206. Sensor transducer 200 may include any transducer having a dynamic range suitable for sensing the dynamic signal 5. As indicated above, suitable sensor transducers include accelerometers, strain gauges, pressure transducers, optical sensors, hydrophones, and microphones. Memory 206 may store a set of executable program instructions for execution by the processor 202 and include registers for storing data for processing and communication. A sensing unit 104 suitable for used with an embodiment is disclosed in "METHOD AND SYSTEM FOR DETECTING A STRUCTURAL ANOMALY IN A PIPELINE NETWORK" filed on 24 Apr. 2019 in the name of the present Applicants.

In the sensing unit 104 depicted in FIG. 2, processor 202 performs the above described signal conditioning and pre-processing operations on sensor output signal 201 to provide output data 202 for output communication by communications interface 204. Communications interface 204 may include a suitable wired or a wireless data communications interface. Non-limiting examples of suitable wired data communications interfaces include Ethernet, RS-232, RS-485, UART, USART, USB compatible communications interfaces. Non-limiting examples of suitable wireless data communications interfaces include Bluetooth® (IEEE 802.15.1), Zigbee® (IEEE 802.15.4), IEEE 802.11 (Wi-Fi), 3G, WiMax®, Mobile WiMAX®, 3G (ie. LTE), 4G (LTE-A), and 5G compatible communications interfaces. It is also possible that communications interface 204 may support connectivity to a satellite-based communication device.

In some embodiments, output data 202 includes the data signal 10 for output data communication to an external processing unit (such as processors 120, 122 shown in FIG. 1) via suitable communications infrastructure (such as C1, C2, or C3 shown in FIG. 1) for processing thereby to extract one or more features of the data signal 10 for detecting an indication of a structural anomaly event.

The data signal 10 may include a continuous real-time signal, or it may include segmented data in the form of a series or set of data segments including time-limited periodic samples of the dynamic signal 5.

For example, in an embodiment, processor 202 periodically acquires a segment of a sensed signal 201 from transducer 200 to generate the data signal 202 as a sequence of wave files (such as a .wav file), with each wave file including a digital domain representation of a respective segment of sensed signal 201. For example, processor 202 may use a sampling rate of about 5 kHz to sample a 10 second segment of sensed signal 201 at 10 minute intervals. Other sampling rates and sample intervals may be used. For example, a sampling rate in the range of 256 Hz to 10 kHz may be suitable. Each resultant 10 second wave file is then communicated to, for example, an external processor, such as processor 122 (ref. FIG. 1) via a suitable data communications channel for further signal processing to extract one or more features of each segment and thus the data signal 10.

In other embodiments, it is possible that processor 202 locally processes sensed signal 201 for local processing to detect an indication of a structural anomaly event. In such embodiments, it is possible that processor 202 may generate the data signal 202 to encode a detection event for communication to a remote monitoring station (such as station 124 shown in FIG. 1) via communications interface 204, and an appropriate data communication channel.

Figure 3:
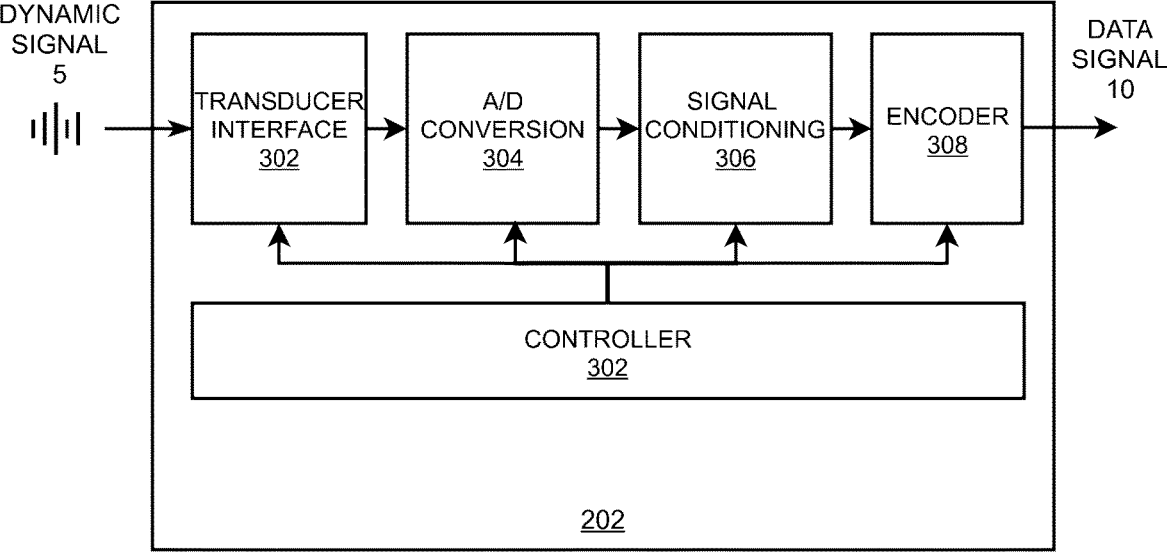
FIG. 3 is a block diagram illustrating one configuration of a processor suitable for incorporating in the sensing unit shown in FIG. 2.

In some embodiments, a signal energy level threshold may be configured locally at each sensing unit 104 such that exceedance of the threshold may trigger an ad-hoc data transmission of data 202 encoding a detection event. Techniques for processing sensed signal data to obtain an indication of a structural anomaly event within an operational pipeline network will be described following. Turning now to FIG. 3 there is shown a block diagram of an example processor 202. In the illustrated example, processor 202 includes a transducer interface 302, A/D conversion 304, signal conditioning 306, encoder 308 and controller 302. Controller 302 may include software or firmware for controlling the operation of the processor 202.

Figure 4:
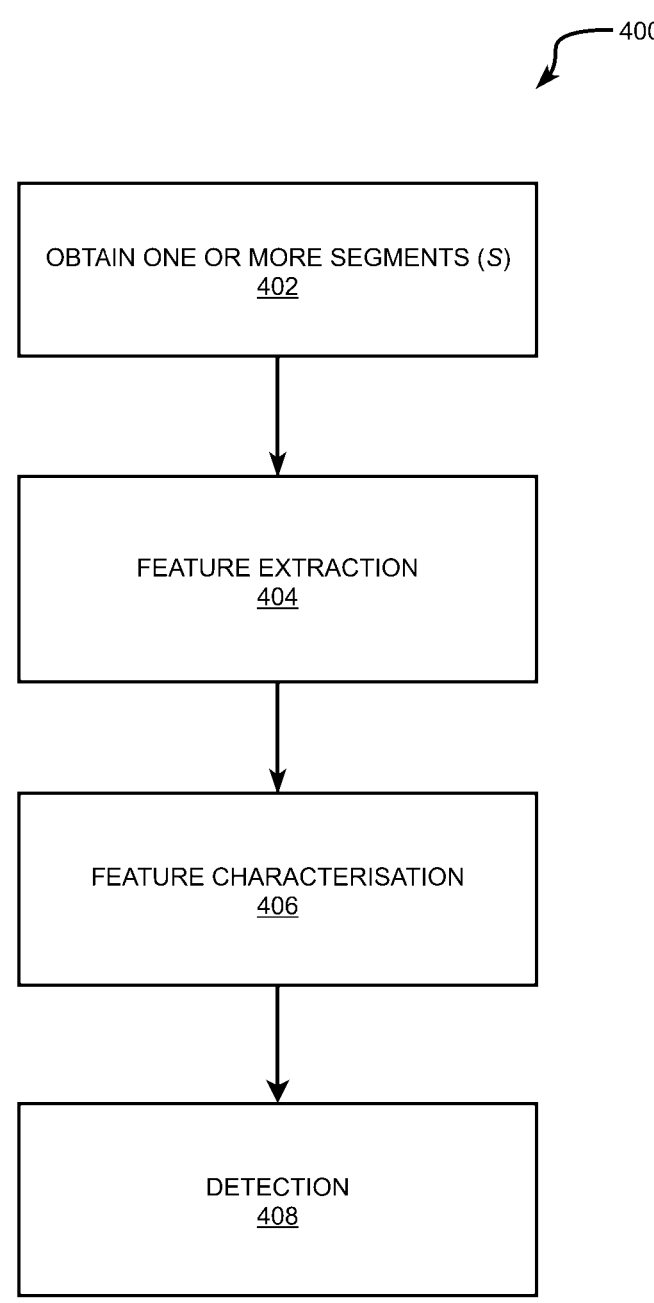
FIG. 4 is a flow diagram of a method of processing a data signal according to an embodiment of the disclosure.

FIG. 4 is a flow chart illustrating an embodiment of a method 400 of processing a data derived signal obtained from a sensing unit 104 a location within an operational pipeline network 106.

Initially, a processor, such as the processor 122 shown in FIG. 1, obtains at step 402 one more data segments S including signal data for the dynamic data signal 10 obtained from one or more sensing units 104. Once so obtained, the or each segment S is processed at step 404 to extract one or more features of the or each segment S, and thus of the data signal 10. The one or more extracted features are then characterised at step 406. An indication of a structural anomaly event may be detected proximal the location depending on the characterisation.

As will be described following, extracting one or more features of the data signal 10 and characterising the one or more extracted features to detect an indication of a structural anomaly event proximal the location depending on the characterisation may involve different techniques. Examples of suitable techniques for processing a data signal 10 to extract and characterise one or more features thereof to detect an indication of a structural anomaly event proximal the location depending on the characterisation will now be presented.

Example 1

Magnitude, Frequency and/or RMS Signal Feature Extraction and Characterisation

Figure 5:
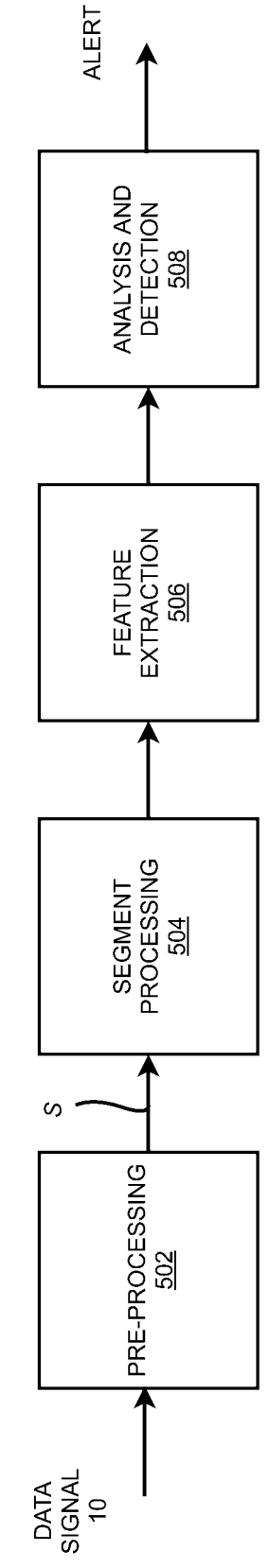
FIG. 5 is a top-level functional block diagram of a system for processing sensed signal data according to an embodiment of the disclosure.
Figure 6:
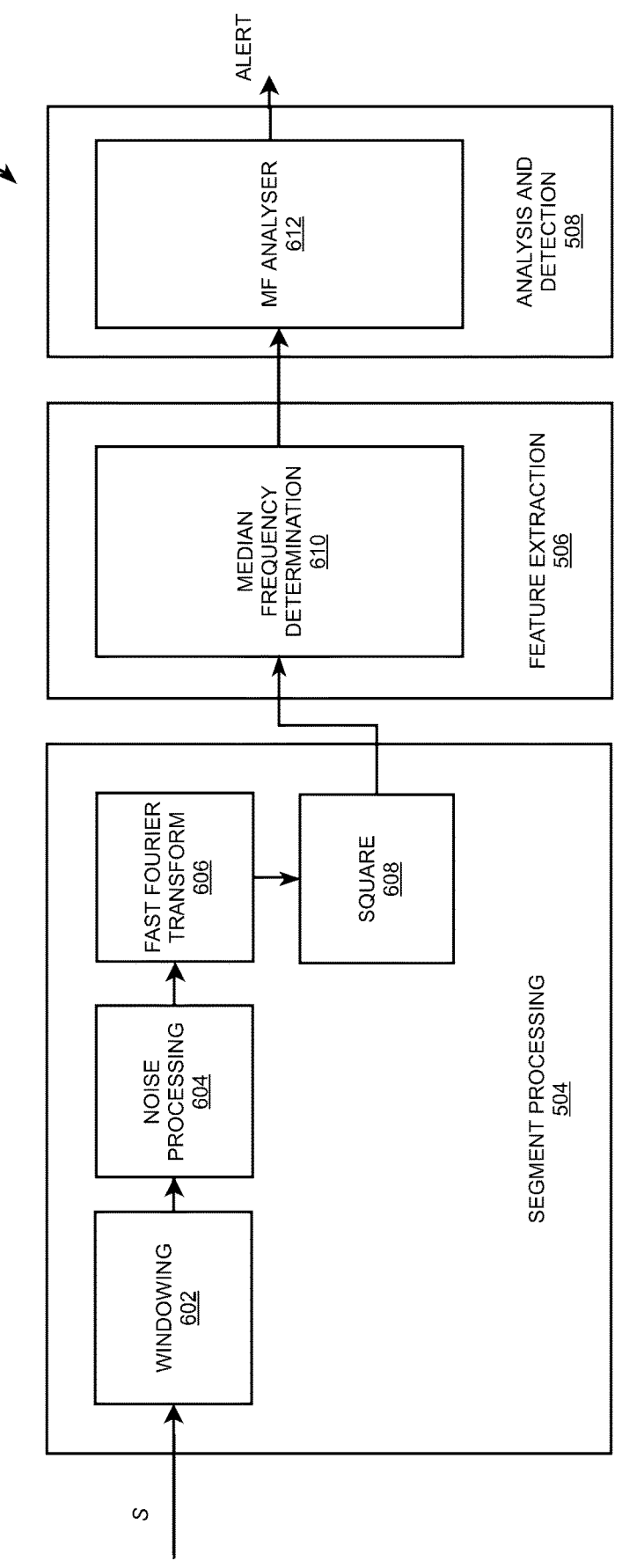
FIG. 6 is another functional block diagram of a system for processing a data signal according to an embodiment of the disclosure.

FIGS. 5 and 6 show functional block diagrams of operational schema 500 for one embodiment of a method of processing a data signal 10 from a sensing unit 104 to extract one or more features of the data signal 10 and thus of the dynamic signal 5. The one or more extracted features are then characterised and, depending on the characterisation, an indication of a structural anomaly event proximal the location of the sensing unit 104 may be detected, wherein the structural anomaly event includes an occurrence and/or further development of a structural anomaly.

Figure 8:
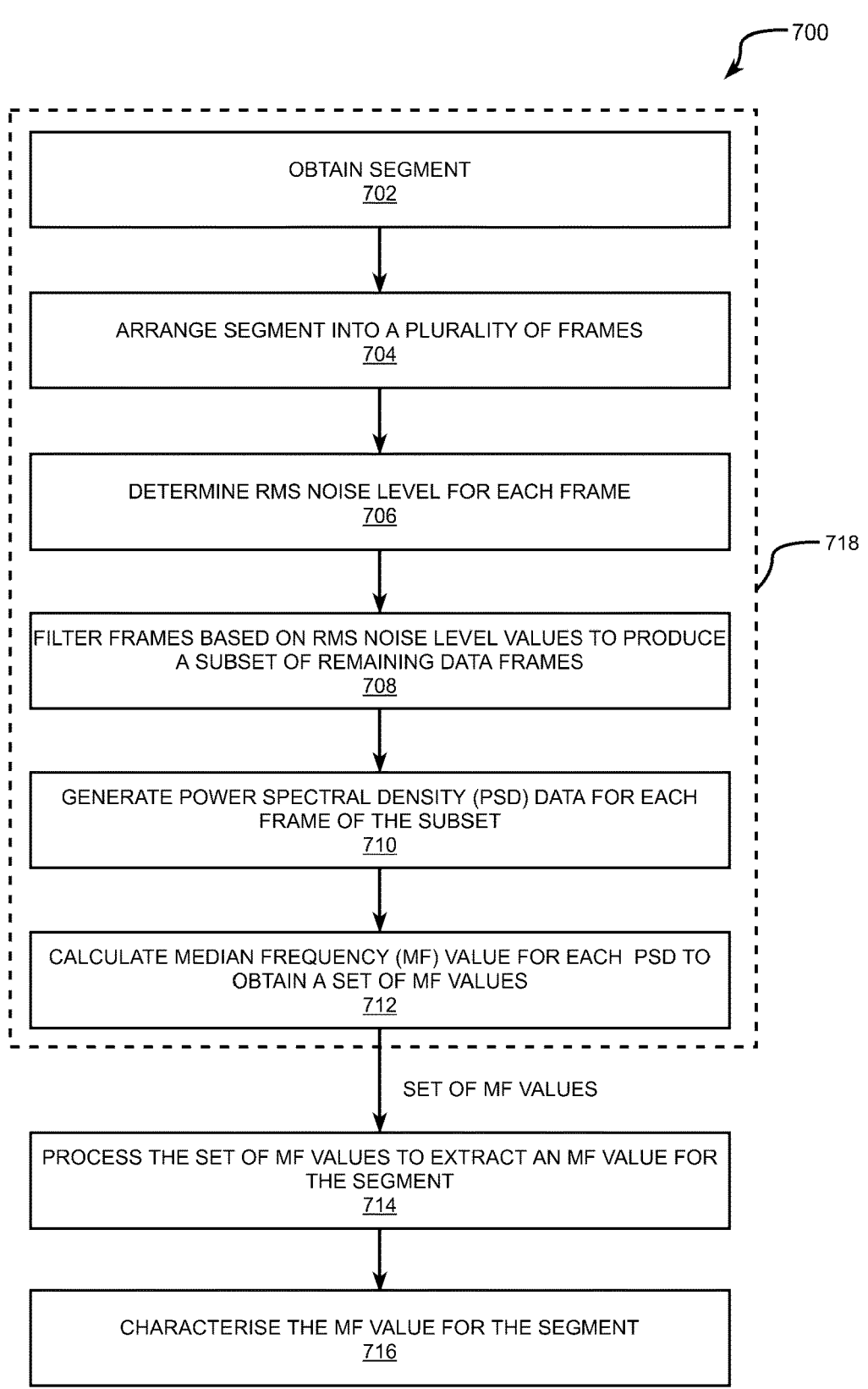
FIG. 8 is a flow diagram of an embodiment of a method of processing a data signal using the system shown in FIG. 6.

In the description below, the schema 500 shown in FIGS. 5 and 6 will be described with reference to the flow diagram shown in FIG. 8.

With reference initially to FIG. 5, the schema 500 includes a pre-processing block 502, segment processing block 504, feature extraction block 506, and analysis and detection block 508.

Pre-processing block 502, obtains at step 702 (ref. FIG. 8), for processing by the system 500, one more data segment S of the data signal 10 (hereinafter the 'data signal'). In embodiments, each segment S includes data corresponding to a time-limited sample of the data signal 10 obtained at a particular sample time t. For example, in embodiments, the or each segment S may include a 10 second sample of the data signal 10 obtained at a predetermined interval, such as days, hours, minutes or seconds (eg. once a day or every 90 minutes).

Segment S may have any suitable data format. One example data structure for S is shown in FIG. 7A. In the illustrated embodiment, segment S is in the form of a wave file in UINT8 data (d) type (unsigned integer stored with 8-bits, having a minimum possible value of 0 and a maximum possible value of 255). It will be appreciated that other file types and indeed other data formats may be used.

In one particular example, the wave file is recorded as a file having a sampling rate of 4681 Hz and an approximate duration ($t_{DUR}$) of 10 seconds to provide (N) 46,786 data points ($d_x$), In this example, obtaining a data signal 10 by the pre-processing block 502 involves converting the UINT8 data segments S of data signal 10 into double precision values which are then normalised so as to have a minimum possible value of −1 and a maximum possible valve of +1. Normalisation normalises the sensed signal data relative to a maximum possible dynamic range of the sensor transducer 200 of the sensing unit 104 (ref. FIG. 2) from which the data signal 10 was obtained. For example, if the output of a sensing unit 104 has a minimum possible value of $x_{lim\_min}$ and a maximum possible value of $x_{lim\_max}$, normalisation could be performed using Equation (1).

$$\tilde{x} = \frac{2(x - x_{lim\_min})}{x_{lim\_max} - x_{lim\_min}} - 1$$ Equation (1)

where x is the original measurement of the dynamic response, and $\tilde{x}$ is the normalised data with a minimum possible value of −1 and a maximum possible value of 1.

In the present case, pre-processing block 502 also includes a filter, such as a high-pass filter having a cut-off frequency and an in-built anti-aliasing filter. In an embodiment, the pre-processing block 502 includes a high-pass filter having a cut-off frequency of 30 Hz. However, it will be appreciated that the type and configuration of the filter may vary according to implementation considerations.

Turning now to FIG. 6, in certain embodiments segment processing block 504 includes a windowing process 602, noise processing process 604, fast Fourier transform process 606 and square process 608.

Windowing process 602 arranges, at step 704 (ref. FIG. 8), the or each segment S into a set of one or more time-domain data frames $\{a_1, a_2, \ldots a_n\}$ (hereinafter 'data frames') (ref. FIG. 7B) for further processing by transform block 504 using fast Fourier transform (FFT) techniques. Data frames may be formed as overlapping (ie. with adjacent segments overlapping by an overlapping ratio) or non-overlapping frames. In one particular example, and as is shown in FIG. 7B, the set of data frames $A=\{a_1, a_2, \ldots a_n\}$ is formed using a sliding rectangular window having a data length of 256 (ie. each window has a duration of approximately 55 ms using a sampling rate of 4681 Hz) with an overlapping ratio of 80%.

In certain cases, at least some of the data frames of the set $A=\{a_1, a_2, \ldots a_n\}$ will include data which has been contaminated by vibro-acoustic energy from non-leak/crack sources, such as traffic noise, water meter ticking noise or other sources of incoherent noise. In a particular example, data frames having features which may indicate that the data frame includes data which has been significantly contaminated by such noise may be attenuated or removed prior to further processing by any suitable technique. In the illustrated embodiment, noise processing process 604 attenuates or removes, from the set of data frames A, data frames (a) having features which may indicate, for example, that the data frame(s) includes data which has been contaminated by vibro-acoustic energy from non-leak/crack sources, such as environmental sources using a suitable noise processing technique.

One example of a suitable technique includes setting a signal threshold value such that any data frames having a peak signal value which exceeds the signal threshold value are taken to have been contaminated by incoherent noise and are removed before any following analysis. For example, a signal threshold value may be selected as 0.95 (for normalised data that has a possible maximum of 1). It will of course be appreciated that other signal threshold values may be used. In this respect, lowering the threshold for the peak-based pre-processing may remove more contaminated data frames. However, this may also increase the risk of removing useful data.

Another example of a suitable technique for attenuating or removing data frames having features which may indicate that the data frame includes data which has been contaminated, includes determining, at step 706, (ref. FIG. 8) an RMS value for each data frame to provide a set of RMS values associated with the segment S of the data signal 10. In this respect, the RMS of a data frame may be determined using Equation (2).

$$RMS = \sqrt{\frac{1}{N} \sum_{i=1}^{N} x_i^2}$$ Equation (2)

where N is the total number of data points within a data frame a, and $x_i$ is the value of the $i_{th}$ data point of the data frame after normalisation.

In this example, data frames having an RMS value which exceed an RMS threshold value are removed from the set of data frames $A=\{a_1, a_2, a_3, \ldots, a_n\}$ to thereby provide a subset of data frames B formed, at step 708, according to the RMS threshold value. One example of a RMS threshold value is the RMS value which 5% of the RMS values for the data frames exceed. Other threshold values may also be suitable.

Having constructed a subset B of data frames from which "noisy" frames may have been excluded, FFT process 606 transforms each data frame of the subset B into the frequency domain to generate, after square process 608, and at step 710, data (P₁, . . . Pₙ) representing the power spectral density (PSD) of each transformed remaining data frame(s) of the subset B.

Transforming each data frame of the subset B into a frequency domain representation comprising PSD data (P₁, . . . Pₙ) may involve applying a suitable tapering window function to each data frame of the subset B so as to enhance frequency resolution and reduce spectral leakage prior to applying the fast Fourier transform (FFT) process 606.

One example of a suitable tapering window function is a Hamming window defined by Equation (3).

$$w[n] = 0.54 - 0.46\cos\left(\frac{2\pi n}{N-1}\right) \qquad \text{Equation (3)}$$

where n is an integer from 0 to N–1, N is the total length (data points) of the window, w[n] is the $n_{th}$ value in the window. Applying a window to a segment S of data involves multiplying the window function with the data.

Suitable FFT 602 and square processes 608 for converting a time-domain data signal into a frequency domain signal data representing a PSD would be understood to a skilled person. A fast Fourier transform for data with discrete samples is defined by Equation (4).

$$P_k = \sum_{n=0}^{N-1} x_n e^{-j2\pi kn/N} \qquad \text{Equation (4)}$$

where N is the total length (data points) of the data to be transformed, $x_n$ (n=0, . . . , N–1) are the data in the time domain, $P_k$ (k=0, . . . , N–1) are the transformed results in the frequency domain, j is the imaginary unit.

Feature analysis and detection block 508 processes, at step 714, the PSD data (P₁, . . . Pₙ) for each respective data frame to determine a value of a statistical parameter, which in this example is a normalised median frequency (MF) value, using median frequency determination process 610 to thereby provide a set of normalised MF values. Before continuing further, although the following description describes the use of a normalised MF value, it is to be appreciated that other statistical parameters may be used, either separately or in combination with the MF value. For example, in relation to time-dependent features, it is possible that standard deviation, mean and percentile-based ranges could be used either separately or in combination with the MF value.

In the present case, the dimensional MF values are normalised with respect to the Nyquist frequency (ie. half of the sampling frequency) so as to provide normalised MF values in the range of 0 to 1. The MF value can be determined by finding the frequency bin which divides the PSD into two halves as shown in Equation (4).

$$\sum_{k=1}^{M} P_k = \frac{1}{2}\sum_{k=1}^{N} P_k \qquad \text{Equation (5)}$$

where $P_k$ is the PSD value at the kth frequency bin, N is the total number of frequency bins in a PSD, and M is the frequency bin that divides the PSD into two halves. The MF is the frequency corresponding to the $M_{th}$ frequency bin. The normalised MF is the MF divided by the Nyquist frequency, which is half of the sampling frequency.

Median frequency determination process 610 then processes at step 714 (ref. FIG. 8) the set of normalised MF values falling within a range or bound. In the present case, to achieve this, the set of normalised MF values are ranked from lowest to highest, so as to extract, as the feature of the data signal 10, an MF value for which 90% of the set normalised MF values exceeds. In the present example, the extracted MF value will be referred to as the "L90 MF value" indicator, meaning that 90% of the normalised MF values are higher than the L90 MF value. The extracted MF value is then assigned to the sensed signal data 10 as a feature.

Before proceeding further, although the below description describes the use of an L90 value, it is to be appreciated that the present disclosure is not intended to be so limited. In other words, in some embodiments, other LXX values (where XX is a two-digit number) may be extracted, such as L95, L85, L80, L75 as further non-limiting examples. Other LXX values may also be suitable.

Having extracted, for the data signal 10, a feature in the form of the L90 MF value, MF analyser 612 then characterises, at step 716, the L90 MF value for a segment (or a set of L90 MF values for plural segments S) of the data signal 10 to determine whether the data signal 10 includes an indication of a structural anomaly event proximal the location, depending on a characterisation of the L90 MF value or indeed on a characterisation a set of L90 MF values including a current L90 MF value.

In this respect, the applicants have found that an L90 MF value which can be characterised as having a persistent increase over time may indicate an occurrence and/or further development of a structural anomaly event, such as a new through-wall crack, in pipes proximal to a sensing unit 104. Accordingly, in one embodiment, L90 MF values for plural segments S of the signal data 10 sampled at different times are analysed to detect and/or recognise changes in the set of L90 MF values as indicating the occurrence and/or further development of a structural anomaly event. In one example, threshold L90 MF values may be set for automated alarm generation, with the selection of a threshold based on, for example, historical L90 MF values for a normal (ie. no-fault) condition at each sensing location, or indeed to classify a leak as being due to a particular crack type.

In another example, embodiments may process plural segments S of the data signal 10 obtained at a sampling interval such that S={S_t+S_{t+Δt}+S_{t+2Δt}+ . . . +S_{t+nΔt}} where Δt is the sampling interval, and apply statistical techniques, pattern recognition techniques, change detection techniques, digital filtering, or combinations thereof to a resultant set of L90 MF values characterising the data signal 10 to thereby detect an indication of a structural anomaly event proximal the location depending on the characterisation.

Although the above examples involves characterising either an extracted discrete L90 MF value or an extracted temporal set of L90 MF values to detect an indication of a structural anomaly event proximal the location depending on a characterisation of the L90 MF value or values, it may be desirable to determine other statistical indicators to validate and/or supplement an indication obtained from an L90 MF value. For example, in some embodiments it is possible that a suitable RMS value may extracted for the or each segment S and used either separately or in combination with the L90 MF value or values to values to detect an indication of a structural anomaly event. One example of a suitable RMS value is an L90 RMS value.

A discrete L90 RMS value for a single segment S of a data signal 10, or indeed a temporal set of L90 RMS values for a set of plural segments $S=\{S_t+S_{t+\Delta t}+S_{t+2\Delta t}+ \ldots +S_{t+n\Delta t}\}$ where $\Delta t$ is the sampling interval, of the data signal 10 may be determined using a similar approach to that described in relation to the L90 MF value above.

To determine an L90 RMS value for a single segment of a data signal 10, the data signal 10 is first conditioned via filter process 502 and windowing process 503. A RMS value is then determined for each of the resulted data frames using Equation (1) to obtain a set of RMS values. The set of RMS values are then ranked from lowest to highest, and a feature is extracted as an L90 RMS value for which 90% of the set RMS values exceeds. In this case, the L90 RMS value is the extracted feature for the data signal 10, and detection of an indication of a structural anomaly event proximal the location depends on its characterisation. For an L90 RMS value for a single segment of the data signal 10, characterisation of the L90 RMS value may involve characterising the L90 RMS values as exceeding a signal magnitude threshold, or falling with one or more ranges.

For a set of L90 RMS values obtained for plural segments S of the data signal 10, detection of an indication of a structural anomaly event proximal the location depending on the characterisation of the L90 RMS values may involve statistical techniques, pattern recognition techniques, CUSUM processing, digital filtering (such as Kalman filtering techniques), p-value, or combinations thereof, to the set of L90 RMS values to identify changes in the acoustic wave that relate to a damaged or crack pipe.

In a further example, a set of L90 RMS values and a set of L90 MF values may be extracted from a data set comprising a collection of segments collected at different times for a particular sensing location. The or each extracted set of determined L90 RMS and/or L90 MF values may then characterised so as to detect an indication of a structural anomaly event proximal the location depending on the characterisation. For example, a set of extracted L90 RMS and L90 MF values which can be characterised as having a persistent increase in the L90 RMS and L90 MF values may indicate the detection of an occurrence and/or further development of a structural anomaly event, such as a new through-wall crack, in the pipes surrounding the sensor or sensors of the sensing unit 104.

Figure 9A:
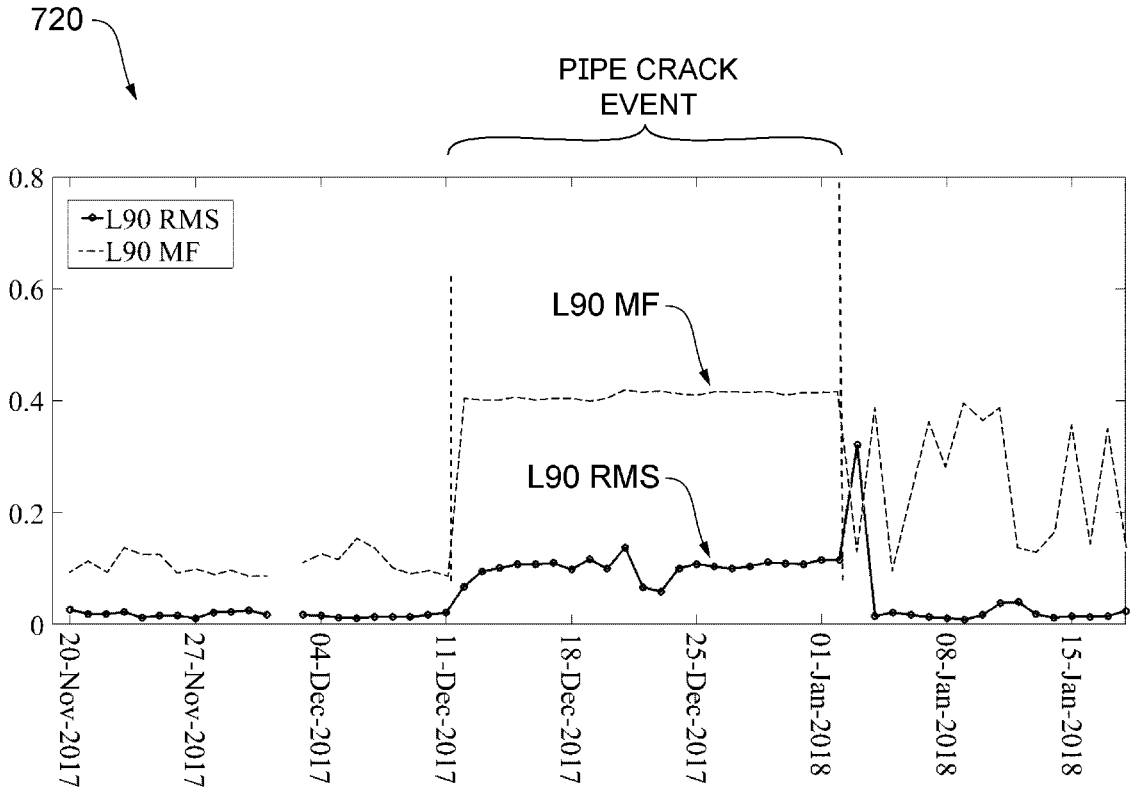
FIG. 9A is a plot diagram showing an example of a detection of a leak/crack event for a data signal.

FIG. 9A illustrates a plot 720 showing an example of a detection of a pipe crack structural anomaly event for a data signal 10. The horizontal axes of plot 720 illustrates sample dates during which segments were obtained. The vertical axes denotes a normalised L90 MF and L90 MF scale. Each L90 MF and L90 RMS plot is characterised as having an elevated response to a pipe crack structural anomaly event (from a circumferential crack on a water main) on about 12 Dec. 2017. As shown, the elevated values remained until on or about 5 Jan. 2018, after which the cracked pipe was repaired. As shown, prior to the pipe crack structural anomaly event, both the L90 MF and L90 RMS values were relatively low and stable. However, after the repair work, the L90 RMS went back to the original low level, but the L90 MF value showed instability between low and high readings on different days, generating irregular false positives. Further investigation of the wave files and the maintenance history indicated that the unstable L90 MF values were induced by poor physical contact between the relevant sensor of a sensing unit and a valve fitting in a chamber. As a result, it is possible that an unstable L90 MF characteristic may be used to detect or indicate a sensor malfunction.

Figure 9B:
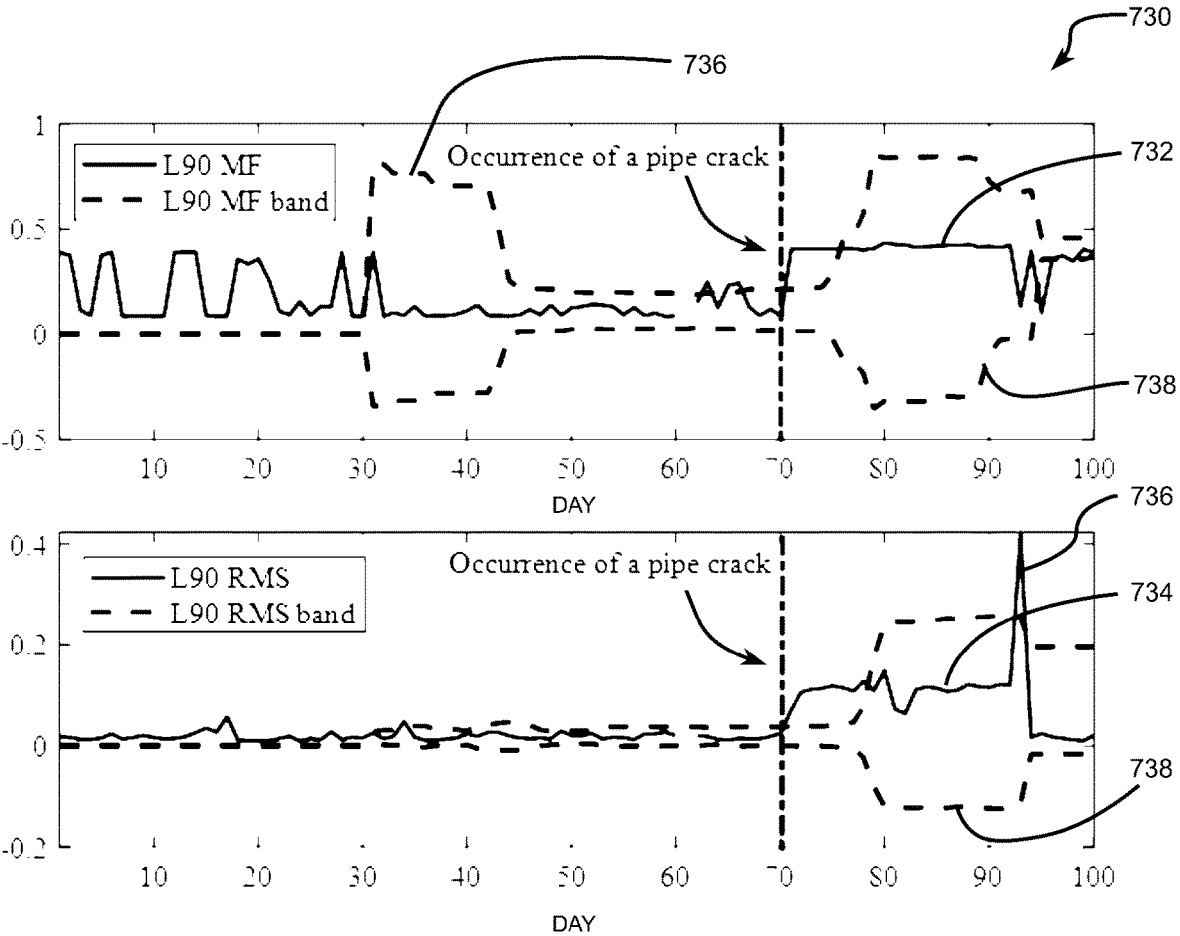
FIG. 9B is a pair of L90 MF and L90 RMS plot diagrams showing an example of a detection of a leak/crack event for a data signal.

FIG. 9B illustrates a pair of plots 730 showing an example of another technique for the detection of a leak/crack event characterised by an elevated L90 MF and the L90 RMS response (lowermost plot) to a pipe crack structural anomaly event in a period from about day 70 to about day 94 of a monitoring period for the same data signal used to construct FIG. 9A. In this example, plot 732 represents an extracted daily L90 MF value, plot 734 represents an extracted daily L90 RMS value, and plots 736, 738 represent respective upper and lower detection boundaries. In the present case, the upper 736 and lower 738 detection boundaries are determined from processing a rolling 30-day window of data signal 10. Hence, in the illustrated plots, the period from day 1 to 30 is a first 30-day period after which the detection boundaries 736, 738 become active. One example of a technique for calculating upper and lower detection boundaries will be described below with reference to Example 2 in the context of MF and RMS values. However, it will be appreciated that a similar technique to that disclosed in relation to Example 2 could be applied to determine upper and lower detection boundaries for L90 MF and L90 RMS values. In the example illustrated in FIG. 9B, a pipe leak/crack event is detected if the L90 MF daily and/or L90 RMS daily value exceeds the respective upper 736 detection boundary, as is indicated at about day 70.

The above examples relates to the application of statistical based characterisation of frequency and/or RMS signal features of a data signal which have been extracted using a process described. However, it is to be appreciated that other methods may be used to characterise the extracted features so to obtain indication of the occurrence, attributes and/or further development of a structural anomaly event within an operational pipeline network. Other suitable methods may involve, machine learning characterisation and detection techniques, pattern recognition techniques, CUSUM processing, digital filtering (such as Kalman filtering techniques), or combinations thereof, to identify, by characterising the frequency and/or RMS signal features of the data signal 10, changes in the acoustic wave that relate to a damaged or crack pipe.

Example 2

Predictive Frequency and/or RMS Signal Extraction and Characterisation

Figure 10:
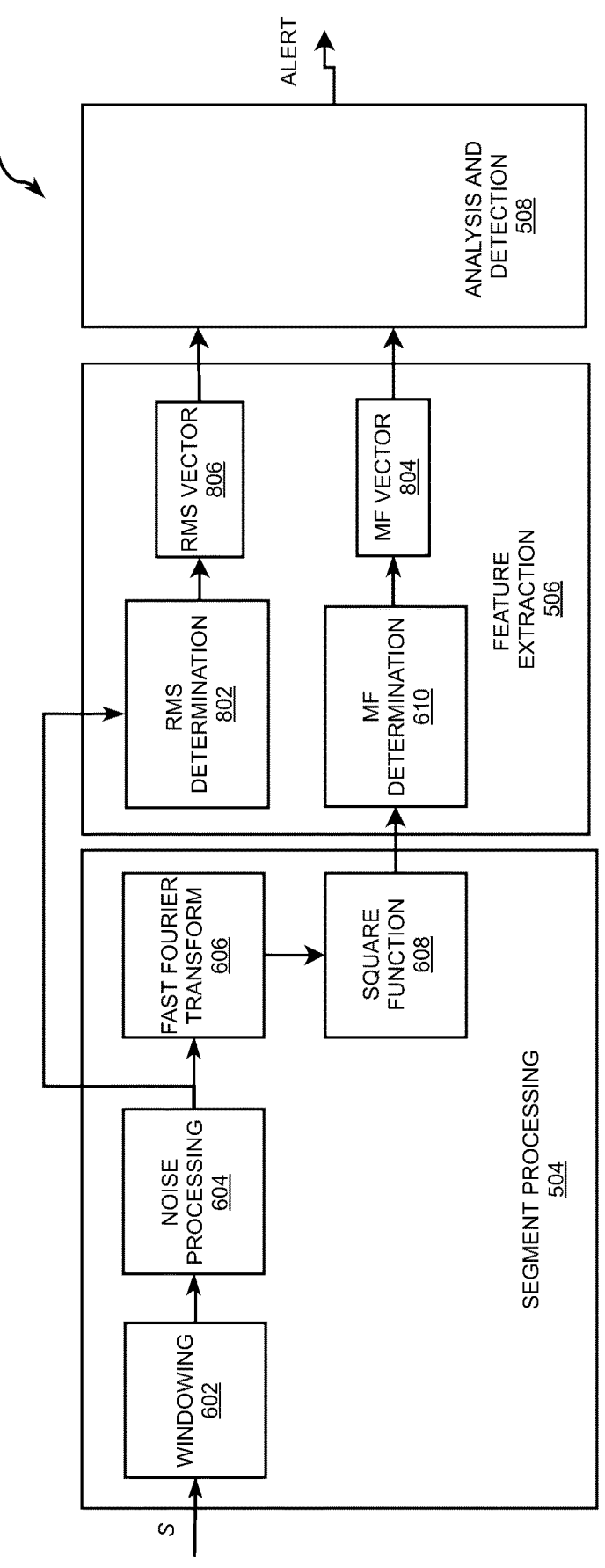
FIG. 10 is a functional block diagram of another system for processing a data signal according to an embodiment of the disclosure.
Figure 11A:
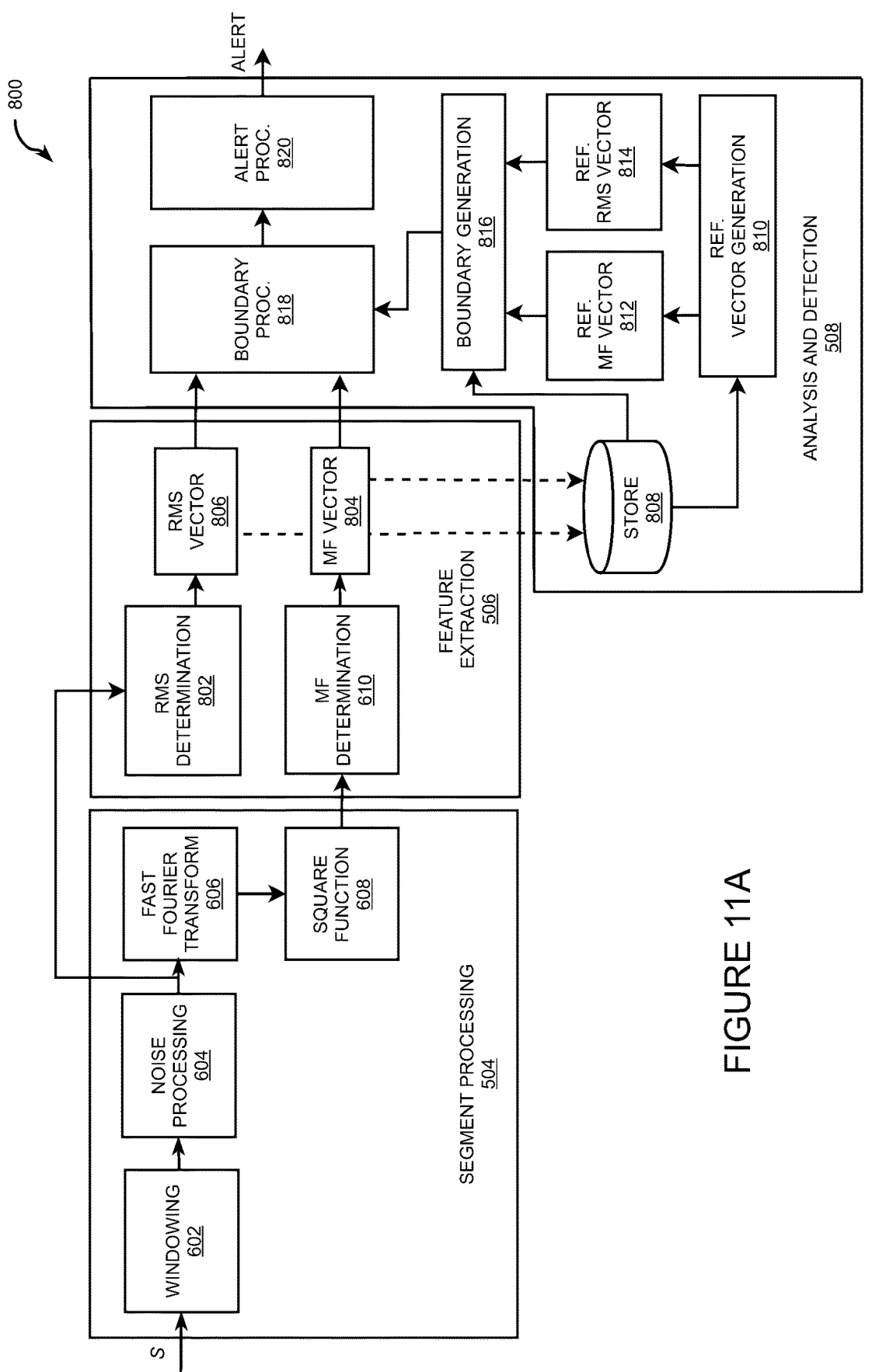
FIG. 11A is a functional block diagram of another system for processing a data signal according to an embodiment of the disclosure.

FIG. 10 shows a functional block diagram for another example of an operational schema 800 for processing one or more segments S of a data signal 10 to extract one or more features of the data signal 10 (and thus of the dynamic signal 5), characterising the one or more extracted features, and detecting an indication of a structural anomaly event proximal the location depending on the characterisation. FIG. 11A is a flow diagram of one embodiment of a method of processing sensed signal data using the operational schema 800 shown in FIG. 10.

As shown in FIG. 10, in the illustrated example, schema 800 includes the segment processing function 504 described above in relation to Example 1. However, as will be described below, the schema 800 depicted in FIG. 10 includes a different feature extraction function 506 configuration and thus a different analysis and detection function 508 configuration.

In this example, each segment of a set of plural segments $S=\{S_t+S_{t+\Delta t}+S_{t+2\Delta t}+\ldots+S_{t+n\Delta t}\}$ where $\Delta t$ is the sampling interval, are separately partitioned into a selectable number of frames (e.g., N=256 windows for a 10 second signal) by windowing process 602 using the windowing process described above with reference to FIGS. 7A and 7B. A PSD is then derived for each frame of each of the plural segments S using a similar process to that described above in relation to Example 1 and involving FFT process 606 and square process 608.

Feature extraction process 502 shown in FIG. 10, then determines a median frequency (MF) value of the PSD for each frame of a segment S using MF determination process 610 to obtain a set of MF values for a respective segment S for output as MF Vector 804. An RMS value for each frame is also derived using RMS determination process 802 using the same process as described above with reference to Equation 2 to provide RMS Vector 606.

The above described operations thus involve deriving a PSD for each frame of a segment S, and processing each derived PSD to determine a median frequency (MF) and an RMS value for each frame of the segment S, with each MF and RMS value determined for the frames of a segment then being stored in the corresponding MF Vector 804 or RMS Vector 806 for further processing by analysis and detection function 508.

Figure 11B:
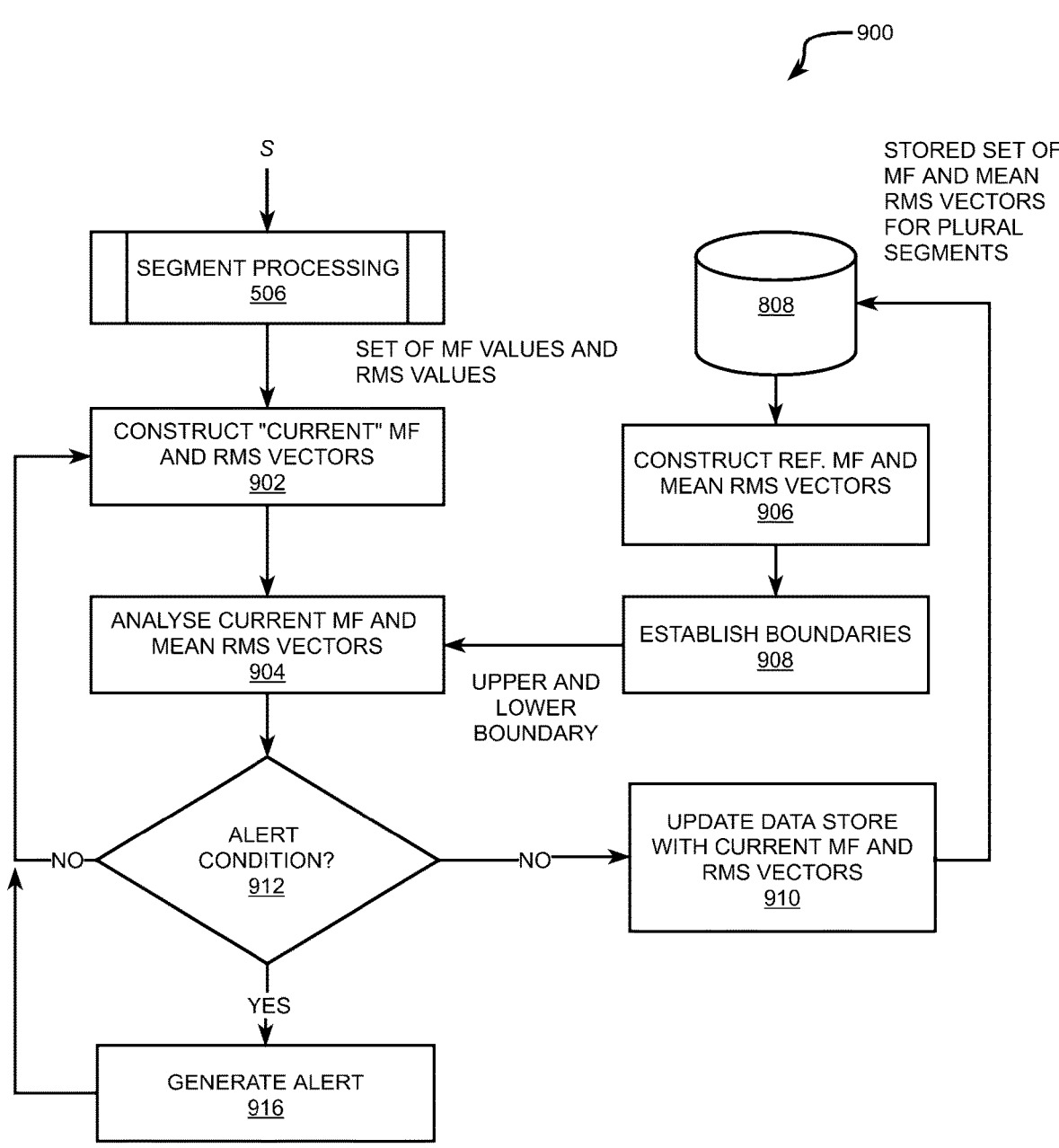
FIG. 11B is a flow diagram of an embodiment of a method of processing sensed signal data using the system shown in FIG. 11A.

In certain embodiments, and as is shown in FIG. 11A and FIG. 11B, the analysis and detection function 508 may store, in data store 808, a set of MF vectors for plural segments S with each MF vector 804 containing up to n values. The set of MF vectors are processed by reference vector generation process 810 to construct, at step 906, a single "reference" MF vector 812 containing values which, in this example, comprise mean median frequency values across all segments for a particular relative frame. Similarly, an RMS vector 814 containing RMS values is also separately constructed for each segment and stored in data store 808 for processing by reference vector generation process 810 construct, at step 906, a single "reference" RMS vector 814 containing n values which, in this example, are the mean of the RMS across all segments in the same relative frames.

At step 908, boundary generation process 816 determines a standard deviation for the values of corresponding frames in the stored MF and RMS vectors (using each of the stored vectors for all segments and the variation in the MF and RMS values in each corresponding frame) and generates four additional vectors as lower and upper bounds for the MF and RMS vectors 812, 814 respectively. Alternatively, a selectable percentage offset from the MF and RMS vectors 812, 814 may be generated to establish two additional vectors to act as the lower and upper bounds for both the MF and RMS vectors 812, 814.

Continuing now with reference to FIG. 11B, having established lower and upper bounds for both the MF and RMS vectors 812, 814 using sufficient plural segments to form a reliable sample size, a segment S ('the current segment') for a current sampling time is then obtained and partitioned into a selectable number of frames using the previously described approach.

A "current" PSD is then derived from the spectrum for each signal component within each frame of the current segment S. An MF value of each PSD for each frame of the current segment S is then extracted (using, in this example, the MF determination process 610 of segment feature extraction function 506) and used to construct, at step 902, a "current MF vector" 804 (ref. FIG. 11A) comprising the set of MF values for each frame of the current segment S. An RMS value for the data contained within each frame of the current segment S may also be extracted, at step 718 (using RMS determination process 802 of feature extraction process 506) and used to construct, at step 902, a current RMS vector 806 (ref. FIG. 11A) including the set of RMS values for each frame of the current segment S.

Having constructed the current MF vector 804 and the current RMS vector 806, boundary processor 818 then characterises the current MF vector 804 and/or the current RMS vector 806 to detect an "alert condition" indication of a structural anomaly event proximal the location depending on the characterisation the extracted features.

In certain embodiments, characterising the current MF vector 804 and/or the current RMS vector 806 involves assessing, at step 904, differences between the MF and RMS values in each frame of the current MF vector 804 and the current RMS vector 806 respectively and the corresponding frame values of the MF reference vector 812 and the RMS reference vector 814 respectively. Assessment of differences between current MF/RMS values and reference MF/RMS values may be performed using any suitable technique.

MF and/or RMS Boundary Processing

One example of a suitable technique involves boundary processing process 818 comparing the frame values of the MF vector 804 and/or the RMS vector 806 respectively and the corresponding frame values of the reference MF/RMS vectors 812, 814 to determine if the MF/RMS value, in any frame, exceeds the respective establish upper bound and/or is less than the respective established lower bound discussed above. In this way, for example, a metric, such as a percentage out of bounds, may be determined using the current and reference MF/RMS value for corresponding frames. Alternatively or additionally, a number of out of bounds occurrences across all frames may be counted and a peak and/or average percentage out of bounds determined.

If the current MF/RMS frame values are within the respective established respective MF/RMS upper and lower bounds generated by boundary generation process 816, no anomaly indication is raised by alert processor 820. In this case, the data stored in data store 808 may be updated such that data for the "oldest" segment is shifted out of the data store 808 and frame values from the current RMS vector 806 and MF vector 804 included as each new segment S becomes available in a FIFO "sliding window" type manner. Reference vectors 812, 814 are thereafter updated according to the updated values.

If a MF and/or RMS frame value of the MF vector 804 and/or the RMS vector 806 respectively is below the corresponding lower bound, the current MF and/or RMS values may be stored in data store 808, or other suitable storage, for visualisation and assessment of signal level shifts at specific measurement sensors and an anomaly alert raised by alert processor 820. If particular frame values of the current MF/RMS values are below the corresponding lower bound, then the reference MF/RMS values may be updated as for the case where the current MF/RMS values are all within the bounds.

Occurrences above the respective upper bound, as statistically quantified in terms of a number of these occurrences (ie. a count), a peak and average percentage above the upper bound of the occurrences and/or an integrated total MF/RMS value of the current MF/RMS values above the reference MF 812/RMS 814 values upper bound, may be used to raise a structural anomaly event indication, such as a leak alert (possibly subject to an assessment of the noise as Gaussian).

In certain embodiments, if the current MF/RMS frame values (one or more of them) are above the respective upper bound then the reference MF/RMS values may be subject to additional or alternative methods of adjustment before the data signal 10 for the next sample is obtained and analysed.

For example, in certain embodiments, in a first method of adjustment the reference MF/RMS frame values (for time<t where t is the current time) are "frozen" or "retained" and not updated using the current MF/RMS values (for time=t) before obtaining the data signal for the next recording sample t+Δt (where Δt is the recording time interval). The new or next "current" MF/RMS values for time t+Δt are then processed to determine differences between current MF/RMS values and reference MF/RMS values above. Quantified statistics for the number of upper bound exceedance occurrences (the count), the peak and average percentage above the upper bound of the occurrences and the integrated total power of the current MF/RMS values above the reference MF/RMS values upper bound are used to re-confirm a structural anomaly indication, in the form of an alert, for the new or next "current" MF/RMS values at time t+Δt.

In a second method of adjustment, the reference MF/RMS values (for time<t where t is the current time) are not "frozen" or "retained" and are instead updated using the current MF/RMS values (for time=t) before moving to the next recording time (t+Δt (where Δt is the recording time interval). The new or next "current" MF/RMS values for time t+Δt are then subject to the methods described above for assessing differences between current MF/RMS values and reference MF/RMS values.

In embodiments, an operational response indication or requirement may also be set in associated with an alert, depending on statistical quantification of the exceedance of the upper bound, and analysis of the associated spectrum, with associated different response levels (matching practical response capability). For example, if the peak percentage above the upper bound is 10% or less (operator selectable) then an operational response time indication or requirement may be set as slow (for example, >2 weeks). However, if a peak percentage above the upper bound is 100% or more (operator selectable) then the operational response indication or requirement may be set as "fast" (for example, <24 hours).

Rate of Change Processing

In certain embodiments, a set of statistics may be generated to characterise a rate of growth of extracted features of the data signal 10 within the framework of the established MF/RMS values and their respective frames.

For example, in certain embodiments a rate of change (ROC) of a peak and average percentage above the upper bound of the occurrences and/or the integrated total MF/RMS value, also above the upper bound, for the new or next "current" MF/RMS values may be determined by establishing differences between each parameter for the new or next "current" (time=t+Δt) relative to the updated reference MF/RMS value (including the effect of the changes at time t) and quantifying a percentage shift and/or percentage shift in time.

The above is repeated for time=t+2Δt, t+3Δt . . . t+nΔt.

Depending on the sampling interval Δt, a selectable number of consecutive data signals may be used to assess the ROC of the extracted feature or features, such as indicative statistic parameters in order to classify a leak/crack event. For example, if the ROC:

reduces to 0 (±a % tolerance) after a selectable number of consecutive recordings (the assessment period) then the fault may be assigned a diagnosis as either a likely joint leak or circumferential crack; or continues to increase (selectable bands can be set—e.g., 10% growth rate for predetermined number of consecutive recordings) then the fault may be assigned a diagnosis as a likely longitudinal crack.

FIG. 12A shows an example functional block diagram 920 for the determination of Rate of Change (ROC) information and event characterisations.

As shown, the functional block diagram 920 involves obtaining a set of acoustic measurements performing signal analysis and feature extraction 504/506, establishing benchmarks 924 for, ROC analysis 926, comparing on-going data with the established benchmarks 928 to provide statistical measures 930, 932 and an alert process 934 for conditionally generating an alert for investigation and rectification 936 depending on the statistical measures 930, 932.

In this example, signal analysis and feature extraction 504/506 involves the same processes described above in relation to the segment processing function 504 and feature extraction process 506. ROC analysis 926 may involve one or more targets to detect and characterise a structural anomaly as a longitudinal crack, a circumferential crack or a joint leak.

Establishing the benchmarks (BM) 924 may involve establishing short period BMs and/or longer period BMs. Short period BMs may be based on, for example, a daily or weekly period, whereas longer period BMs may be based on a monthly period. It will of course be appreciated that other suitable periods may be used to establish the benchmarks. For example, a suitable period may be set, or adjusted, depending on parameters such as the time of year, weather, or water demand/usage patterns.

Comparison 238 of on-going data with BMs may involve using measurements over, for example, a previous week, month, or plural months, depending on the ANN model structure established. However, longer and "rolling" data through BMs may be used to provide a continuous ROC indication.

The ROC of the peak and average percentage above the upper bound of the occurrences and the integrated total MF/RMS value, also above the upper bound, for the new or next "current" MF/RMS values may also be determined by establishing the differences between each parameter for the current (time=t) and new or next "current" (time=t+Δt) and quantifying a percentage shift and/or percentage shift in time.

In certain embodiments, the ROC is assessed relative to the established benchmark MF/RMS values within their respective frames (e.g., frequency windows) or for benchmarks established using integrated totals across all frames. For example, benchmarks may be established for each measurement location and can be established over durations of days, weeks or months.

Benchmarks established over shorter periods may reflect (and account for) dynamic changes in system and environmental noise at specific locations. Benchmarks established over longer periods are less reactive to dynamic changes in system and environmental noise at specific locations and are more sensitive to changes in MF/RMS within their respective frames and can be used to detect early crack development.

Measurement data for a period of days, weeks or months may be compared with the relevant established benchmarks to determine quantified statistics for the ROC that is occurring.

Figure 12B:
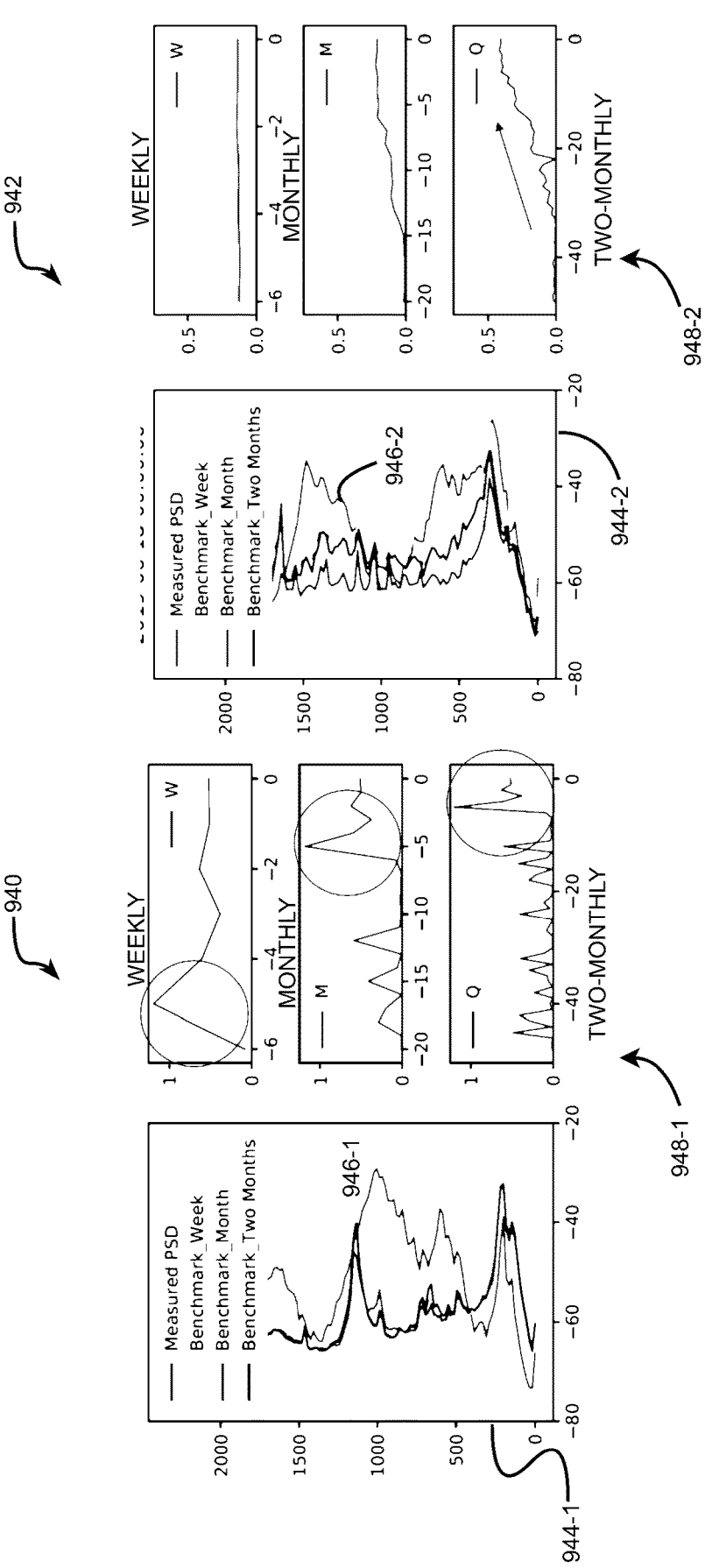
FIG. 12B is a set of plot diagrams depicting the application of rate of change techniques to data derived from acoustic measurements from circumferential and longitudinal crack events.

FIG. 12B depicts the application of the above method to data derived from acoustic measurements from circumferential (plot diagrams 940) and longitudinal (plot diagrams 942) crackevents. As shown in plot diagrams 948-1 and 948-2 respectively, the deviation of the current measured frequency and/or MF plot 946-1 from all short and longer period established benchmarks is clear for the circumferential crack due to an abrupt change in data for this event. On the other hand, the deviation of the current measured frequency and/or MF plot 946-2 is only clear for the slower developing longitudinal crack when the longer period benchmarks of one or two months (labelled "Q" in the plot diagrams 948-1 and 948-2) are applied.

Specific longitudinal crack events are known to only result in growth in specific frequency and/or MF frames (e.g., frequency windows). Integrated total median frequency/RMS value deviations from benchmarks are too coarse for detection and frequency band specific statistics must be calculated.

Figure 12C:
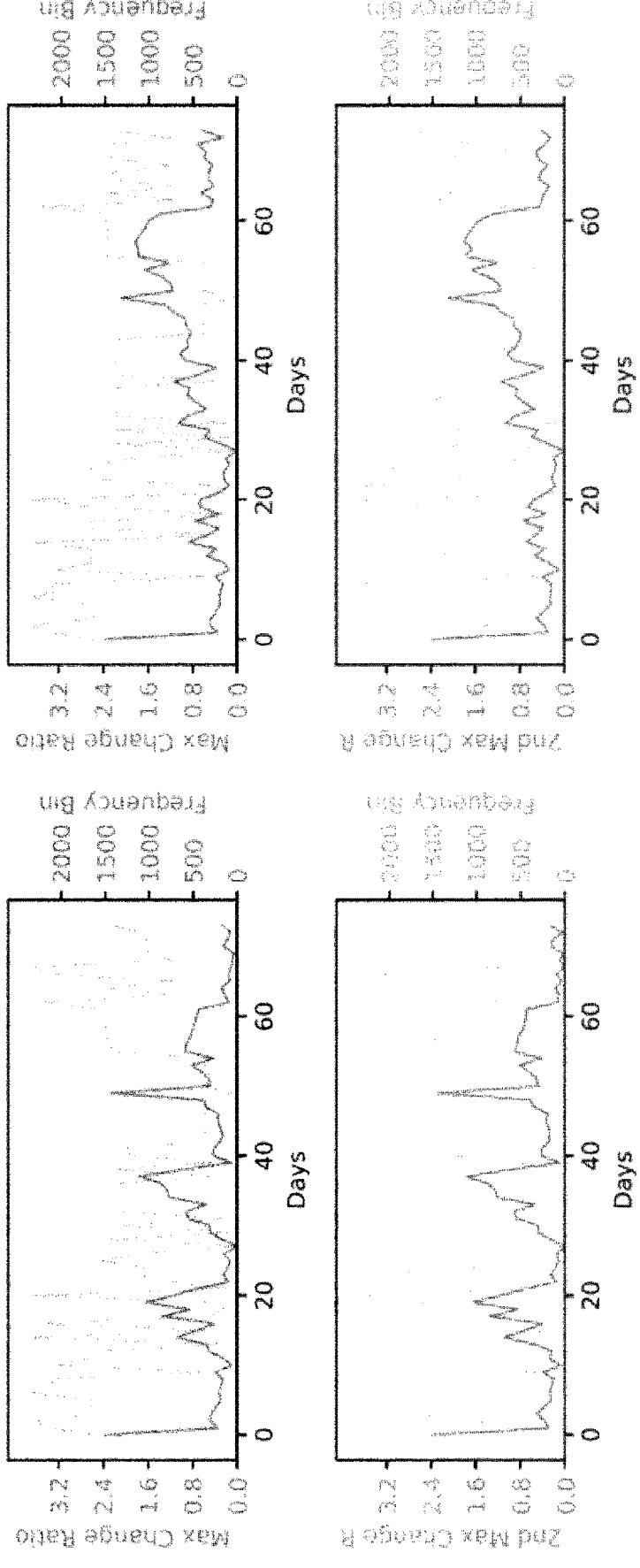
FIG. 12C shows plot diagrams for specific ROC calculations in ME frequency bands with the greatest change relative to band specific benchmarks.

FIG. 12C shows plot diagrams for specific ROC calculations in frequency and/or MF bands with the greatest change (upper most plot diagrams) relative to band specific benchmarks occurring. The result in the frequency band with the second greatest ROC (lower most plot diagrams) is also shown. Both results are for a slow developing longitudinal crack with the left hand plot pair exhibiting no sustained trend for a week benchmark (short period) versus the right hand plot pair exhibiting a sustained growth from day 30 to day 60 in both the greatest and second greatest frequency bands (the specific frequency band in which the growth is occurring is also plotted). The number of bands for which these statistics are determined may be expanded from the two greatest to all bands.

Figure 12D:
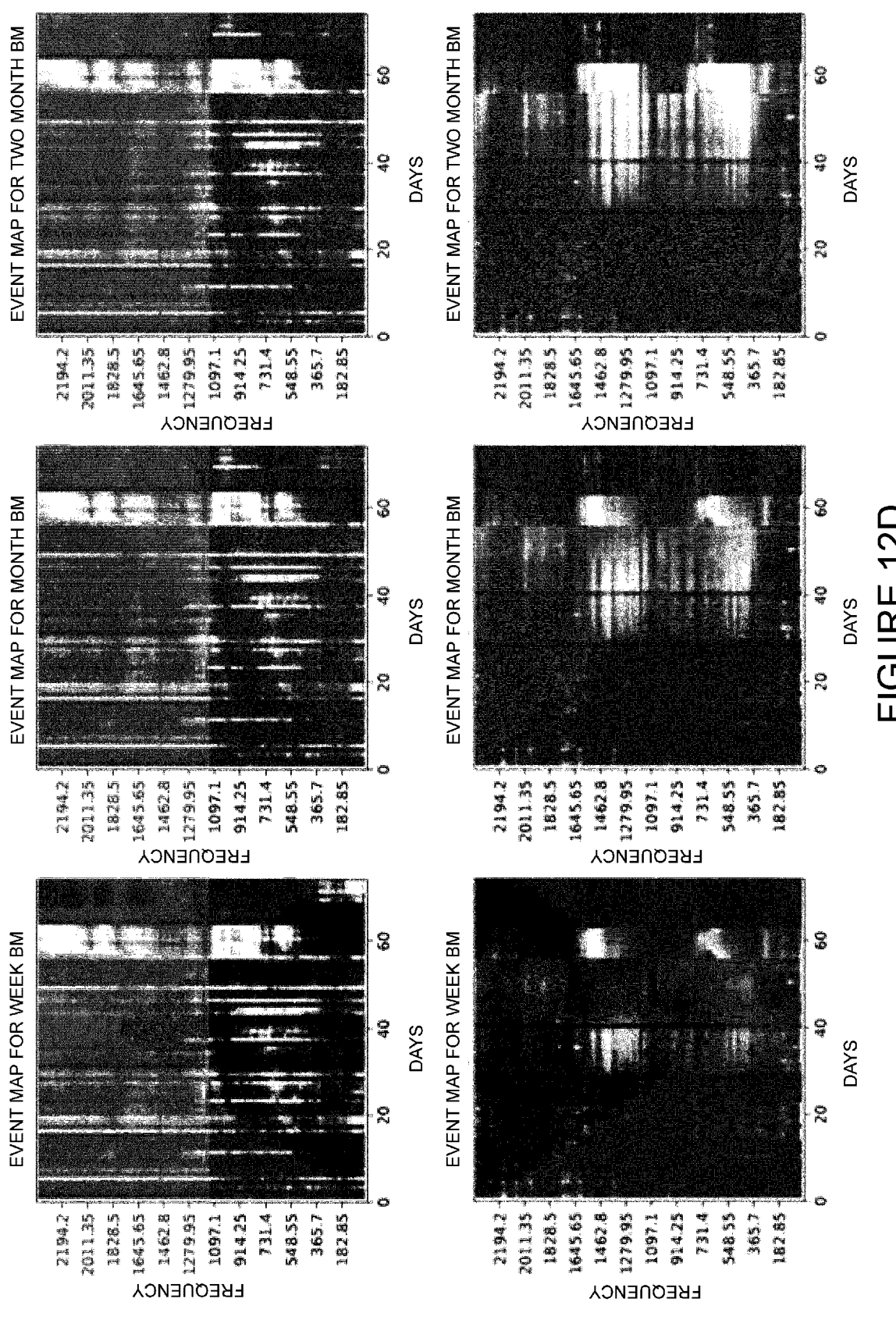
FIG. 12D shows 2D heat-maps for crack events differenced relative to a week, month and two month benchmarks.

In certain embodiments, it is possible that ROC may be represented visually for short and/or long period benchmarks as 2D heat-maps, as shown in the examples depicted in FIG. 12D. In the depicted examples, the upper three plots depict a circumferential crack event differenced relative to a week, month and two-month benchmarks. In certain embodiments, the abrupt characteristic of the circumferential crack and energy in frequency bands enable its specific diagnosis either by, for example, visual inspection, pattern recognition using an ANN, or an/or classification using an CNN or SVM with a suitably trained classifier.

The lower three plots depict a slow growing (over more than 30 days) longitudinal crack event differenced relative to a week, month and two month benchmarks. In certain embodiments, the gradual growth of the longitudinal crack and stronger manifestation relative to the long period benchmark enable its specific diagnosis by, for example, visual inspection, pattern recognition using an ANN, or an/or classification using an CNN or SVM with a suitably trained classifier.

While the above examples relate to frequency and/or MF processed data, analogous methods are applicable to RMS and other magnitude data.

Processing of PSD Reconstructed from MF/RMS

In certain embodiments, it is possible that a PSD characteristic for each of plural segments S may be constructed from the corresponding RMS and MF vectors generated over a selected number of intervals (i.e., acoustic data measurement intervals) and processed to provide a characteristic or representation including features for indicating a structural anomaly event depending on the characterisation or representation.

Figure 13A:
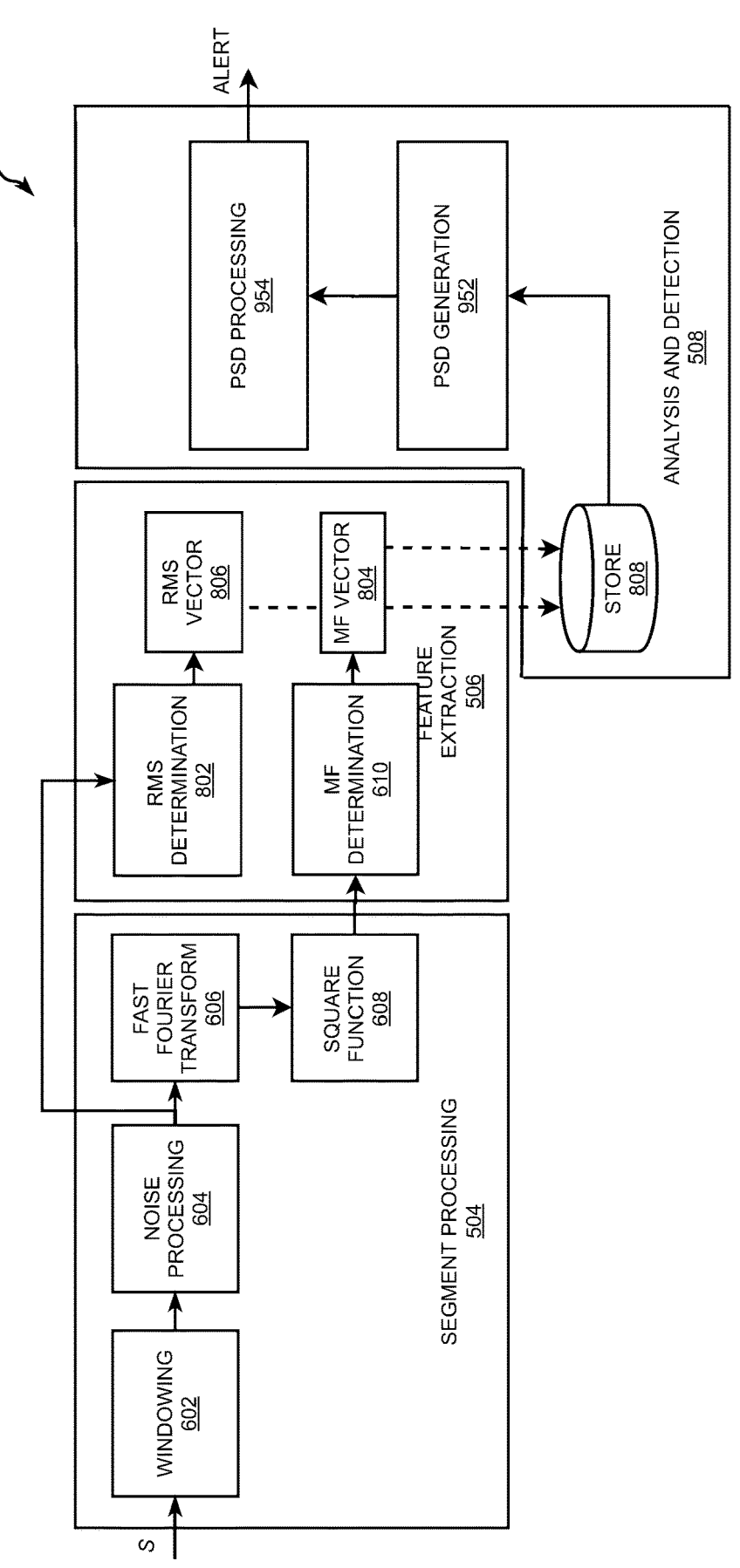
FIG. 13A is a functional block diagram of another system for processing a data signal according to an embodiment of the disclosure.

For example, functional block diagram 950 for one approach for processing a PSD characteristic reconstructed from corresponding RMS and MF vectors generated over a selected number of intervals using PSD generation function 952 and PSD processing function 954 is shown in FIG. 13A. Although the depicted example involves reconstructing a PSD from corresponding RMS and MF vectors, it is possible that, in another embodiment, the PSD may be constructed directly from the measured acoustic data.

Figure 13B:
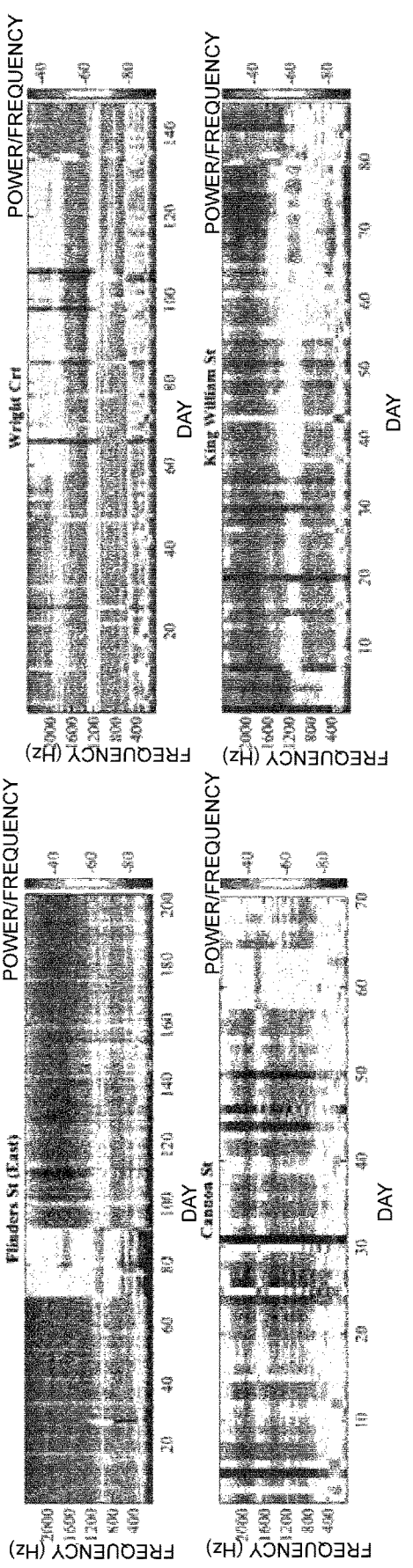
FIG. 13B shows two example sets of PSD mappings containing circumferential crack events illustrating the differences in physical responses for these events.

In certain embodiments, PSD generation function 952 generates a mapping of PSDs generated over a selected number of intervals for processing by PSD processing function 954. In this respect, FIG. 13B depicts two example sets of PSD mappings containing circumferential (left hand side plots top and bottom) and longitudinal (right hand side plots top and bottom) crack events illustrating the differences in the physical responses for these events enabling its specific diagnosis by, for example, visual inspection, pattern recognition using an ANN, or an/or classification using an CNN or SVM with a suitably trained classifier. In another embodiment, the PSD generation can occur directly from the measured data.

Figure 13C:
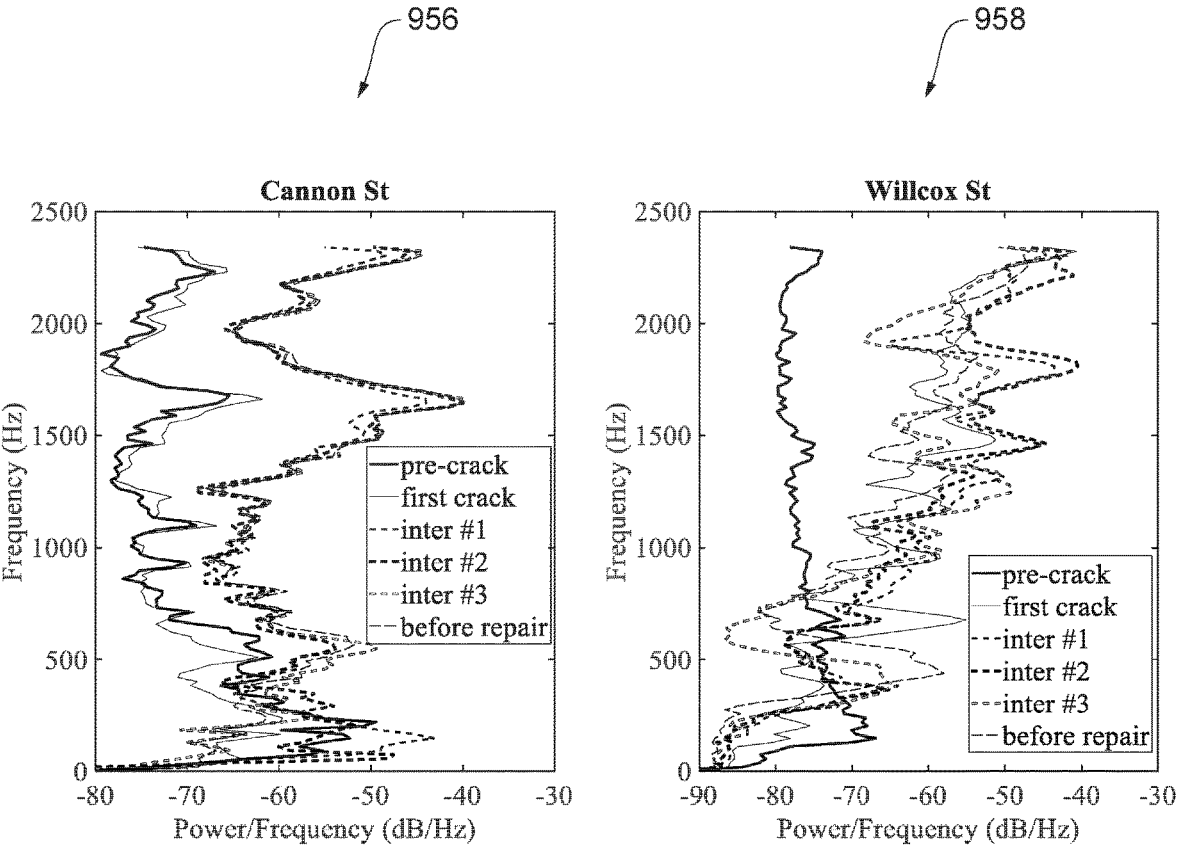
FIG. 13C depicts PSD plot diagrams derived as a series of PSD reconstructions for particular acoustic data measurement intervals shown in FIG. 13B.

FIG. 13C depicts PSD plot diagrams derived as a series of PSD reconstructions for particular acoustic data measurement intervals shown in FIG. 13B. In the illustrated example, PSD characteristics 956 represent the progression of a circumferential crack and PSD characteristics 958 represent the progression of a longitudinal crack.

Use of MF and/or RMS in Machine Learning

Figure 14A:
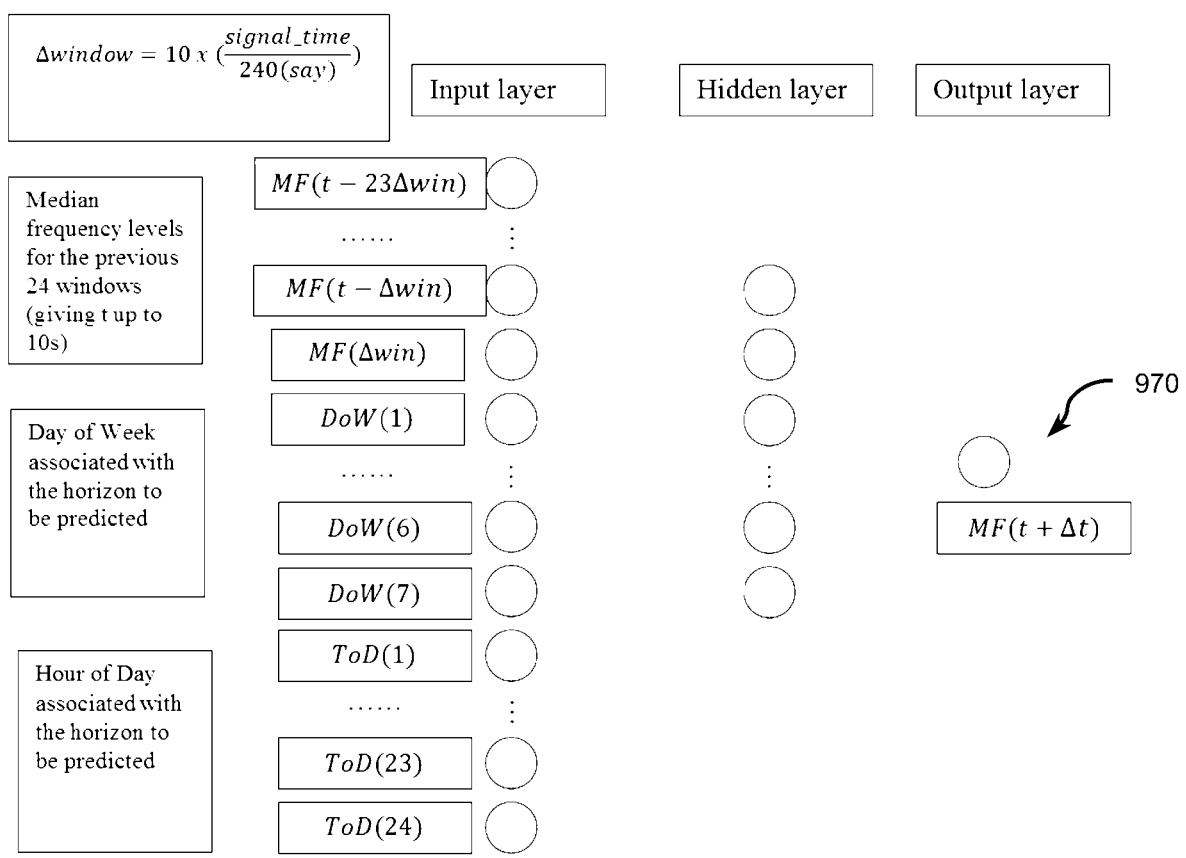
FIG. 14A is an example of an artificial neural network diagram for a machine learning embodiment for characterising MF values.
Figure 14B:
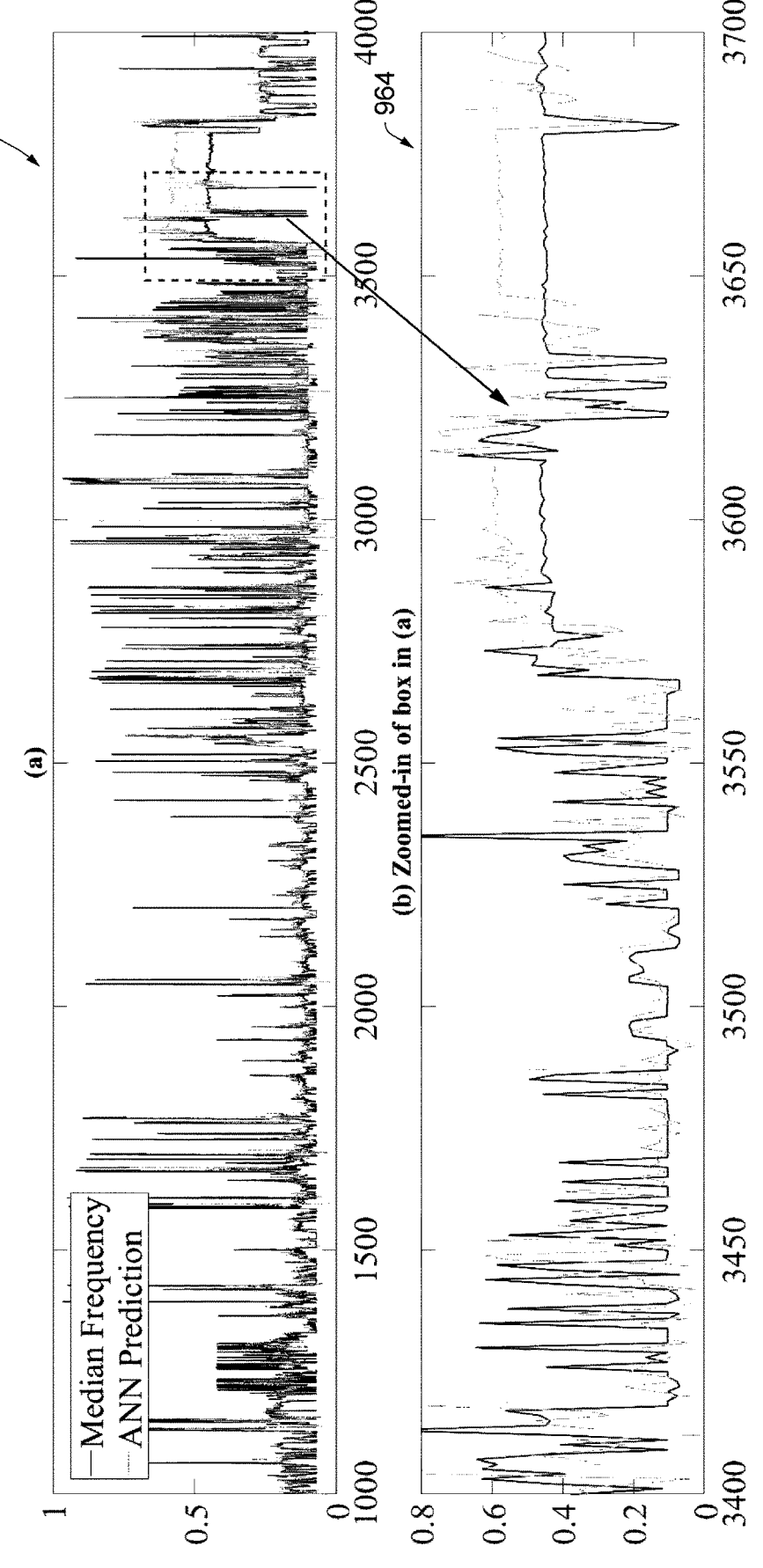
FIG. 14B is a plot diagram showing an example of a detection of a leak/crack event for a data signal flow involving using a machine learning embodiment to characterise MF values.

FIG. 14A is an example of an artificial neural network diagram for a machine learning embodiment for characterising MF values to produce an 'ANN Prediction'. Output neuron ($MF(t+\Delta t)$) 970 is the MF that is predicted based on data driven pattern training for a particular single window band on a particular day and at a particular time. FIG. 14B depicts plot diagrams 9662, 964 of an 'ANN Prediction' produced by an ANN network configured characterise to MF values obtained for a segment to detect a crack/leak event.

In the example depicted in FIG. 14A and FIG. 14B, MF values for reference and current vectors are determined in the manner already described.

As shown in FIG. 14A, MF values across plural time windows (e.g., 240) are banded into, for example, ten single window bands (width is selectable) and all available reference signals are used to generate banded MF training data sets which are then used to established the predicted pattern (shown as 'ANN Prediction') by machine learning (artificial neural network) using signal (noise) magnitude data for training. In this example, and as shown in FIG. 14A, the input neuron structure retains an ability to distinguish patterns that vary depending on the day of the week and time of day.

In the example shown in FIG. 14A, a departure from a predicted pattern may indicate a leak/crack event.

One example of such a departure is evident, in FIG. 14B, in the range of window 3550 to 3700 (indicated with a dashed box in plot diagrams 962, and shown in close-up in plot 964). Statistical average and peak percentage departures can be used to quantify the departure and urgency of operational response as previously described above. It is to be noted that a similar approach could be adopted for signal magnitude based training, characterising and detection and for RMS value based training, characterising and detection.

Figure 14C:
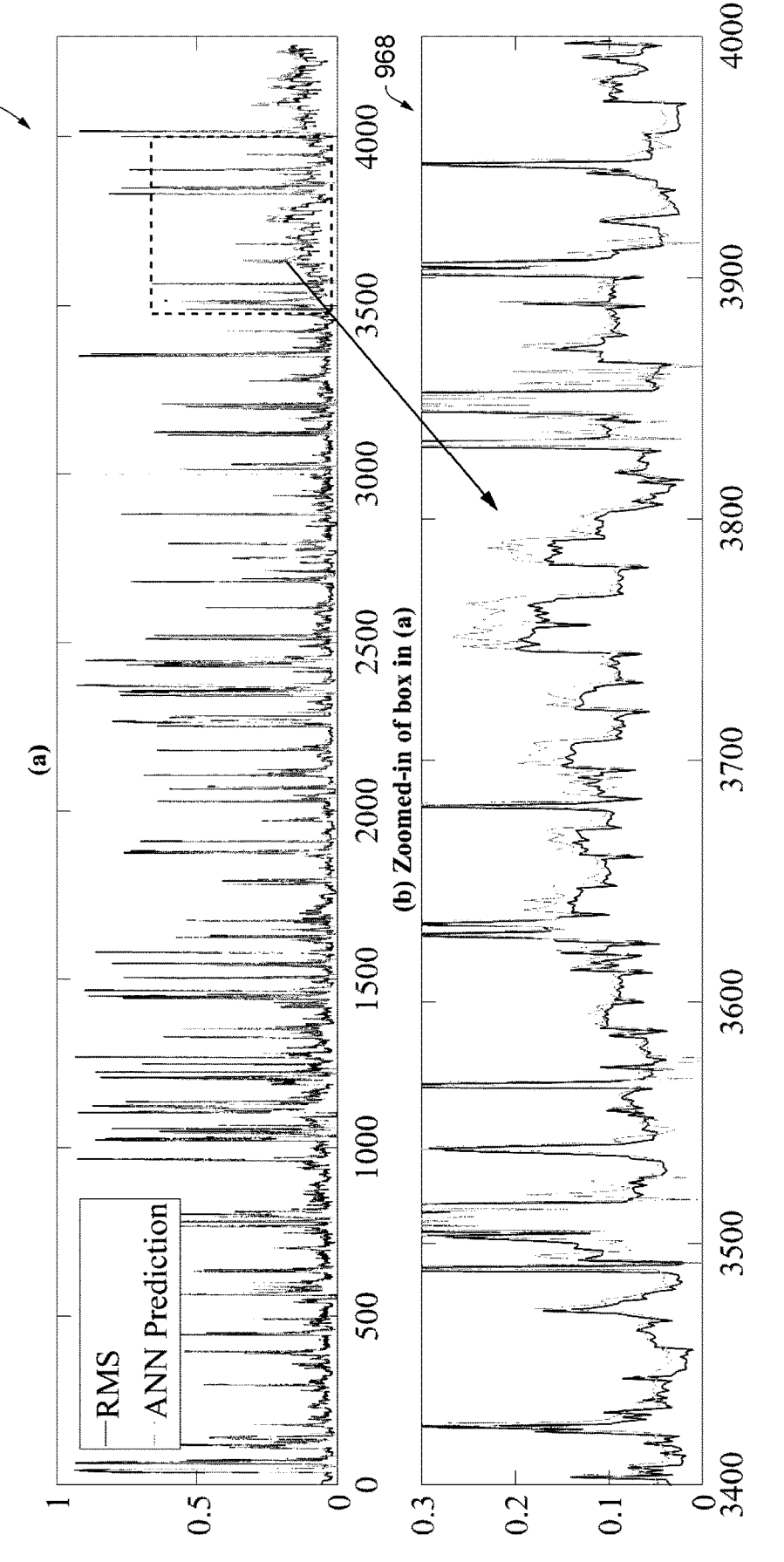
FIG. 14C is a plot showing an example of a detection of a leak/crack event for a data signal flow involving using a machine learning embodiment to characterise RMS values.

In this respect, FIG. 14C depicts plot diagrams 966, 968 of an 'ANN Prediction' produced by an ANN network configured characterise to RMS values obtained for a segment to detect a crack/leak event. In this example, the RMS values for reference and current vectors may be determined in the manner already described.

In the example shown in FIG. 14C, the RMS values across plural time windows (e.g., 240 time windows) have been banded into, for example, 10 plural single window bands and reference signals are used to generate banded RMS training data sets which are then used to established a predicted pattern (shown in FIG. 14C as 'ANN Prediction') by machine learning (artificial neural network) using signal (noise) magnitude data for training. In this example, an input neuron structure retains an ability to distinguish patterns that vary depending on the day of the week and time of day.

In the example shown in FIG. 14C, an output neuron (MF(t+Δt)) is the RMS value that is predicted based on data driven pattern training for a particular single window band on a particular day and at a particular time. In this example, a departure from a predicted pattern may indicate a leak/crack event. Examples of such departures are evident in FIG. 14C in the range of windows 3750 to 3800 (indicated with a dashed box in plot 966 and shown in close-up in plot 968). Statistical average and peak percentage departures can be used to quantify the departure and urgency of operational response as previously described above.

CUSUM Processing

Figure 15A:
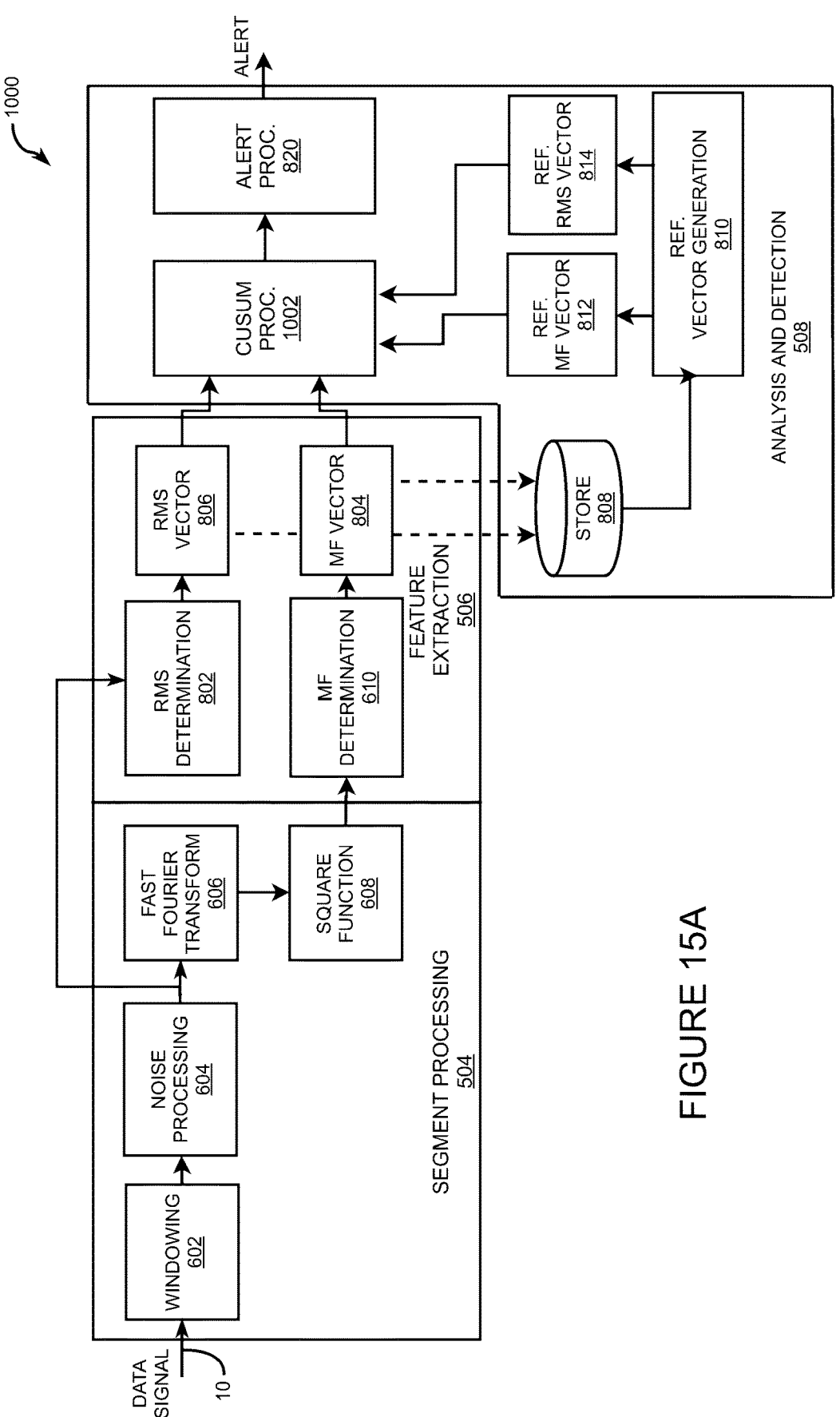
FIG. 15A is another functional block diagram of another system for processing a data signal according to an embodiment of the disclosure.

FIG. 15A depicts a schema 1000 for another technique for assessing differences between frame values of current MF/RMS vectors 804, 806 and corresponding frame values of the reference MF/RMS vectors 812, 814.

The example schema 1000 depicted in FIG. 15A is similar to the example schema 800 depicted in FIG. 10 except that schema 1000 includes a CUSUM processor 1002 to extract, as a feature of the data signal 10, a value or values $C_i^+$ for characterising the data signal 10 based on a difference or differences between the frame values of the current MF/RMS vectors 808, 806 and the corresponding frame values of the reference MF/RMS vectors 812, 814 by applying a CUSUM algorithm to the respective frame values.

In general terms, a CUSUM algorithm accumulates differences between the "current" frame values for the MF/RMS vectors 804, 806 and the corresponding reference frame values of the reference MF/RMS vectors 812, 814 as follows:

$$C_i^+ = \max[0, C_{i-1}^+ + z_i - K_i] \qquad \text{Equation (6)}$$

where $z_i$ is the frame value of the $i^{th}$ frame of either the current MF vector 804 or the current RMS vector 806, and $K_i$ is the corresponding frame value of the corresponding reference vector 812 or 814 respectively. Since $K_i$ represents a "normal" value for the relevant frame window, $z_i - K_i$ represents the deviation from the normal value. In embodiments, for a particular frame value $z_i$, the reference value $K_i$ is a reference value obtained or determined for the same frame for the previous 30 days.

In embodiments, when the CUSUM $C_i^+$ is characterised as exceeding a user-defined threshold T, the corresponding data signal 10 is identified as an outlier indicating a structural anomaly event proximal the location at which the data signal 10 was sensed. In this respect, an outlier region (OR) by CUSUM may be defined by:

$$OR(T) = \{z_i : C_i^+ > T\} \qquad \text{Equation (7)}$$

where the threshold T represents either the increase in median frequency or RMS value required to characterise the extracted MF/RMS vectors 808, 806 as indicating the structural anomaly event.

In one embodiment employing a CUSUM algorithm, each 10 second wave file is broken into n frames, with each frame having an associated MF value and an associated RMS value.

Figure 15B:
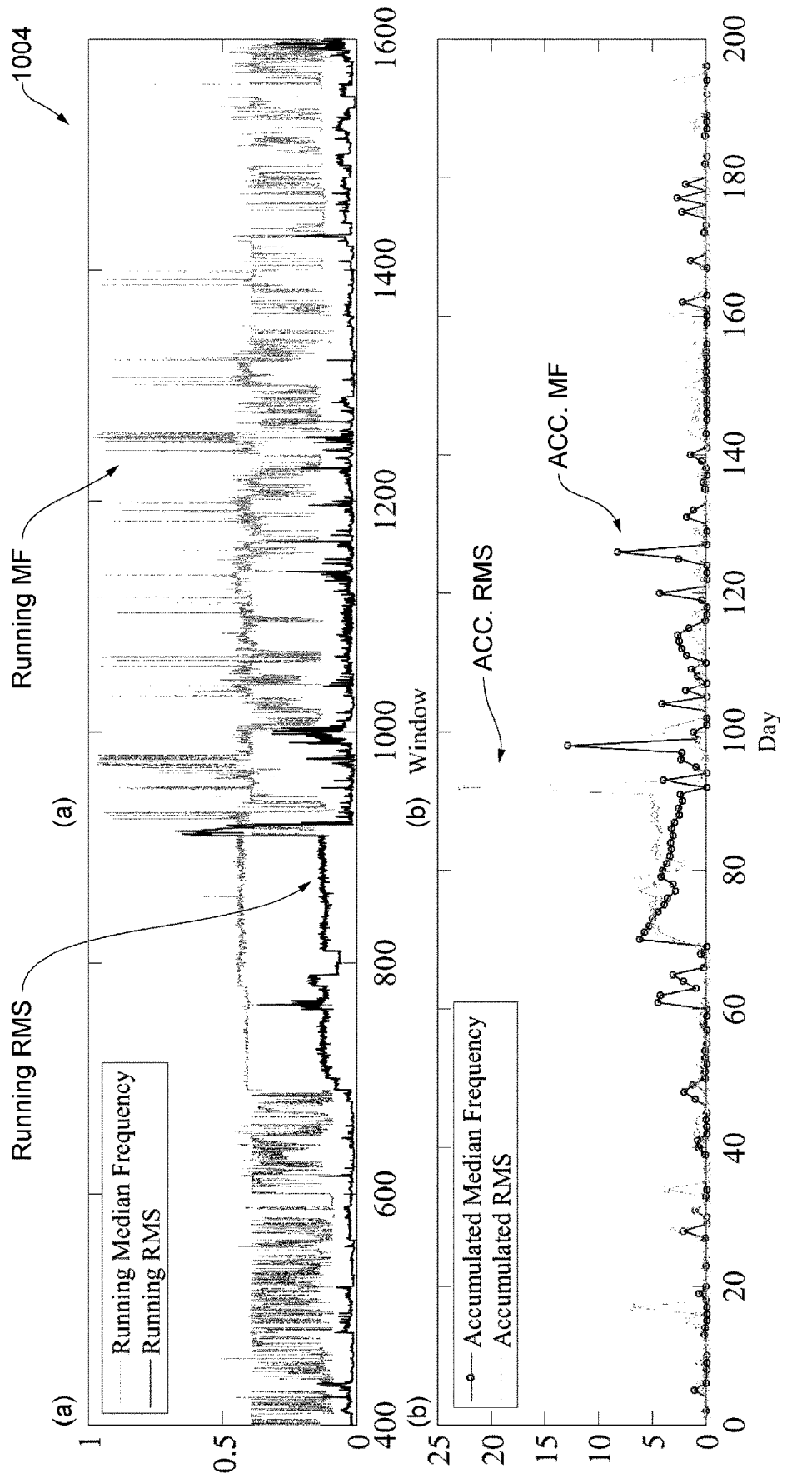
FIG. 15B is a plot diagram showing an example of a detection of a leak/crack event characterised by an elevated CUSUM MF and RMS response.

Turning to FIG. 15B, there is shown an example involving the construction of accumulated MF and RMS values for 200 wave files (ie. one wave file for each day of 200 days), and with n=10, meaning that overall there are 2000 frames. In this respect, FIG. 15B(a) shows a plot diagram 1004 including 1200 of the set of 2000 MF and RMS values.

In certain embodiments, a CUSUM algorithm is applied for each 10 second wave files (with n frames) with an initialization $C_i^+$ being 0. Equation (6) is then applied iteratively until $C_n^+$ for the last frame is calculated. $C_n^+$ is a representation of accumulated MF or RMS for a particular day, and as is shown in FIG. 15(b), is formed by joining the set of $C_n^+$ for all 200 days.

Although the above described examples involve particular techniques for processing MF and/or RMS noise features extracted for each of the plural frames of a data signal 10 to characterise the features as indicating a structural anomaly, it is possible that other techniques may be used. Other suitable techniques may involve statistical techniques, machine learning, pattern recognition techniques, digital filtering (such as Kalman filtering techniques), or combinations thereof. For example, differences between the current median frequency/RMS values and reference median frequency/RMS values may be assessed by applying Kalman filtering to vector representations of signal magnitude versus time.

Example 3

Predictive Power Spectral Extraction and Characterisation

Figure 16:
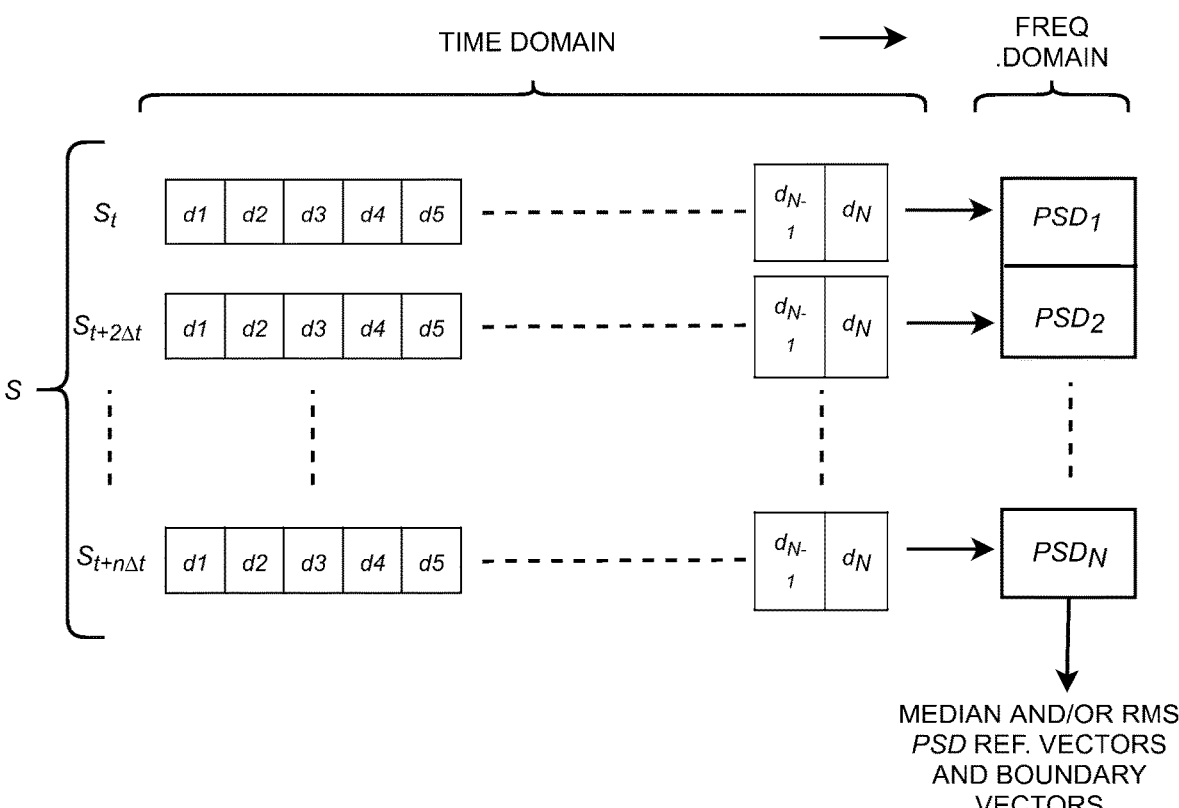
FIG. 16 is an example data structure for a data signal obtained by an embodiment.
Figure 17:
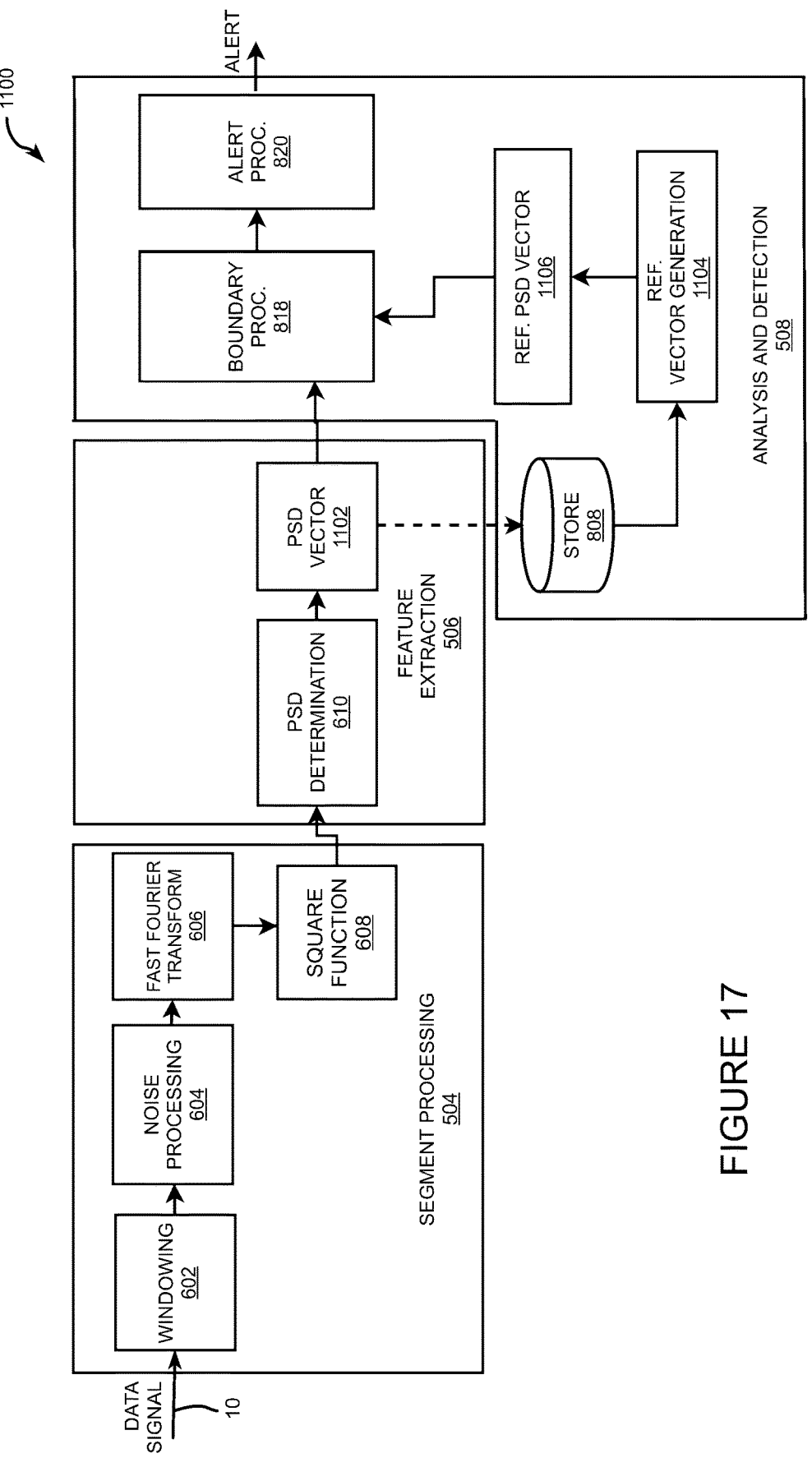
FIG. 17 is another functional block diagram of another system for processing a data signal according to an embodiment of the disclosure.

Turning now to FIG. 16, there is shown another example data structure for segmenting a data signal 10 obtained by an embodiment. FIG. 17 shows a functional block diagram of another system 1100 for processing a data signal 10 according to an embodiment of the disclosure using the data structure depicted in FIG. 16.

In the example depicted in FIG. 17, a single representative (such as a mean and/or single median) PSD is derived from the spectrum for each of a selectable temporal set of segments $S = \{S_t + S_{t+\Delta t} + S_{t+2\Delta t} + \ldots + S_{t+n\Delta t}\}$, where $\Delta t$ is the sampling interval, to determine a reference PSD, such as a reference mean PSD and/or a reference median PSD for the set of segments S.

With reference to FIG. 17, PSD determination process 610 determines a single representative PSD of a set of data segments S by processing plural data segment S from segment processing block 504 to generate a set of PSDs for the frames in the data segment (ref. FIG. 8, step 710). To obtain a single representative mean PSD, the averaged power density value for each frequency bin is firstly obtained by summarising the power density values for that specific frequency bin across all the available PSDs, then dividing the summation by the total number of PSDs in the set. Combining all the averaged power density values for all the frequency bins provides a representative mean PSD for the data segment S. The number of frequency bins and their frequency positions are selectable in the FFT process 606. Suitable FFT processes would be understood to a skilled person.

To obtain a single representative median PSD, the median PSD value for each frequency bin is obtained by analysing all the power density values for that particular frequency bin across all the available PSDs. The median value is the value at the 50th percentile, meaning that 50% of the values are smaller than the median and 50% are larger than the median. In certain embodiments, the median value can be obtained by ranking all the power density values for a particular frequency bin (across the set of PSDs) from the lowest to the highest, and then selecting the middle one in the rank as the median value. Combining all the median power density values for all frequency bins then provides the representative median PSD for the data segment S.

The representative (mean and/or median) PSD may be determined for each segment S in a set of historical data segments (the historical data segment set can be defined by a "sliding window" manner, e.g. the previous 30 data segments relative to the current segment). A set of representative PSDs determined in this way may then be used to determine a reference PSD.

In this example, the or each mean PSD for each specific frequency bin is determined from the set of the representative PSDs. The combination of the mean power density results for all the frequency bins available provides a reference PSD for the set of historical data segments. That is, the or each reference PSD comprises a vector containing N power density values (e.g., power per frequency=dB/Hz) determined over N discrete (selectable) frequency bands covering the full range of frequencies recorded by the set of segments.

In certain embodiments, multiple frequency bins can be combined to form a single frequency band. In such a case, the power densities of all the bins used to form the band may be combined to represent the power density of that band. The result is a vector representation of the mean and/or median reference PSD with M discrete power density values over M discrete (selectable) frequency bands. In other embodiments, a frequency band may contain a single frequency bin. The more general concept of "frequency band" is used in the description that follows.

A standard deviation of the values in the mean and/or median reference PSD vectors may be determined (using all segments and the variation in the power density values in each discrete frequency band) and used to establish two additional vectors in the form of a lower and upper bound vectors for the mean and/or median reference PSD vectors.

Alternatively, a selectable percentage offset from the mean and/or median reference PSD vector values is used to establish two additional vectors as lower and upper bound vectors.

A segment S for a current sample time may then be obtained and a "current" PSD vector 1102 extracted. The current PSD vector 1102 may be determined using the same discrete frequency bands used to establish the corresponding reference PSD vector 1106. Differences between the current PSD vector 1102 and a corresponding reference PSD vector 1106 may then be characterised to detect an indication of a structural anomaly event. Any suitable method may be used to characterise the difference for detection purposes.

In a first example of a suitable method for characterising the difference for detection purposes, a mathematical comparison of the values of the current PSD vector 1102 and reference PSD vector 1106 may be undertaken by boundary processor 818 to determine if the PSD of the current segment, in any frequency band, either exceeds an establish upper bound or is less than an established lower bound. A percentage out of bounds may then be determined using the current and reference power density values of the respective vectors for the corresponding frequency bands. The number of out of bounds occurrences across all frequency bands may be counted and the peak and average percentage out of bounds recorded. An integration of the power densities of the current PSD vector 1102 that are above the upper bound of the power densities of the reference PSD vector 1106 may also be performed to determine the total power that is above the upper bound for the current PSD vector 1102.

In certain embodiments, if the current PSD vector 1102 values are within the established reference PSD upper and lower bounds then no leak or anomaly alert is raised. In such a case, the selected number of segments (ie. past) is updated with the oldest segment removed and the current segment included. The reference segments are thereby updated and shifted (by one recording time interval) as each new segment becomes available in a "sliding window" manner.

Occurrences below the lower bound may be stored for visualisation and assessment of signal level shifts at specific measurement sensors and an anomaly alert raised accordingly.

If the current PSD vector has power density(s) below the lower bound then the reference PSD vector is updated as for the case where the current PSD has all power density(s) within the bounds.

Occurrences above the upper bound (statistically quantified in terms of the number of these occurrences (the count), the peak and average percentage above the upper bound of the occurrences and the integrated total power of the current PSD vector above the reference PSD upper bound) are used to raise a leak/crack alert (subject to assessment of the signal as Gaussian).

Figure 18:
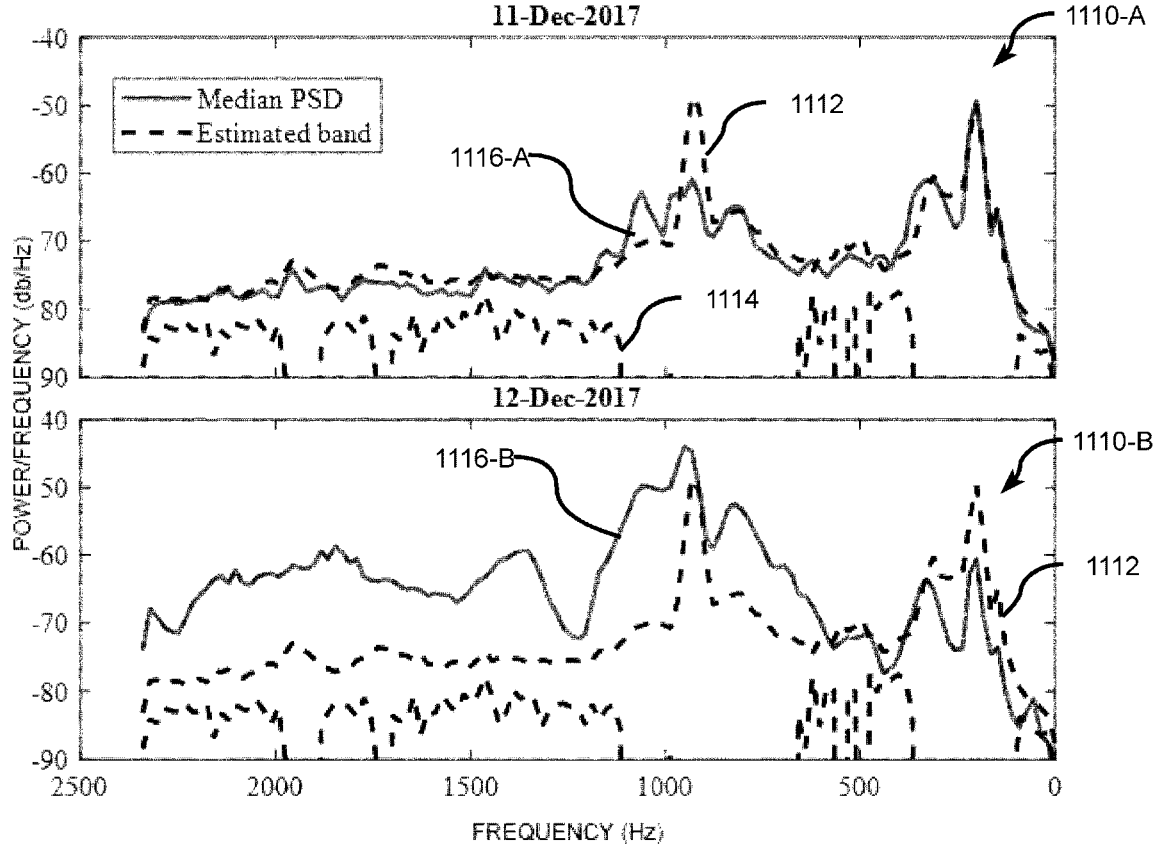
FIG. 18 is a plot diagram showing an example of a detection of a leak/crack event characterised by an out of bounds PSD using a mean and standard deviation approach with a relevant upper threshold.

FIG. 18 illustrates a pair of a set of plot diagrams 1110-A, 1110-B for a frequency range of 0 Hz to 2500 Hz. Each set of plots diagrams includes an upper median PSD bound plot 1112 (shown dashed), a lower median PSD bound plot 1114 (shown dashed), and a current median PSD plot 1116-A, 1116-B for a segment S of a data signal 10 which has been processed using an embodiment of the technique described as Example 2 above.

Plot diagrams 1110-A includes a plot of the characteristic of a current median PSD 1116-A prior to a leak/crack event on 11 Dec. 2007. As shown, plot 1116-A substantially falls within the upper 1112 and lower 1114 bounds across the frequency range of 0 Hz to 2500 Hz.

On the other hand, plot diagrams 1110-B includes a plot 1116-B of the characteristic of the current median PSD after a pipe crack event on 12 Dec. 2017. As shown, plot 1116-B exceeds the upper bound 1112 across substantially the frequency range of 0 Hz to 2500 Hz and, in this example, indicates a structural anomaly event for processing as a leak/crack alert by alert processor 820.

Although the above described examples involved particular techniques for processing a current median PSD plot feature extracted for a data signal 10 to characterise the current median PSD as indicating a structural anomaly, it is possible that other techniques may be used. Other suitable techniques may involve, for example, statistical techniques, machine learning (such as pattern classification or recognition techniques), digital filtering (such as Kalman filtering techniques), or combinations thereof.

Use of Kalman Filtering Techniques in PSD Processing

In certain embodiments, a Kalman filtering technique may involve obtaining a data signal 10 for a current recording time and then deriving a current PSD using the above described approach. The current PSD may be determined using the same discrete frequency bands used to establish a reference PSD. Differences between the current PSD and the reference PSD may then be assessed by applying Kalman filtering to the PSDs.

In certain embodiments, a Kalman filtering technique may detect a structural anomaly event for processing as a leak/ crack alert by an alert processor when differences between the current PSD and the reference PSD exceed a Kalman filter estimate based on a threshold.

Machine Learning Processing of RMS Magnitude and PSD

In certain embodiments, an ANN or RNN machine learning approach can be trained to patterns in noise magnitude data with deviations from these trained patterns diagnosable as leaks.

Figure 19:
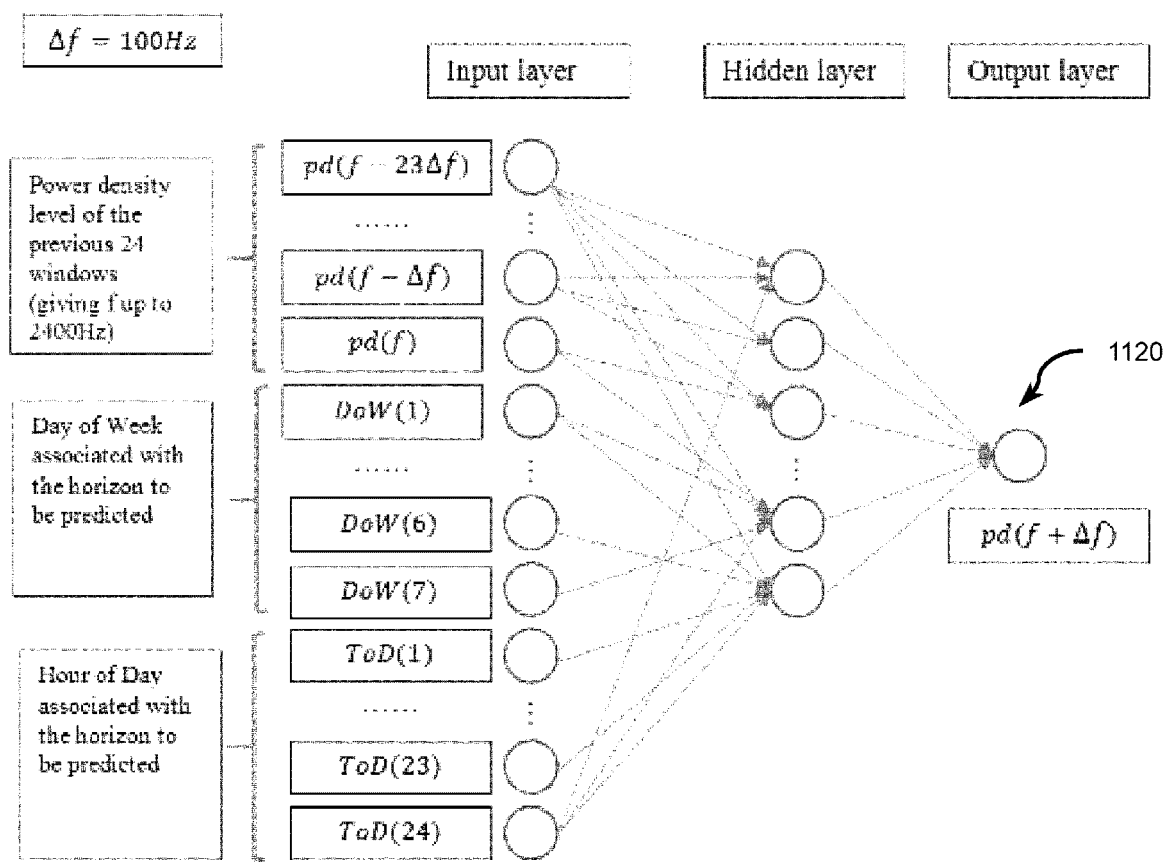
FIG. 19 is an example of an artificial neural network diagram for a machine learning embodiment for characterising power density values.

With reference now to FIG. 19, in certain embodiments, a machine learning approach may be used to process a current PSD and a reference PSD to detect a structural anomaly event. In such embodiments, PSDs for reference and current signal spectrums are determined in the manner described above. PSD levels in the PSDs may be banded into, for example, 100 Hz bands (width is selectable) and all available reference signals are used to generate banded PSD training data sets.

The generated banded PSD training data sets are then used to establish predicted patterns (labelled as 'ANN Prediction' in FIG. 19) by machine learning (ie. by an artificial neural network). In this example, an input neuron structure retains an ability to distinguish patterns that vary depending on the day of the week and time of day and the output neuron (pd(f)) 1120 (ref. FIG. 19) is the power density that is predicted based on data driven pattern training for, in this example, a particular 100 Hz band on a particular day and at a particular time.

In certain embodiments, a departure from the ANN prediction may indicate a crack/leak event. Statistical average and peak percentage departures can be used to quantify the departure and urgency of operational response as previously described in this document.

Figure 20:
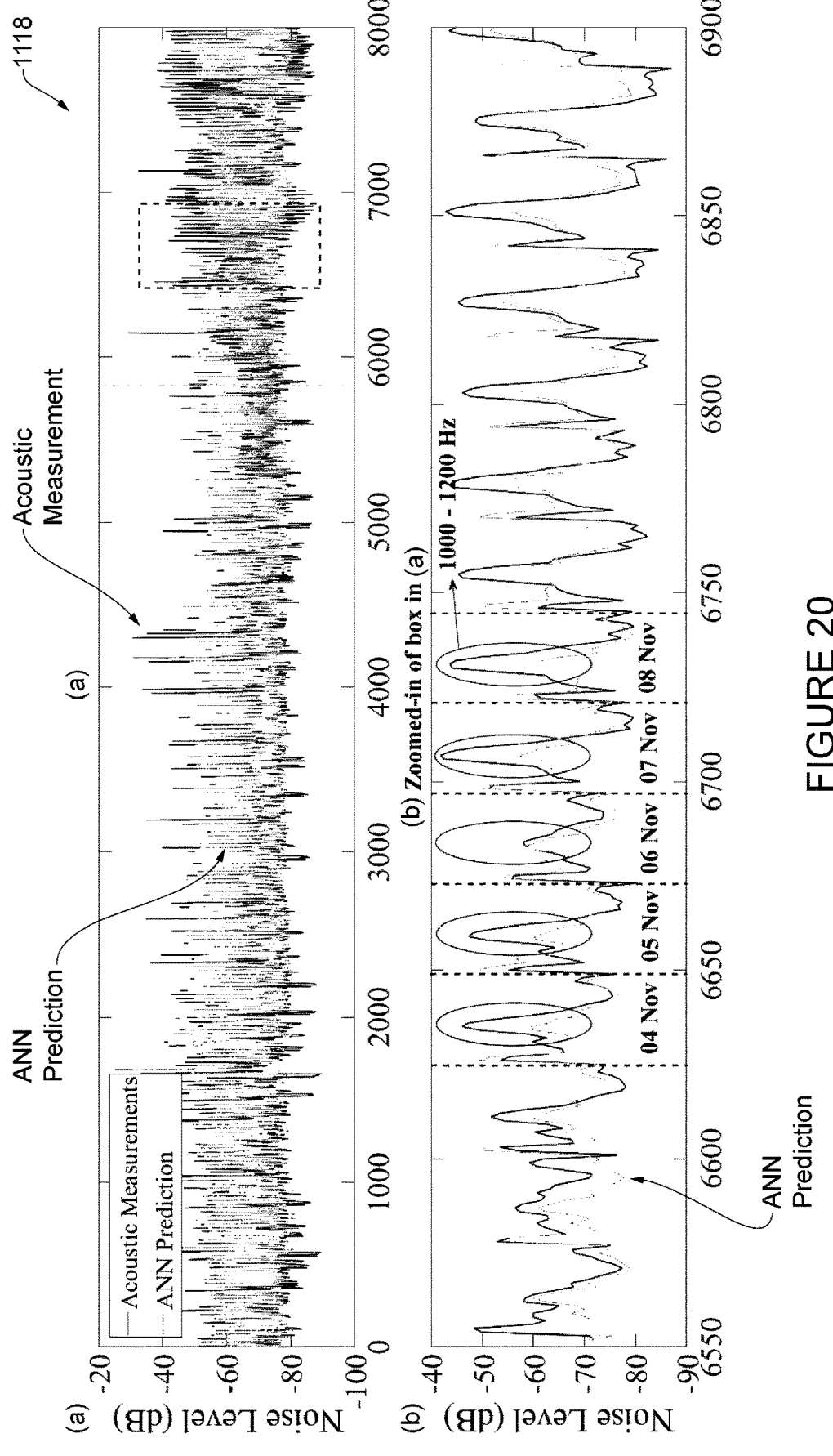
FIG. 20 is a plot diagram showing an example of a detection of a leak/crack event characterised by an out of bounds power density for frequency bands within a PSD.

FIG. 20 depicts example plots 1118 indicating a detection of a leak/crack event in the 1000 Hz to 1200 Hz band using a machine learning based approach applied to PSD segmentation process/feature extraction.

Figure 21:
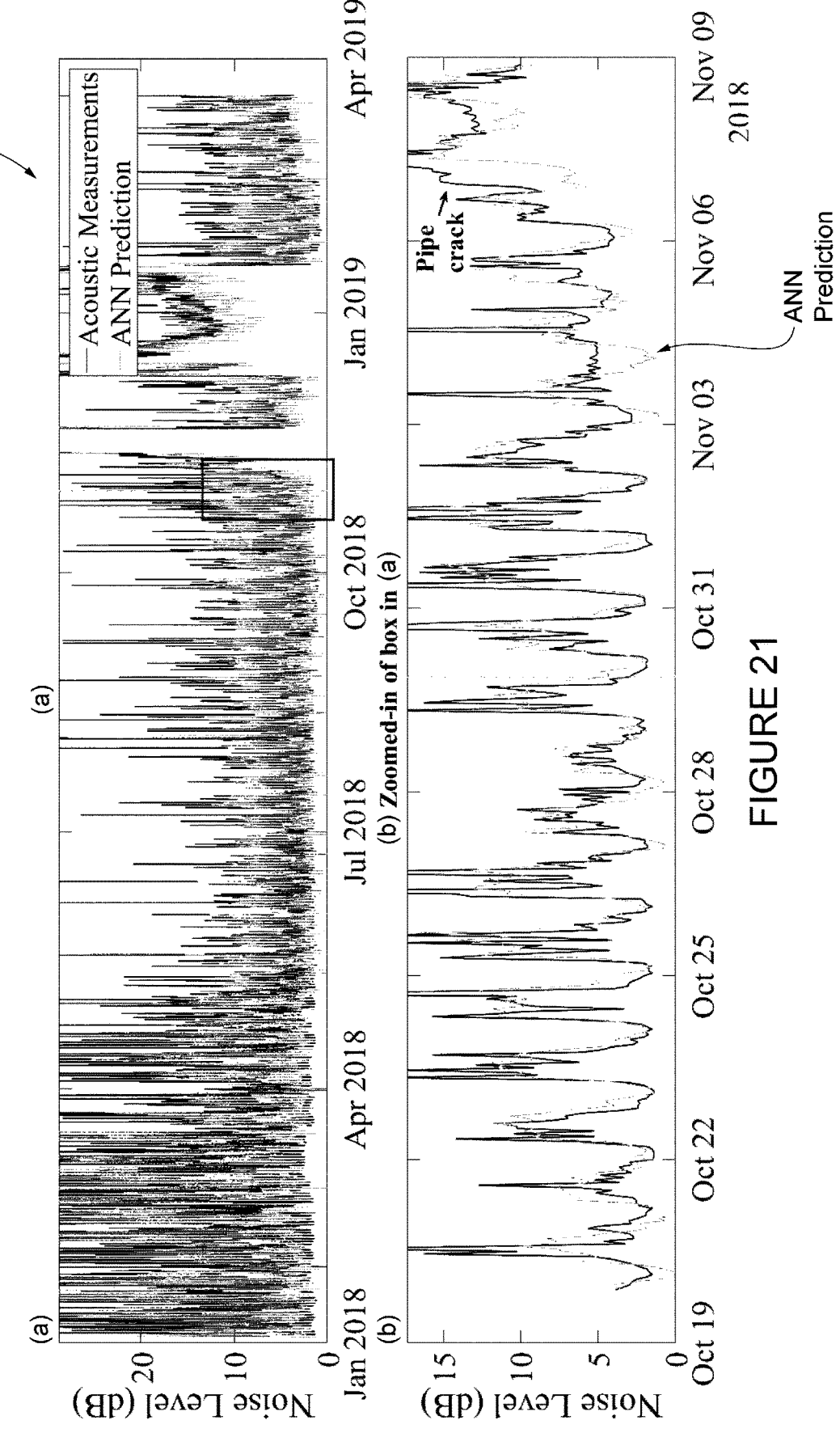
FIG. 21 is a plot diagram showing an example of a detection of a leak/crack event characterised by an out of bounds power density for frequency bands within a PSD.

FIG. 21 depicts example plot diagrams 1250 indicating a detection of a leak/crack event in the 1000 to 1200 Hz band using a machine learning based approach applied to signal noise magnitude.

Figure 22:
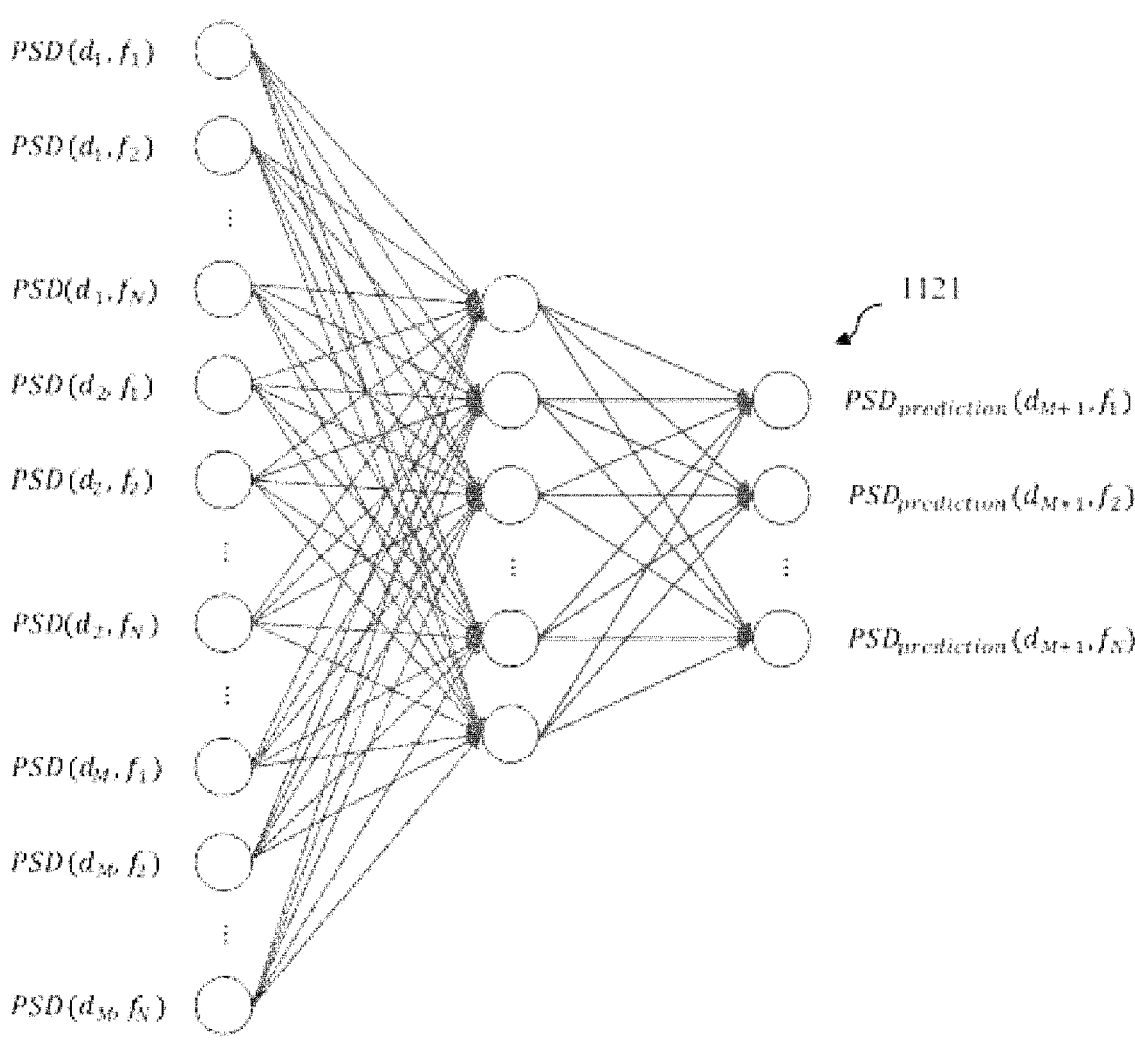
FIG. 22 is another example of an artificial neural network (ANN) diagram for a machine learning embodiment for characterising power density values.

In another example of a machine learning approach, as depicted in FIG. 22, historical frequency power and/or MF values in frequency bands may be derived from, for example, daily sound file data (measurement frequency can be more frequent than daily) for a predetermined number of days, weeks or months prior to the day for which a predicted MF (or PSD) is sought. The number of frequency bands (windows) used can vary (e.g., from 32, 64, 128 to 256 or greater). The input neurons for the ANN are established as the MF (or PSD) level for each frequency band in the relevant historical days, weeks or month(s) prior to the day for which a prediction is sought. The output neurons form a predicted MF 1121 (or PSD) over the defined frequency bands forming a predicted MF vector (or PSD). It certain embodiments, a recurrent neural networks (RNN) is used instead of an ANN.

Different trained ANN predictive models may be derived depending on the number of frequency bands used and the number of historical days, weeks or months used to provide training data. Analogously to the ROC and benchmark approach described above with reference to FIG. 12A, ANN predictions established over shorter periods may reflect dynamic changes in system and environmental noise at specific locations, whereas ANN predictions established over longer periods may be less reactive to dynamic changes in system and environmental noise at specific locations but may be more sensitive to changes in MF/RMS within their respective frames and can be used to detect early crack development.

Figures 23A, 23B:
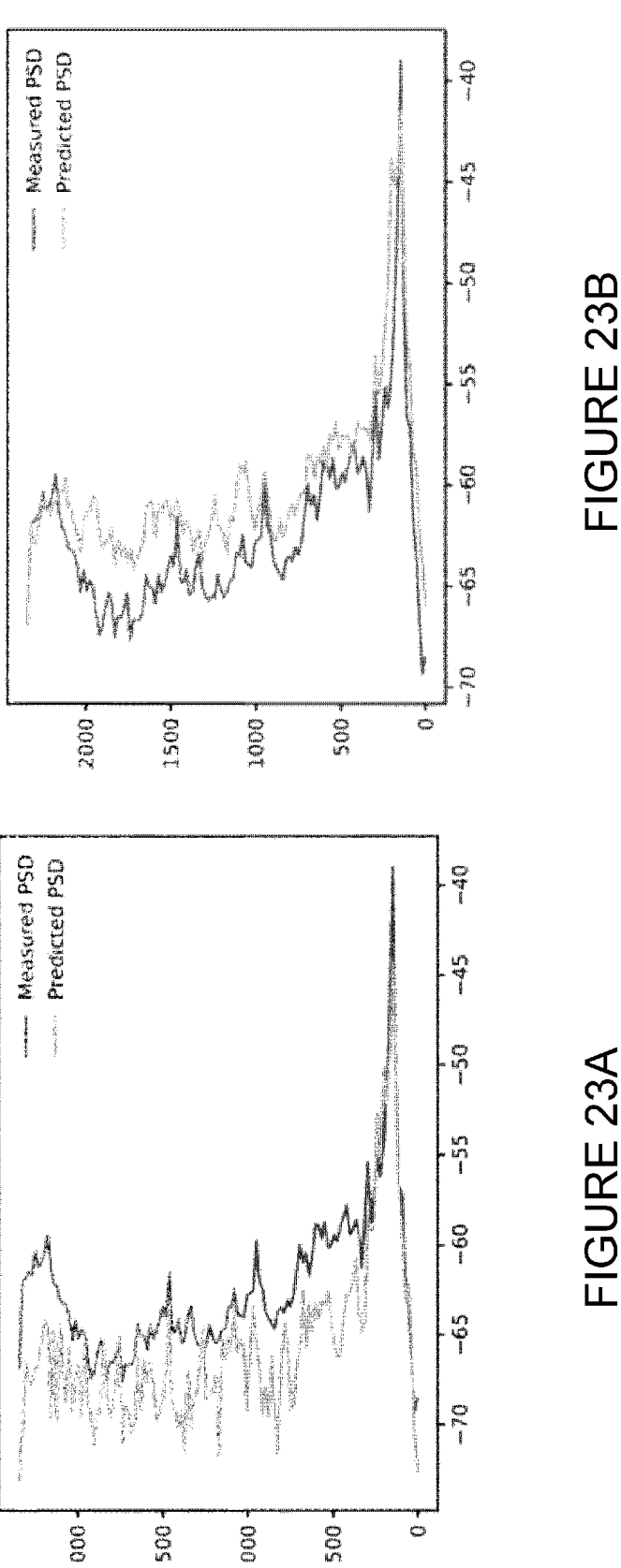
FIG. 23A depicts example plot diagrams showing predicted PSD versus current time period measured PSD from ANN models trained using one week of historical data.
FIG. 23B depicts example plot diagrams showing predicted PSD versus current time period measured PSD from ANN models trained using two months of historical data.

FIG. 23A and FIG. 23B depicts example plot diagrams showing predicted PSD versus current time period measured PSD from ANN models trained using one week of historical data (FIG. 23A) compared with two months of historical data (FIG. 23B) with, in these examples, the respective predicted PSDs being below (in FIG. 23A) and above (in FIG. 23B) the respective measured PSD thus illustrating a different outcome dependent upon, in these examples, the number of time intervals used to generate the predicted PSD.

Figure 24:
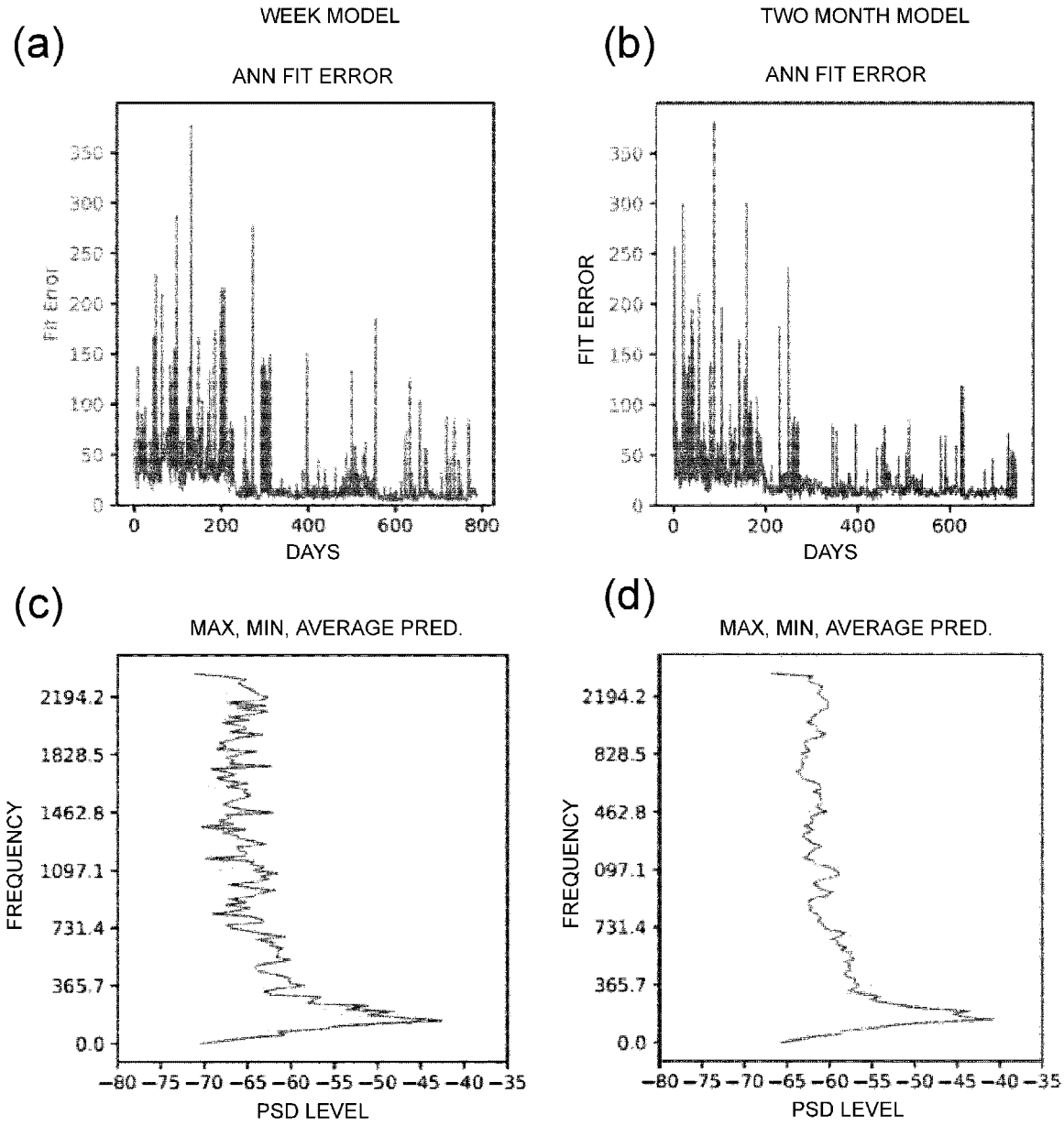
FIG. 24 depicts training error outcomes for models trained using a week of data versus two months of data.

FIG. 24 depicts training error outcomes for models trained using a week of data (FIG. 24($a$)) versus two months of data (FIG. 24($b$)) with the training error smaller for the shorter period model as a result of its reactivity to dynamic changes in system and environmental noise.

FIG. 24 also depicts stability of the "average" predicted PSDs (ref. FIG. 24($c$)) for the one-week model and FIG. 24($d$) for the two-month model) and the associated maximum/minimum deviation bands. As is evident from a comparison of FIG. 24($c$) with FIG. 24($d$), the two-month model exhibits a more stable prediction with narrower maximum/minimum deviation bands and thus may be more useful for slower growing longitudinal crack.

Integration of ROC and ANN/RNN Techniques

In certain embodiments, the statistical quantifications described above for the ROC methods may be applied to the above described ANN (and RNN) predictive methods. Furthermore, the use of the above described benchmarks derived using mean/median and standard deviation methods in the ROC method may be replaced with an ANN predicted "benchmark" based method.

FIG. 25 depicts a functional block diagram 1228 including interfaces between the ROC and ANN methods previously described. As shown, functional block diagram 1228 involves obtaining a set of acoustic measurements 1330, performing signal analysis and feature extraction 1232, establishing an ANN model structure 1236 for an ANN 1234, training the ANN models 1236, comparing on-going data with ANN predictions 1240 to provide statistical measures 1242, 1244, and an alert process 1246 for conditionally generating an alert for investigation and rectification 1246 depending on the statistical measures 1242, 1244.

Signal analysis and feature extraction 1232 may involve the same processes described above in relation to the segment processing function 504 and feature extraction process 506. ANN 1234 may involve the same target for ROC analysis, namely, to detect and characterise a structural anomaly as a longitudinal crack, a circumferential crack or a joint leak.

Establishing the ANN model structure 1236 may involve establishing an ANN 1234 model based on a weekly period to, for example, use data from a previous week to derive an ANN prediction for, for example, a next day. Alternatively, the ANN model structure 1236 may involve establishing an ANN 1234 model based on a monthly period to, for example, use data from a previous month to derive an ANN prediction for, for example, a next day. Alternatively, establishing the ANN model structure 1236 may involve establishing an ANN 1234 model based on a period comprising plural months to, for example, use data from plural previous months to derive an ANN prediction for, for example, a next day. Irrespective of which approach for establishing the ANN model structure 1236 is adopted, each model provides predictions on a band-by-band basis. It will of course be appreciated that other suitable periods may be used to establish the ANN model structure 1236. For example, a suitable period may be set, or adjusted, depending on parameters such as the time of year, weather, or water demand/usage patterns.

Training the ANN models 1238 may involve using all the data from a single sensing unit 104 (ref. FIG. 1), data from plural sensing units 104. Such data could include data with or without known events excluded. The ANN models can be trained using location specific sensing unit records or by using plural sensing unit records with no distinctions based on the locations of the plural sensing units.

Comparison of on-going data with ANN predictions 1240 may involve using measurements over, for example, a previous week, month, or plural months, depending on the ANN model structure established. However longer and "rolling" data through ANN predictions maybe used to provide a continuous ROC indication.

FIG. 26 and FIG. 27 depicts an example result from functional block 1228. FIG. 26 shows results obtained with an ANN prediction derived from a week model (using one week of historical data to derive the ANN prediction). FIG. 27 shows results obtained with an ANN prediction derived from a two-month model (using two months of historical data to derive the ANN prediction).

An average prediction obtained using the model can be taken over a selected number of historical previous time periods (e.g., 50) and maximum and minimum deviations from this average determined with a selectable threshold added above the maximum and below the minimum to set detection limits.

A single or more exceedances of the thresholds can be used to generate an operational alert and/or an integrated total of exceedance between a measured MF vector or PSD (current) and predicted range. A typical non-event indication would exhibit a PSD within the threshold alerts bands (pink) whereas and a typical event indication (rapidly developing crack) would exhibit a measured PSD above the maximum threshold across a range of frequency bands.

Returning to FIG. 27(*a*), in certain embodiments, before a leak/crack alert is raised by alert processor 820, a spectrum for the current PSD is subject to a direct assessment to determine whether the signal is Gaussian or non-Gaussian. In some embodiments, this may be achieved by obtaining a distribution of the signal magnitude in the current data signal 10 and determining whether the signal is normally distributed or not, noting that most (but not all) acoustic signals induced from the fluid discharge through a pipe crack are Gaussian. Determination of a non-Gaussian signal may lead to a leak/crack alert being downgraded or the associated spectrum subjected to further assessment.

For example, if the non-Gaussian signal is continuous within a data signal 10 then the current PSD derived from the signal will be structured. This structure may be assessed by analysing, for example, the number of power density "spikes" (out of upper bound occurrences), within the established frequency bands, such that if they occur in greater than a predetermined and/or selectable number of non-adjacent frequency bands (selectable) a non-leak noise source may be indicated.

Furthermore, two or more power density "spikes" with the peak frequencies being integer multiples of each other (selectable tolerance for defining integer) may also be indicative of a source other than through-wall pipe cracks.

If the non-Gaussian signal is not continuous then this is taken to eliminate a leak either from the pipe and/or upstream of water meters connected to the pipe. However, a leak downstream of system water meters could not be ruled out. At this point, in embodiments visual classification of the spectrum(s) may be undertaken manually or by using visual pattern recognition machine learning tools (with these tools trained, for example, to standard pipe leak and non-pipe leak noise signals). In this respect, FIGS. 33 to 36 illustrate example PSD and corresponding visualisations for different non-leak/crack source.

The operational response to the leak/crack alert is adjusted based on statistical quantification of the exceedance of the upper bound, and analysis of the associated spectrum, with 3 different response levels (matching practical response capability). For example, if the peak percentage above the upper bound is 10% or less (operator selectable) then the operational response time is slow (>2 weeks). However, if the peak percentage above the upper bound is 100% or more (operator selectable) then the operational response time is fast (<24 hours). Similarly, bounds can be established for the machine learning approaches and operational response levels established.

Example 4

Machine Learning Characterisation and Detection

As set out above, certain embodiments of the disclosure involve machine learning characterisation and detection. Embodiments which employ machine learning characterisation and detection may include statistical checks which are applied to a data signal 10 or features extracted from a data signal 10. In this respect, prior to proceeding further, in the below description, reference will be made to the data signal 10 as comprising a wave file. However, it is to be appreciated that the application of the method exemplified below is not to be so limited.

The following example relates to the application of a machine learning characterisation and detection of features which have been extracted using a process similar to that described above in relation to Example 2 above. However, it is to be appreciated that similar machine learning characterisation and detection techniques to those described below could equally be applied to the features extracted for other examples presented above.

Figure 28:
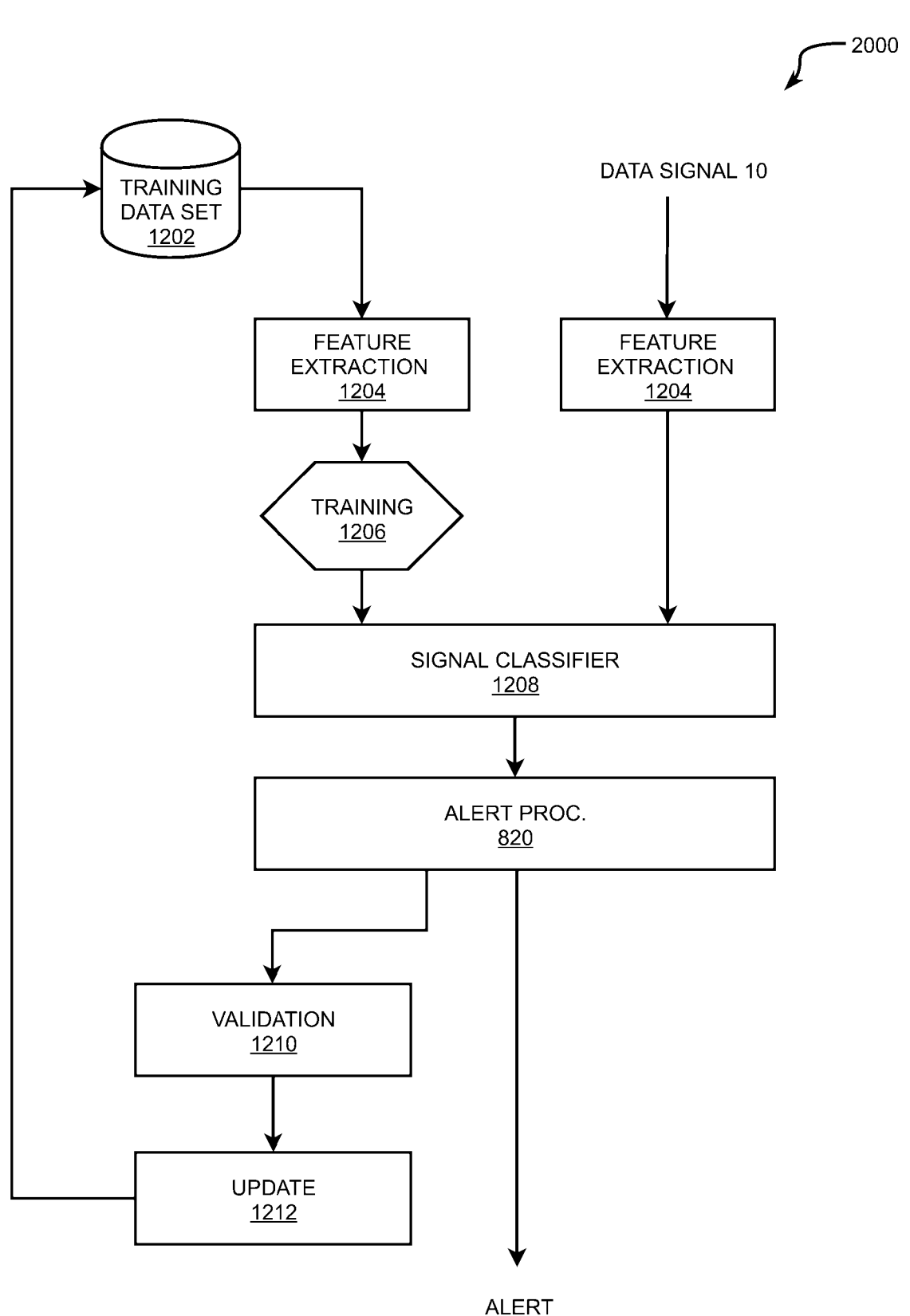
FIG. 28 illustrates a simplified schema of one embodiment of a machine learning characterisation and detection technique for processing a data signal according to an embodiment.

FIG. 28 illustrates a simplified schema 2000 of one embodiment of a machine learning characterisation and detection technique for processing a data signal 10 obtained from a sensor sensing a dynamic signal 5 (ref. FIG. 1) including signal components attributable to fluid flow at a location within an operational pipeline network 106 (ref. FIG. 1) to extract one or more features, and characterising the one or more extracted features to detect an indication of a structural anomaly event proximal a sensed location depending on the characterisation, wherein the structural anomaly event includes an occurrence and/or further development of a structural anomaly.

In the illustrated embodiment, a training data set 1202 comprising a set of data signals 10 (such as a wave file) including, for example, a leak/crack induced signal from cracked pipes, environmental noise forms, and no significant noise. The training data set 1201 is subjected to feature extraction process 1204 to extract time-domain and/or frequency domain features of the data signals 10, such as means, standard deviations, entropy, dominant frequencies and other statistics (e.g., noise distribution). The features are thus extracted from historical wave files including measured noises which may or may not include leak/crack induced signals. In this respect, it is not essential to use leak noise and no leak noise files from the same sensing location and wave files from plural sensing units can be used to significantly increase the number of sound files available for training and thus the size of the training data set 1202.

A signal classifier 1208 including, for example, a decision tree algorithm(s) or a supporting vector machine algorithm, or other classification algorithms, is then trained by training process 1206 to machine learn features associated with signals including leaks/crack or not. Training of the classifier 1208 by training process 1206 may be validated by validation process 1210 to check for accuracy at the completion of each classification step.

Figure 29:
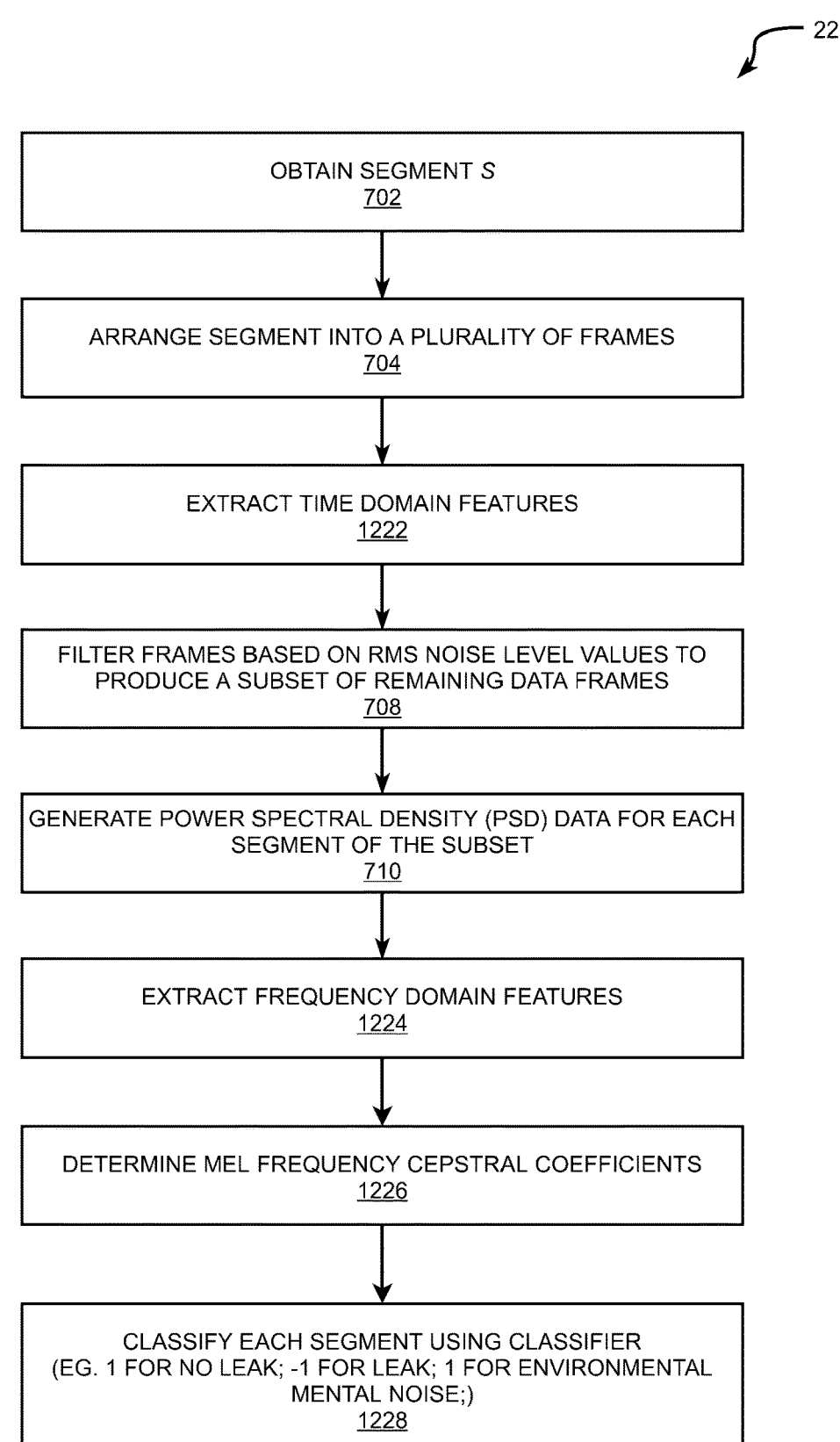
FIG. 29 is a flow diagram of a process for training a signal classifier according to one embodiment of a machine learning characterisation and detection technique.

Turning now to FIG. 29, there is shown a flow diagram 2200 of a process for training a signal classifier 1208 according to one embodiment of a machine learning characterisation and detection technique to permit processing of a current data signal 10 in the form of a data segment S. As shown, method includes steps 702, 704, 708 described previously.

In the example depicted in FIG. 29, at step 1222, time domain features are extracted by feature extraction process 1204 (ref. FIG. 28). Such features may include median amplitude values, interquartile ranges, persistence values, RMS values (such as mean and median RMS values), as non-limiting examples, and rates of change and the like as non-limiting examples.

At step 1224, frequency domain features are extracted by feature extraction process 1204 (ref. FIG. 28). Such features may include dominant frequency components, median frequency values, spectral entropy features, skewness, interquartile ranges, persistence spectrum related features, dominant frequency magnitude, spectral features such as spectral centroid, spectral spread and spectral flatness, as non-limiting examples.

At step 1226, mel-frequency cepstral coefficients are determined. Methods for determining mel-frequency cepstral coefficients for a data signal 10 in the form of a wave file would be well understood to a skilled person.

In certain embodiments, only features that contribute to the classification are selected as the input for the machine learning model. The feature can be selected by filter method (features are evaluated individually and selected before running a machine learning model), wrapped method (feature selection is treated as an optimization problem where a machine learning model is run iteratively to search for the optimal combination of features) or embedded method (the feature selection is based the feature importance which is a result of machine learning model).

Figure 30A:
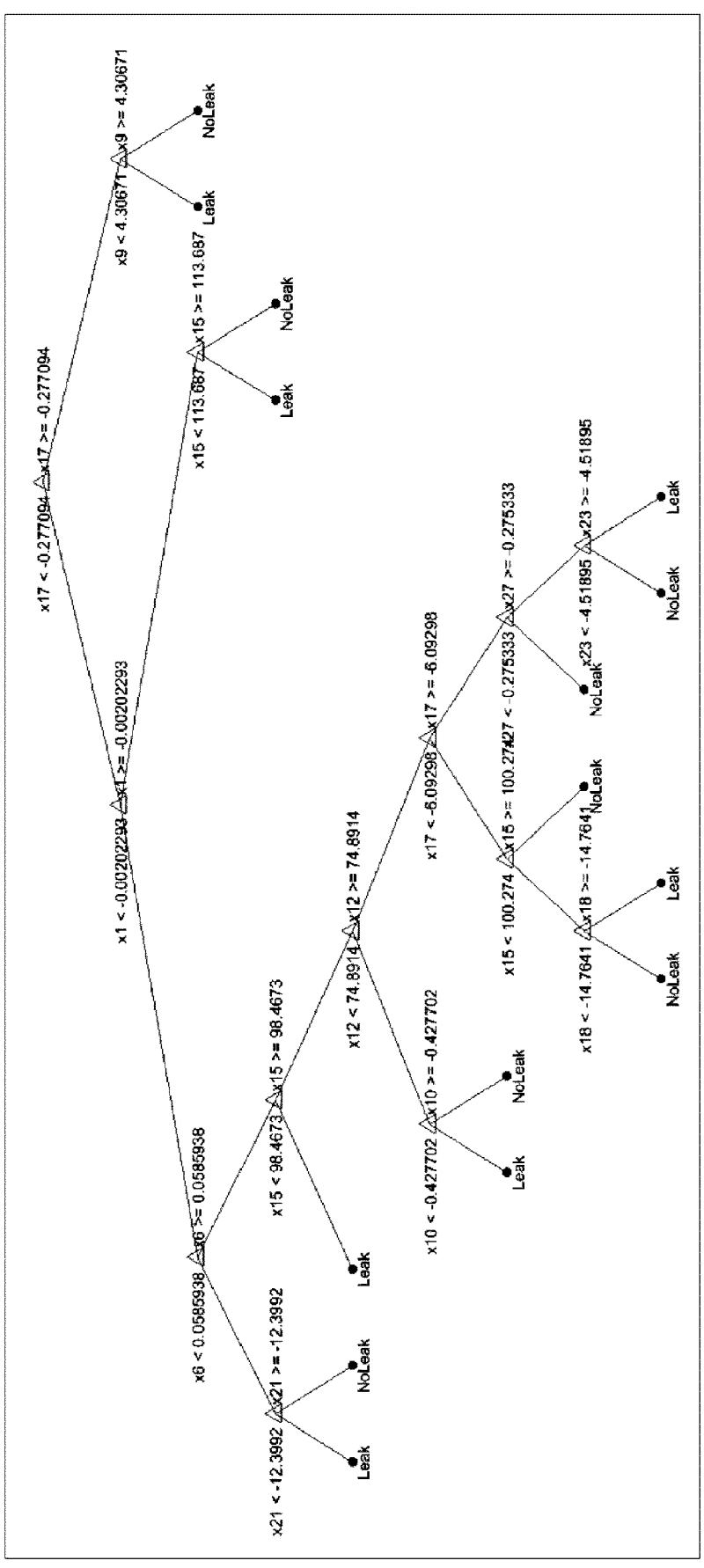
FIG. 30A is an example training map/matrix.

The results of the training and performance of the trained signal classifier 1208, when applied to current (or test) data, may be visualised using a decision tree map or confusion matrix, such as the decision tree 2300 illustrated in FIG. 30A. In this example, a leak/crack event is defined as the outcome "−1" and a no leak/crack event is defined as the outcome "1".

The depicted training decision tree map 2300 represents the numbers of true positive (leak/crack=−1), true negative (no leak/crack=1), false positive (leak/crack=−1) and false negative (leak/crack=1) occurrences after feature extraction and then training of the "decision tree" (for example) training classifier for 1800 events sets (physically confirmed leak/crack (main break type) and no leak/crack wave files) with twenty-seven features extracted from a raw acoustic wave file. In the example shown in FIG. 30, the extracted features are denoted as follows:

x1=mean;
x2=median;
x3=standard deviation;
x4=mean absolute deviation;
x5=25th percentile;
x6=75th percentile;
x7=interquartile range;
x8=skewness;
x9=kurtosis;
x10=signal entropy;
x11=spectral entropy;
x12=dominant frequency value;
x13=dominant frequency magnitude;
x14=dominant frequency ratio; and
x15 to x27=Mel-frequency cepstral coefficients 1 to 13.

Figure 30B:
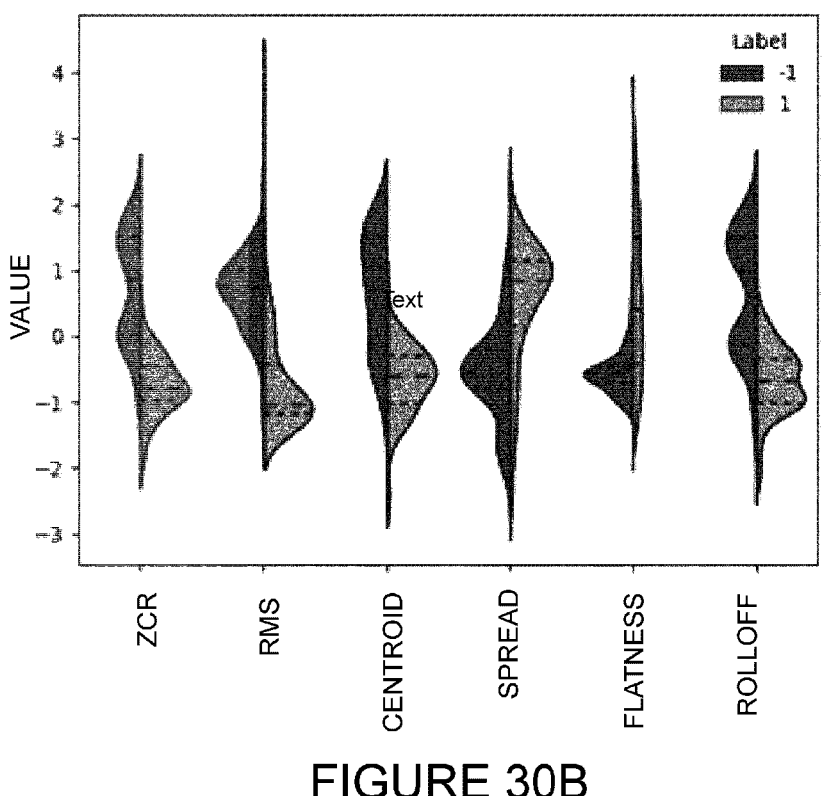
FIG. 30B is a "Violin" plot showing a sensitivity of six extracted features for classification of an event as either a "leak" or "no leak" labelled event.
Figure 30C:
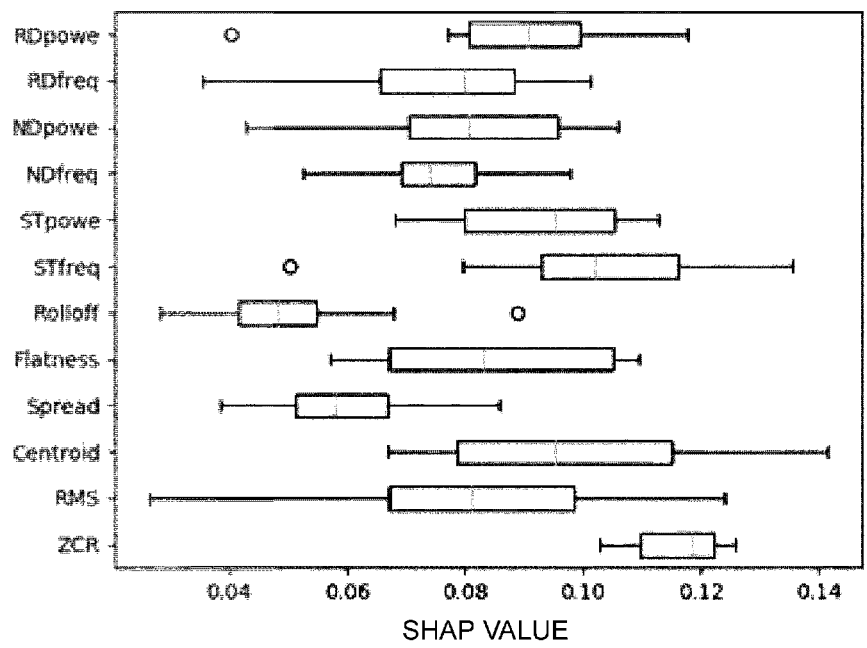
FIG. 30C shows "SHAP" coefficients obtained from predictions from a SVM classifier with associated extracted features and labels.

The sensitivity of the classifier training to the extracted features can be determined using "Violin" and "Box" plots, amongst other diagnostic techniques, as shown by way of example in FIG. 30B and FIG. 30C respectively.

The example "Violin" plot presented in FIG. 30B shows the sensitivity of six extracted features to the classification of an event as either a "leak" (1) or "no leak" (−1) labelled events. Where the values in the "Violin" plot for −1 and 1 labels are of a similar symmetric magnitude the feature is less valuable in the classification process. Where the values in the plot are not of similar symmetric magnitudes the feature is more useful in the classification process. The "Box" plot (ref. FIG. 30C) shows the variability of outcomes in the training process after a selectable number of training runs. Predictions from the SVM classifier, associated extracted features and labels are used to obtain the "SHAP" coefficients.

Figure 31:
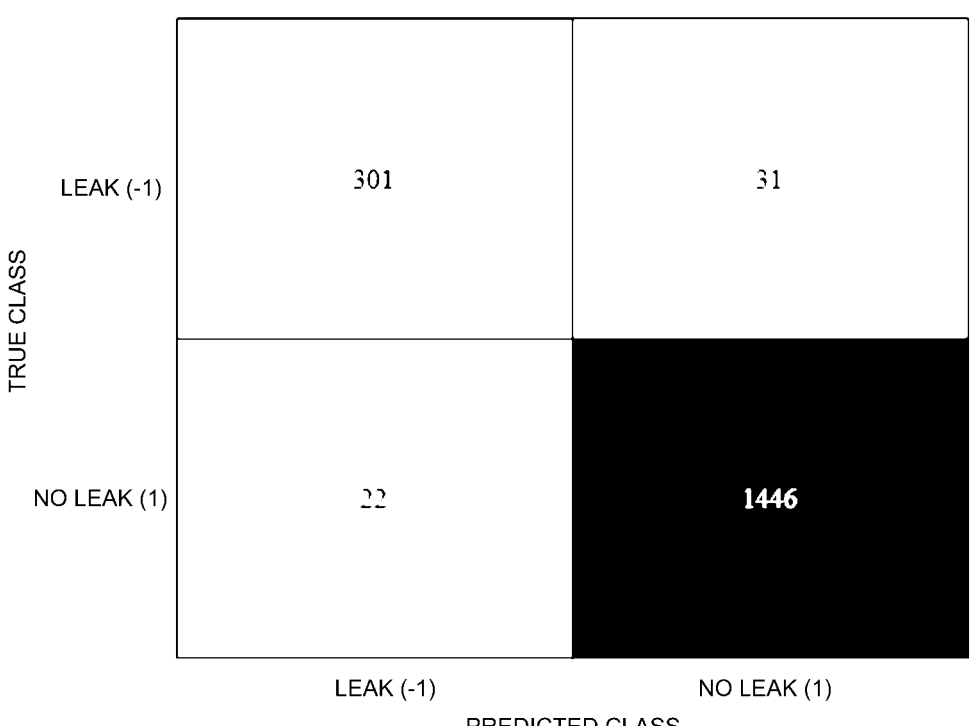
FIG. 31 and FIG. 32 are tables depicting example decision outcomes of a classifier according to an embodiment.

With reference now to FIG. 31, it can be seen that the "true positive" rate after training was 90.7% and the "false positive" rate after training was 9.3%. It can also be seen that the "true negative" rate after training was 98.5% and the "false negative" rate after training was 1.5%. It is envisaged that training outcomes may be further improved using more data.

Returning again now to FIG. 28, in certain embodiments, once the signal classifier 1208 has been trained with sufficient data to provide reliable classification, a current data signal 10, in the form of a current acoustic wave file, is received from a sensing unit 104 (ref. FIG. 1) for processing. The current wave file may then be subject to the same feature extraction process 1204 as applied to the historical wave files used to train the signal classifier 1208 to extract the associated set of features. Once a set of features have been extracted for the current data signal 10, the extracted features are input to the trained signal classifier 1208 for classification by the signal classifier 1208 (ref. FIG. 28).

During this classification, based on the extracted features, signal classifier 1208 then makes a prediction, for processing by alert processor 820, as to whether the current data signal 10 includes features indicating a structural anomaly event, such as a leak/crack event, or whether it does not include such features.

Accuracy of the prediction may be validated (either by field leak/crack localisation and the repair of a water system fault (including main breaks) or not (with no subsequent water system fault emerging). Validation of the prediction (whether accurate or not) may provide a further training information that may be used to update 1212 the historical wave files prior to the training process 1206 re-training the signal classifier 1208. A time period before re-training the signal classifier 1208 may be varied depending on the number of wave files that are being recorded and associated with physical outcomes. Examples of predictions for signal magnitude and PSD plots for leak/crack and no leak/crack events are shown in FIG. 33 to FIG. 36.

Figure 32:
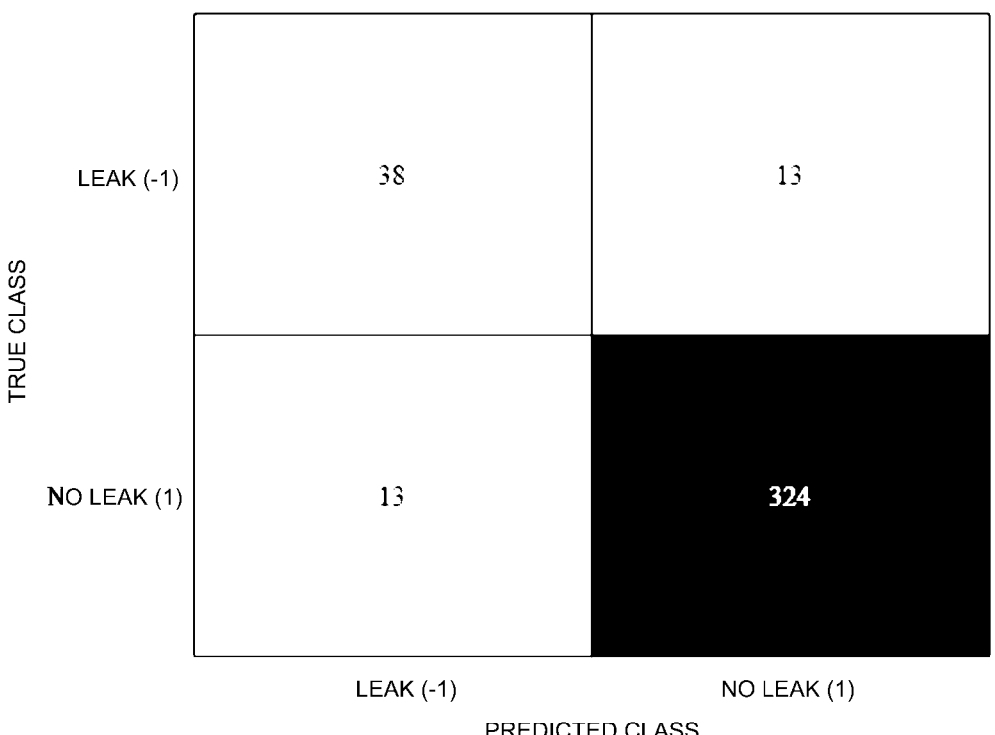
Figure 33:
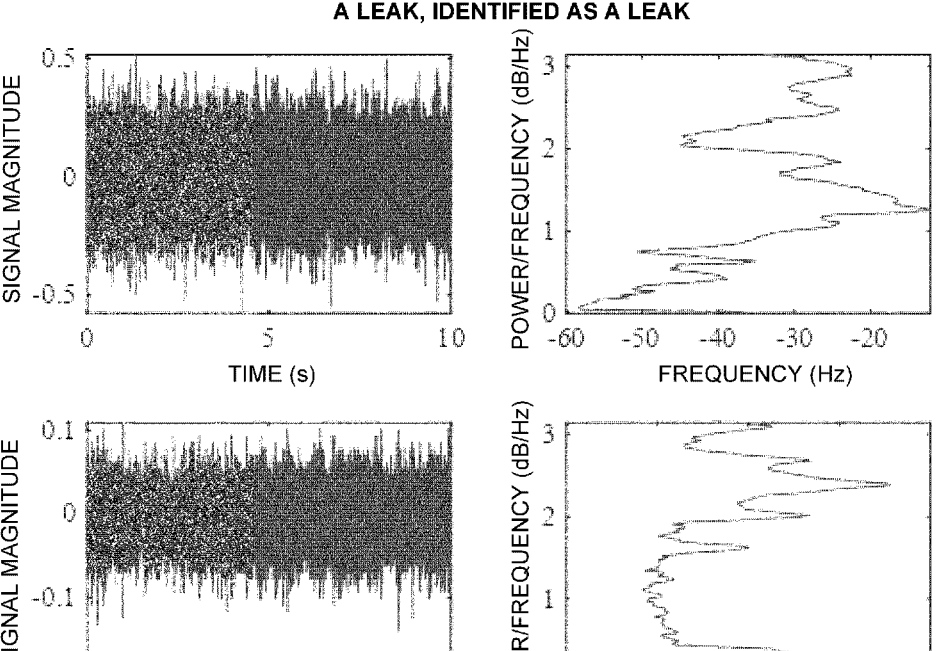
FIG. 33 to FIG. 36 show signal magnitude and PSD plots for leak/crack and no leak/crack events.
Figure 34:
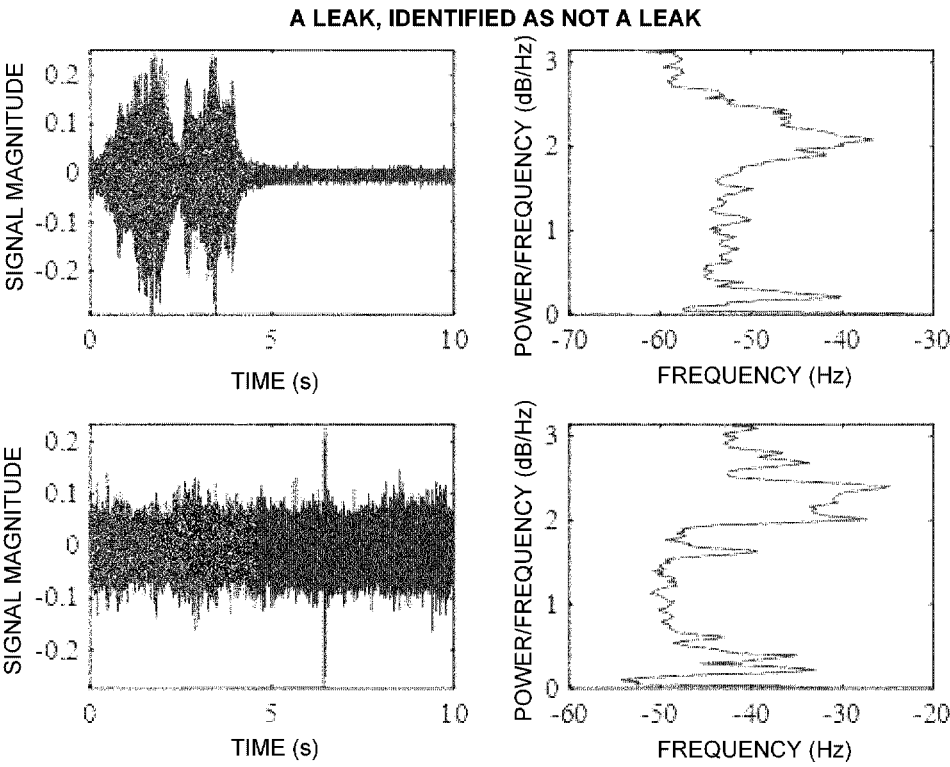
Figure 35:
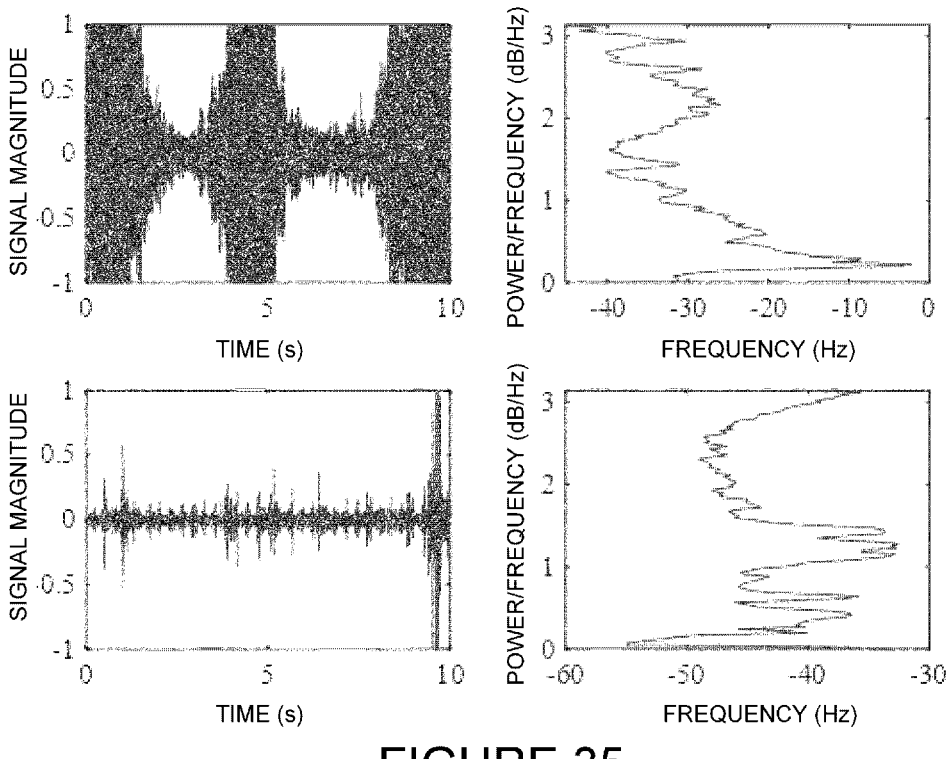
Figure 36:
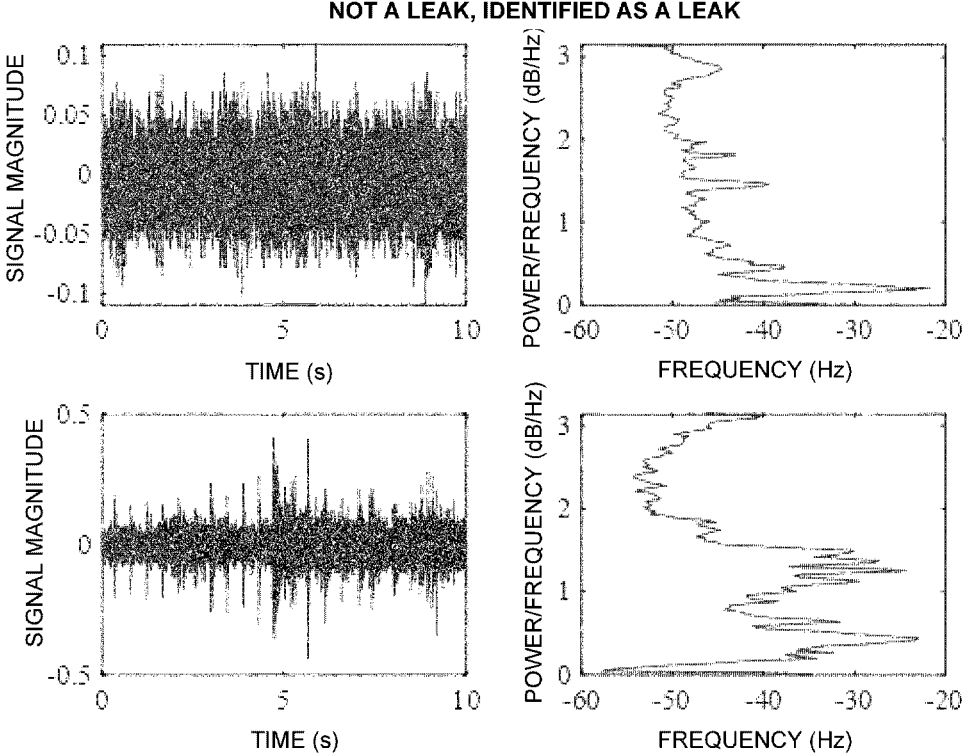

FIG. 32 illustrates the results after classifying feature extractions for 388 new or current test sets. As shown, the result was 74.5% "true positive" (ie. 38 out of 51 leak/crack events detected), 25.5% "false positive", 96.1% "true negative" and 3.9% "false negative" rates. Both in the case of training and then actual classification, the performance may be continually improved as the database of leak/crack and no leak/crack wave files.

As the number of validated leak/crack events and their associated wave files in a training set increases, it is envisaged that "true positive" outcomes will increase as re-training of the classifier is undertaken. Adjustments to the feature extraction process can also be made to weight existing features that are determined and used for classification and/or to add additional mathematically determined features which are more or less sensitive to particular features. Training has been conducted for wave files including circumferential and longitudinal cracks on pipes as well as a full range of environmental noises (typically illustrated in the figures above). Specific training for sets of water system faults, including main breaks but also including faults downstream of water meters, at valves and at joints, together with all or classes of environmental noise has been undertaken.

In embodiments, a signal classifier may include a Convolutional Neural Network (CNN). Unlike a decision tree or support vector machine (SVM) that use the features as inputs, a CNN does not require "hand-designed" low-level features and it is capable of learning mid to high-level information from the input data by the millions of parameters inside the deep neural network. CNN model takes the 2-dimensional spectrogram as the input, so that the loss of information from the raw wave file is minimum.

Training a CNN model requires a substantial amount of labelled data, which can be very expensive or sometime impractical. However, the machine learning models that use selected features require less data to train. These two types of model are complementary in terms of the size of training data required.

Figure 37A:
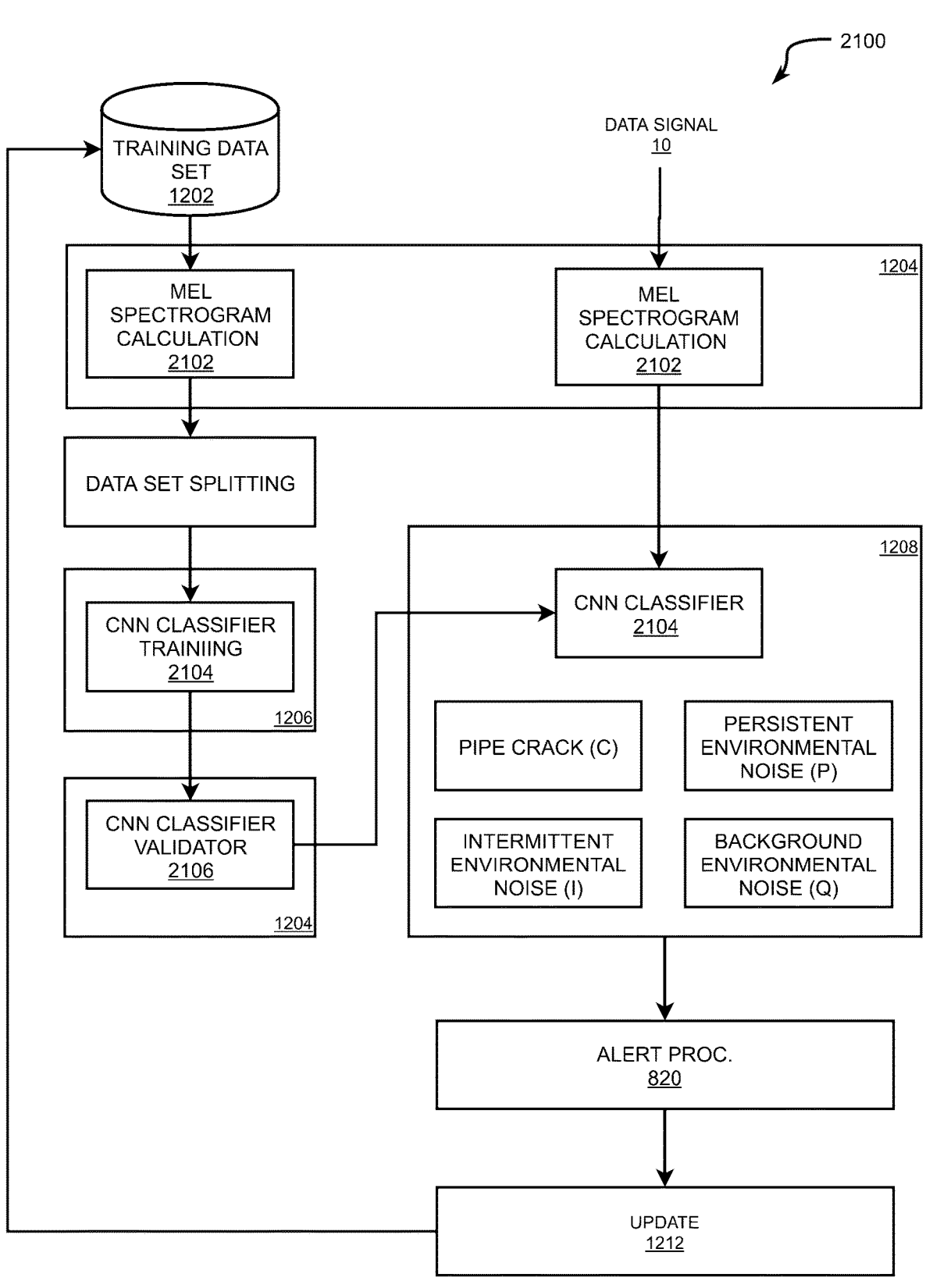
FIG. 37A is a functional block diagram for one example of a process of wave file classification for leak/break detection using a CNN.
Figure 37B:
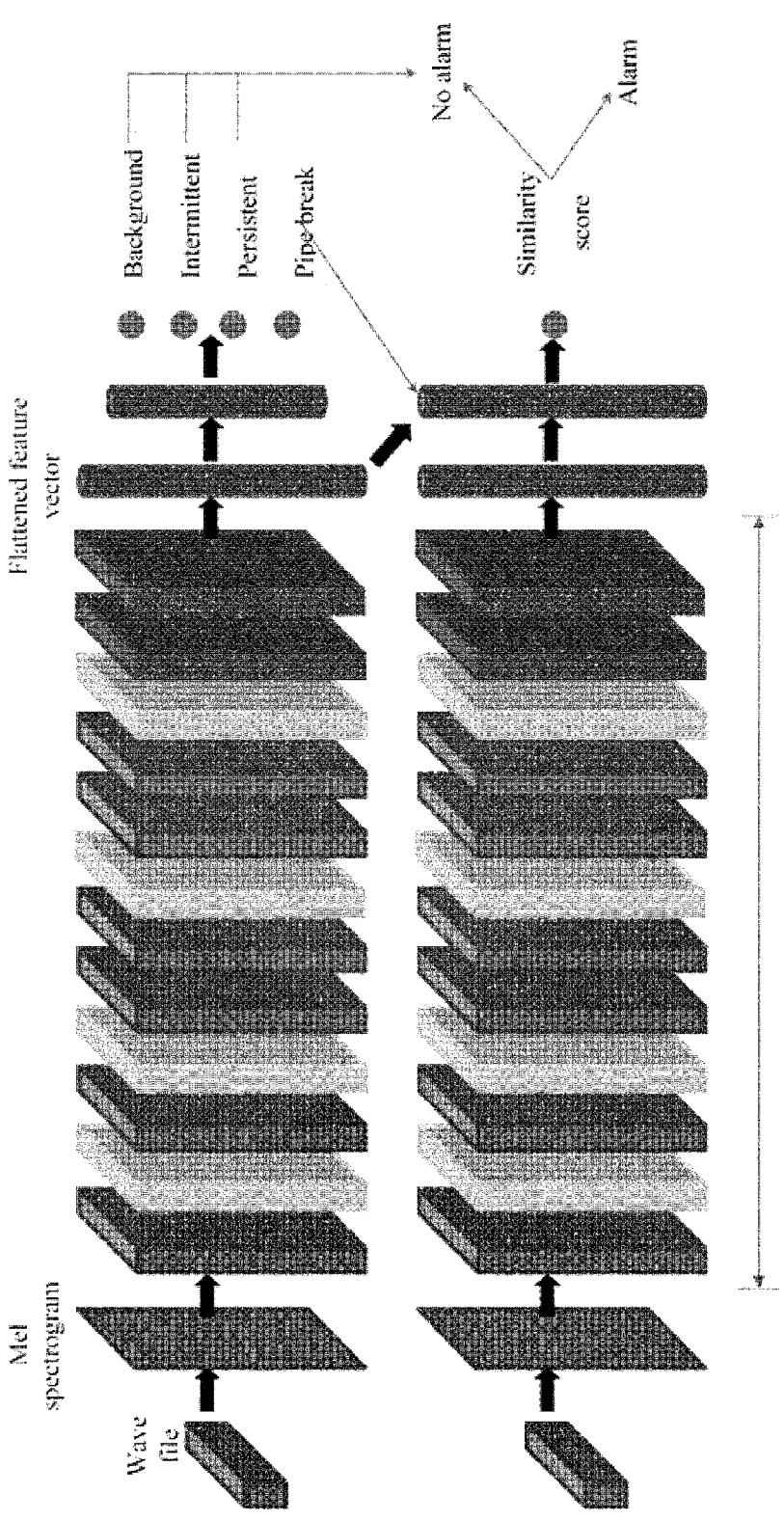
FIG. 37B is an example structure of a CNN Siamese Twin (containing a single CNN sub-structure) classifier.

FIG. 37A illustrates one example of a process of wave file classification for leak/break detection using a CNN. In the depicted example, the input for the training CNN classifier 2104 is a two-dimensional spectrogram determined by MEL spectrogram calculation 2102. The output of the trained CNN classifier 2104 is a probability distribution across multiple classes which in this example, comprise a "pipe crack/leak" class (C), a persistent environmental noise class" (P), an intermittent environmental noise" class (I), and a "background environmental noise/quiet" class (Q). The wave file is classified according to the class having the highest probability, and an alert is generated, if the wave file is classified as a pipe crack. FIG. 37B shows an example of a CNN (Siamese Twin) classifier structure (which also contains the structure of a single CNN classifier).

FIG. 38A depicts example frequency spectrums and corresponding visualisations for different non-leak/crack sources comprising, in the illustrated examples electrical (persistent), mechanical (persistent), traffic (intermittent) and meter noise (intermittent).

Figure 38B:
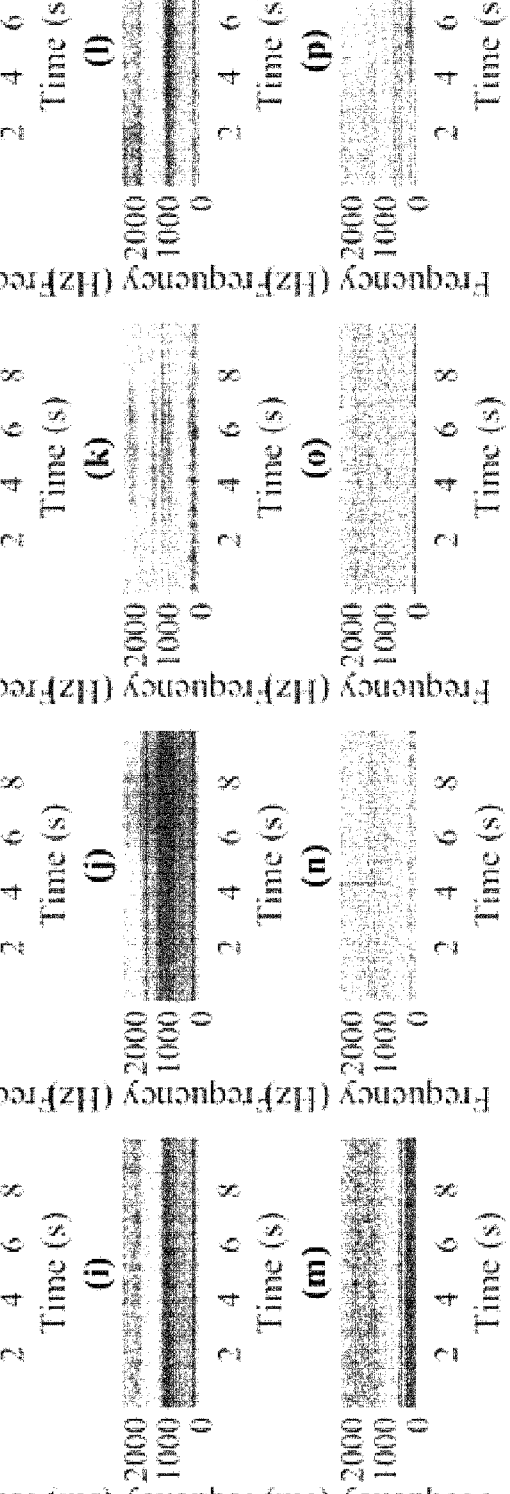
FIG. 38B depicts an example of an acoustic sound (wave) file library of labelled noises used for training of CNN and Siamese Twin CNN classifiers.

FIG. 38B depicts an example acoustic sound (wave) file library of noises which have been labelled as per the above described labelling categories for use in the training of CNN and Siamese Twin CNN classifiers.

Wave files confirmed as pipe cracks or other environmental noise by the field investigation may be included in the data set to retrain the CNN classifier 2104.

A data set of wave files with manual label may be collected for CNN classifier training and validating. Each wave file in this data set may contain a signal that is induced by unknown pipe breaks or known environmental sources. Data augmentation can be applied, if required, to increase the data size. The data is randomly split into training data and validation data. A CNN classifier that is validated by the validation data is then selected to process wave files.

Figure 39:
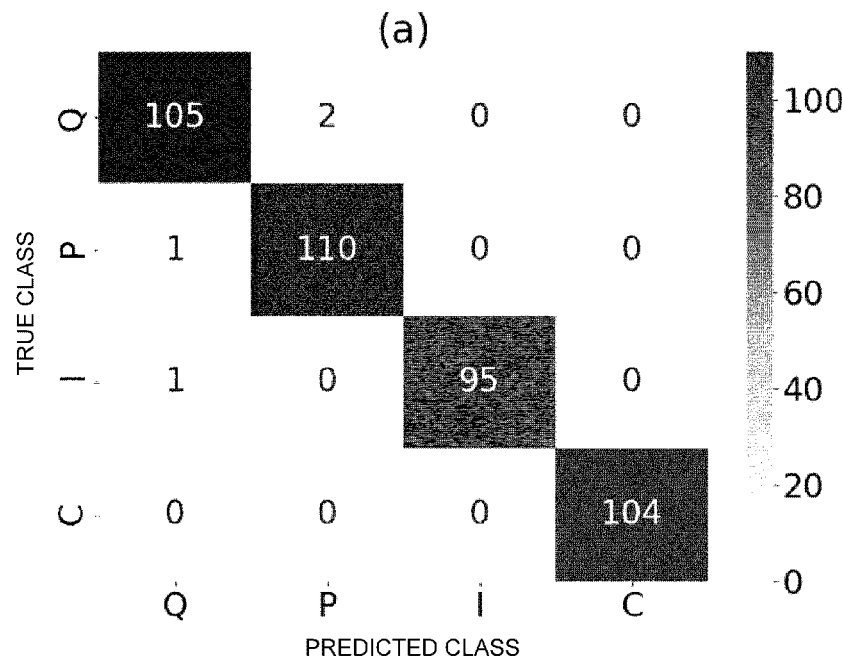
FIGS. 39 and 40 are tables depicting example decision outcomes of a classifier according to an embodiment.

With reference now to FIG. 39, it can be seen that the accuracy of CNN training model was 99.04%. All pipe crack (C) related wave files were successfully classified, that is the "false positive" rate is 0% and the "false negative" rate is 0%.

Figure 40:
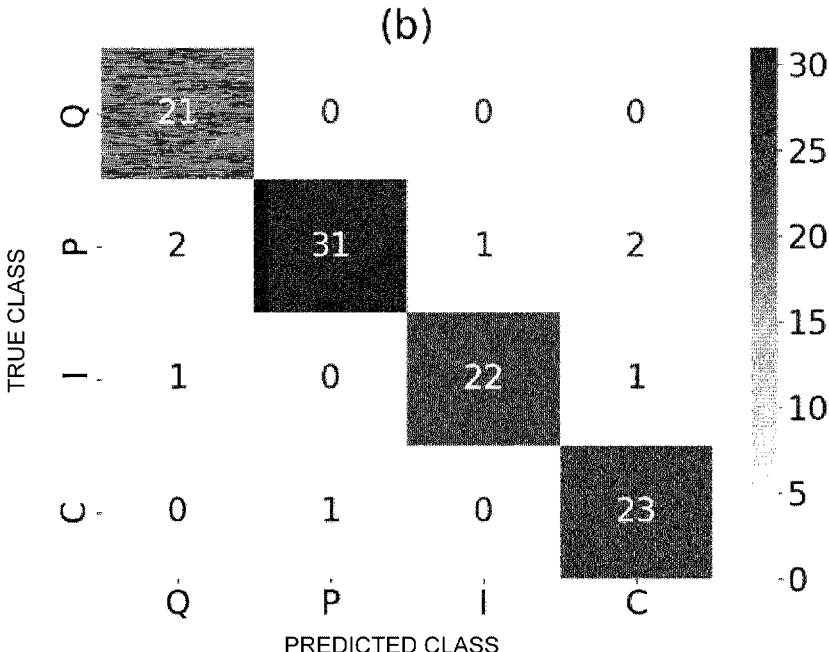

In certain embodiments, a CNN training model may be validated by validation data that the training model hasn't seen during training. One example of a confusion matrix arising from such a validation process is shown in FIG. 40. As shown. In this example, the accuracy of training model using validation data set was 92.38%. For the class of "pipe crack" (C) which is the most interest, the false positive rate is 11.54% and the false negative rate is 4.17%. It is envisaged that training outcomes may be further improved using more data.

In view of the above, it will be appreciated that embodiments of the disclosure may involve various techniques for processing a data signal from one or more sensors to obtain an indication of an occurrence and/or further development of a structural anomaly event at one or more locations within an operational pipeline network. Embodiments of the present disclosure process the data signal to extract one or more features and characterise the one or more extracted features to detect an indication of a structural anomaly event proximal the location depending on the characterisation.

As described above, various one or more features may be extracted and characterised using different techniques. Furthermore, having detected a leak/crack event, embodiments may then classify the leak/crack event depending on the characterisation of the one or more features. In this respect, FIG. 41 shows a table listing example characterisations of features of a data signal for classifying a 'fault type' of a detected leak/crack event. Example classification characterisations are listed below:

Circumferential Cracks:
Spectral analysis: up to 3 new peaks with new energy in an associated PSD with the power density in any 50 Hz band being above a 15% threshold established using historical (no crack) PSDs;
Signal magnitude: between a 20 to 30 dB rise in acoustic noise level above sensed background acoustic noise level;
Environmental noise is greater than 80% "drowned out" by a new noise from the crack which has formed;
Crack growth time to 100% crack development: between 1 to 10 hrs=>20 dB/10 hrs=2 dB/hr (slowest rise rate) and 30 dB/1 hr=30 dB/hr (fastest rise rate); and
Have an elevated noise plateau after 90% crack development which remains stable (±10% variation) until repair.
Longitudinal Cracks:
Spectral analysis: one new peak when new (very short) crack is first detected in spectra or PSD with this peak occurring in a 50 Hz band anywhere between 100 to 2400 Hz with additional power intensity measured in this band above a 15% threshold established using historical (no crack) PSDs;

Spectral analysis: up to 10 new peaks with new energy in the associated PSD, in bands anywhere between 50 Hz to 300 Hz wide, when crack and associated noise has reached "stable" state described below;

Signal magnitude: up to 5 dB rise in acoustic noise level above the logger's background acoustic noise level during a period of slow and "stable" crack evolution (see below)

Signal Magnitude: up to a further 5 to 15 dB rise in acoustic noise level above the sensing unit's sensed background noise level during a period of faster and "unstable" crack evolution (see below);

Evolution time between first detection of new power density in PSD (and associated sustained magnitude rise<5 dB), and then "near stable" crack period, through to "unstable" crack period during which the noise level increases before failure (see below), is currently in a range between 70 to 220 days (slowest growth rate);

Evolution time for noise from a crack to grow from an environmental noise level+5 dB (from above) to an environmental noise level +10 to +20 dB (during "unstable" crack development period) in a range between 5 to 20 days=>5 dB/20 days=0.25 dB/day (slowest rise rate) and 15 dB/5 days=3.0 (fastest rise rate) during the period of "unstable" crack growth; and Typically a continuous or semi-continuous increase in noise from the first occurrence of the crack to the repair or failure.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A method of detecting an indication of a structural anomaly event in an operational mains water distribution pipeline network, the method including:

providing, by a sensor, a data signal including signal components caused by vibro-acoustic energy generated by fluid flow at a location within the operational pipeline network;

periodically sampling the data signal at a predetermined time interval to obtain a set of sampled data segments (S) for a time period;

processing the data segments to determine power spectral density values for each data segment;

processing at least the determined power spectral density values using a machine learning model trained to
detect an indication of the structural anomaly event proximal the location and classify the structural anomaly event as either an occurrence and/or further development of a circumferential crack or a longitudinal crack, the machine learning model trained using temporal changes in one or more frequency domain features derived from power spectrum density values for previous time periods to distinguish between circumferential and longitudinal cracks; and generating an alert in response to the machine learning model detecting an indication of a structural anomaly event, the alert identifying the location and classification of the structural anomaly event.

2. A method according to claim 1 wherein the operational mains water distribution pipeline network includes a network of cast iron pipes, and wherein the alert indicates a required urgency of an operational response.

3. A method according to claim 1 wherein the one or more frequency domain features include a statistical value.

4. A method according to claim 1 wherein each data segment has an associated duration, and wherein the duration of each data segment is less than about 60 seconds.

5. A method according to claim 4 wherein the duration of each data segment is less than about 30 seconds.

6. A method according to claim 5 wherein the duration of each data segment is less than about 20 seconds.

7. A method according to claim 6 wherein the duration of each data segment is less than about 15 seconds.

8. A method according to claim 1 wherein the data signal is an acoustic signal and wherein each data segment is an uncompressed wave file.

9. A method according to claim 1 wherein the one or more frequency domain features includes at least one of:

a value of a median frequency;
a value of a mean frequency;
a value of a peak frequency;
a standard deviation of a power spectral density;
a kurtosis of a power spectral density;
a skewness of a power spectral density;
a spectral flatness;
a spectral centroid;
a spectral spread; and
a distribution of the power spectral density values.

10. A method according to claim 1 further comprising processing the data signal to extract one or more time domain features of the data signal and performing an analysis to characterise changes in at least one of the one or more time domain features.

11. A method according to claim 1 wherein the processing of at least the determined power spectral density values by the machine learning model comprises one or more of:

a. generating a prediction for at least one of the one or more frequency domain features for comparison with an instance of the at least one frequency domain feature;

b. recognising a trend or pattern associated with at least one of the one or more frequency domain features over the time period as indicative of a structural anomaly event; and c. identifying a predetermined behaviour and/or attribute of at least one of the at least one frequency domain features as indicative of a structural anomaly event.

12. A method according to claim 1, wherein processing the data segments to determine power spectral density values for each data segment includes:

framing each data segment as a sequence of data frames; and processing a selection of the data frames for each data segment to determine separate respective sets of power spectral density values for each data segment.

13. The method according to claim 12 wherein deriving one or more frequency-domain features from the power spectrum density values for previous time periods includes:

processing each separate set of power spectral density values to determine a respective first signal parameter value; and processing a set of the determined first signal parameter values to determine the one or more frequency domain features.

14. The method according to claim 13 wherein the first signal parameter includes a median frequency of one or more the power spectral densities derived from or for the data signal.

15. The method of claim 14, wherein the median frequency is a normalised median frequency.

16. The method of claim 13 wherein the first signal parameter includes a root-mean-squared noise derived for or from the data signal.

17. The method of claim 13 wherein processing a set of determined first signal parameter values to identify an indicator value includes identifying the indicator value as a first signal parameter value which n % of an ordered set of the first signal parameter values exceed.

18. The method of claim 17 wherein n % is between about 50% and about 75%.

19. The method of claim 17 wherein n % is between about 75% and about 90%.

20. The method of claim 17 wherein n % is about 90%.

21. The method according to claim 1 further including detecting a change in a profile of the distribution of the power spectral density values for a current data segment of the set as an indicator of a structural anomaly event proximal the location.

22. A method according to claim 1 wherein the temporal changes include one or more new peaks in a power spectral density associated with the determined power spectral density values, each one or more new peak having a power density value above a threshold established using the power spectral density values from the previous time periods known to not be indicative of a circumferential or longitudinal crack.

23. A method according to claim 1 further comprising validating the detection by inspection of the mains water distribution pipeline network at the location and retraining the machine learning model depending on the presence of a circumferential or longitudinal crack at the location to improve the accuracy of the detection.

24. A system for processing a data signal obtained from a sensor sensing a dynamic signal including signal components caused by vibro-acoustic energy generated by fluid flow at a location within an operational mains water distribution pipeline network to detect an indication of a structural anomaly event, the system including:

a memory;

a set of computer readable instructions stored in the memory;

a processor coupled to the memory, the processor configured to execute the set of computer readable instructions and use a machine learning model trained to detect an indication of the structural anomaly event proximal the location and classify the structural anomaly event as either an occurrence and/or further development of a circumferential crack or a longitudinal crack, to:

periodically sample the data signal at a predetermined time interval to obtain a set of sampled data segments(S) for a time period;

process the data segments to determine power spectral density values for each data-segment;

process at least the determined power spectral density values using the neural network; and generate an alert in response to the machine learning model detecting an indication of a structural anomaly event, the alert identifying the location and classification of the structural anomaly event, wherein the machine learning model is trained using temporal changes in one or more frequency domain features derived from power spectrum density values for previous time periods to distinguish between circumferential and longitudinal cracks.

25. An apparatus for processing a data signal obtained from a sensor sensing a dynamic signal including signal components caused by vibro-acoustic energy generated by fluid flow at a location within an operational mains water distribution pipeline network to detect an indication of a structural anomaly event, the apparatus including:

means for periodically sampling the data signal at a predetermined time interval to obtain a set of sampled data segments (S) for a time period;

means for processing the data segments to determine power spectral density values for each data segment;

means for processing at least the determined power spectral density values using a machine learning model trained to detect an indication of the structural anomaly event proximal the location and classify the structural anomaly event as either an occurrence and/or further development of a circumferential crack or a longitudinal crack, the machine learning model trained using temporal changes in one or more frequency domain features derived from power spectrum density values for previous time periods to distinguish between circumferential and longitudinal cracks; and means for generating an alert in response to the machine learning model detecting the indication of a structural anomaly event, the alert identifying the location and classification of the structural anomaly event.

26. A non-transitory computer-readable storage device storing instructions that, when executed by a processor, cause the processor to perform operations comprising:

obtaining a data signal from a sensor sensing a dynamic signal including signal components caused by vibro-acoustic energy generated by to fluid flow at a location within an operational pipeline network;

processing the data signal to determine power spectral density values for one or more frequency bands of the data signal;

processing at least the determined power spectral density values using a machine learning model trained to detect an indication of the structural anomaly event proximal the location and classify the structural anomaly event as either an occurrence and/or further development of a circumferential crack or a longitudinal crack, the machine learning model trained using temporal changes in one or more frequency domain features derived from power spectrum density values for previous time periods to distinguish between circumferential and longitudinal cracks; and generating an alert in response to the machine learning model detecting an indication of a structural anomaly event, the alert identifying the location and classification of the structural anomaly event.

\* \* \* \* \*